United States Patent
Schlom et al.

(10) Patent No.: US 11,732,017 B2
(45) Date of Patent: *Aug. 22, 2023

(54) HLA-A24 AGONIST EPITOPES OF MUC1-C ONCOPROTEIN AND COMPOSITIONS AND METHODS OF USE

(71) Applicant: The USA, as represented by the Secretary, Dept. of Health and Human Services, Bethesda, MD (US)

(72) Inventors: Jeffrey Schlom, Potomac, MD (US); Kwong-Yok Tsang, Bethesda, MD (US)

(73) Assignee: The USA, as represented by the Secretary, Dept. of Health and Human Services, Bethesda, MD (US)

( * ) Notice: Subject to any disclaimer, the term of this patent is extended or adjusted under 35 U.S.C. 154(b) by 334 days.

This patent is subject to a terminal disclaimer.

(21) Appl. No.: 17/240,260

(22) Filed: Apr. 26, 2021

(65) Prior Publication Data

US 2021/0253656 A1    Aug. 19, 2021

Related U.S. Application Data

(62) Division of application No. 16/715,038, filed on Dec. 16, 2019, now Pat. No. 11,155,588, which is a division of application No. 16/034,654, filed on Jul. 13, 2018, now Pat. No. 10,508,141, which is a division of application No. 15/031,435, filed as application No. PCT/US2014/061723 on Oct. 22, 2014, now Pat. No. 10,035,832.

(60) Provisional application No. 61/894,482, filed on Oct. 23, 2013.

(51) Int. Cl.
| | |
|---|---|
| C07K 14/47 | (2006.01) |
| C07K 14/82 | (2006.01) |
| A61K 38/19 | (2006.01) |
| A61K 38/20 | (2006.01) |
| A61K 38/21 | (2006.01) |
| A61K 38/22 | (2006.01) |
| A61K 31/00 | (2006.01) |
| A61K 45/06 | (2006.01) |
| A61K 39/00 | (2006.01) |
| A61K 39/39 | (2006.01) |
| C12N 7/00 | (2006.01) |
| A61K 38/00 | (2006.01) |

(52) U.S. Cl.
CPC .......... *C07K 14/4727* (2013.01); *A61K 31/00* (2013.01); *A61K 38/191* (2013.01); *A61K 38/193* (2013.01); *A61K 38/195* (2013.01); *A61K 38/20* (2013.01); *A61K 38/217* (2013.01); *A61K 38/22* (2013.01); *A61K 39/00117* (2018.08); *A61K 39/39* (2013.01); *A61K 45/06* (2013.01); *C07K 14/82* (2013.01); *C12N 7/00* (2013.01); *A61K 38/00* (2013.01); *A61K 2039/5154* (2013.01); *A61K 2039/53* (2013.01); *A61K 2039/55588* (2013.01); *C07K 2319/00* (2013.01); *C12N 2710/24143* (2013.01); *C12N 2710/24171* (2013.01)

(58) Field of Classification Search
CPC .................................................. C07K 14/4727
See application file for complete search history.

(56) References Cited

U.S. PATENT DOCUMENTS

| | | | |
|---|---|---|---|
| 6,546,643 | B2 | 4/2003 | Lotze et al. |
| 7,118,738 | B2 | 10/2006 | Schlom et al. |
| 7,342,094 | B1 | 3/2008 | Karsten et al. |
| 7,696,306 | B2 | 4/2010 | Hollingsworth et al. |
| 8,193,309 | B2 | 6/2012 | Hollingsworth et al. |
| 10,035,832 | B2 | 7/2018 | Schlom et al. |
| 10,508,141 | B2 | 12/2019 | Schlom et al. |
| 11,155,588 | B2 * | 10/2021 | Schlom ............... A61K 38/195 |
| 2005/0282744 | A1 | 12/2005 | Hollingsworth et al. |
| 2008/0063653 | A1 | 3/2008 | Schlom et al. |
| 2010/0190720 | A1 | 7/2010 | Hollingsworth et al. |
| 2012/0270798 | A1 | 10/2012 | Hollingsworth et al. |
| 2020/0109181 | A1 | 4/2020 | Schlom et al. |

FOREIGN PATENT DOCUMENTS

| | | |
|---|---|---|
| JP | 2010-505850 | 2/2010 |
| JP | 2012-522500 | 9/2012 |
| WO | WO 03/106648 | 12/2003 |
| WO | WO 2006/088906 | 8/2006 |
| WO | WO 2013/024972 | 2/2013 |
| WO | WO 2013/025972 | 2/2013 |
| WO | WO 2013/103658 | 7/2013 |

OTHER PUBLICATIONS

Genbank Accession No. AAP97018.1 (dated Apr. 26, 2013).
Genbank Accession No. AY327587.1 (dated Apr. 26, 2013).
Genbank Accession No. NM_001018016.1 (dated Feb. 6, 2011).
Genbank Accession No. NM_001018017 (dated Apr. 26, 2016).
Genbank Accession No. NM_002456.4 (dated Feb. 6, 2 011).
Genbank Accession No. NP_001018016.1 (dated Apr. 23, 2016).
Genbank Accession No. NP_001018017.1 (dated Apr. 23, 2016).
Genbank Accession No. NP_001191214 (dated Mar. 15, 2015).
Genbank Accession No. NP_002447.4 (dated Mar. 15, 2 015).
Grey et al., "Class I MHC-peptide interactions: structural requirements and functional implications," Cancer Surv., 22, 37-49 (1995).
Hayes et al., "Comparison of circulating CA15-3 and carcinoembryonic antigen levels in patients with breast cancer," J. Clin. Oncol., 4 (10), 1542-1550 (1986).

(Continued)

*Primary Examiner* — Prema M Mertz
(74) *Attorney, Agent, or Firm* — Sheridan Ross P.C.

(57) ABSTRACT

The invention provides a human cytotoxic T lymphocyte (CTL) agonist epitope from the C-terminal subunit of mucin 1 (MUC1-C), which can be used as a peptide, polypeptide (protein), and/or in vaccine or other composition for the prevention or therapy of cancer. The invention further provides a nucleic acid encoding the peptide, protein, or polypeptide, a vector comprising the nucleic acid, a cell comprising the peptide, polypeptide, nucleic acid, or vector, and compositions thereof.

6 Claims, No Drawings

Specification includes a Sequence Listing.

(56) References Cited

OTHER PUBLICATIONS

Hu et al., "MUC1 cytoplasmic tail: a potential therapeutic target for ovarian carcinoma," Expert Rev. Anticancer Ther., 6 (8), 1261-1271 (2006).
Khodarev et al., "MUC1-induced transcriptional programs associated with tumorigenesis predict outcome in breast and lung cancer," Cancer Res., 69 (7), 2833-2837 (2009).
Kondo et al., "Adoptive Immunotherapy for Pancreatic Cancer Using MUC1 Peptide-pulsed Dendritic Cells and Activated T Lymphocytes," Anticancer Res., 28 (1B), 379-388 (2008).
Kuttler et al., "An algorithm for the prediction of proteasomal cleavages", Journal of Molecular Biology, 2000, vol. 298, Iss. 3, pp. 417-429.
Lan et al., "Cloning and sequencing of a human pancreatic tumor mucin cDNA," J. Biol. Chem., 265 (25), 15294-9 (1990).
Li et al., "Human DF3/MUC1 carcinoma-associated protein functions as an oncogene," Oncogene, 22, 6107-10 (2003).
Li et al., "The epidermal growth factor receptor regulates interaction of the human DF3/MUC1 carcinoma antigen with c-Src and beta-catenin," J. Biol. Chem., 276 (38), 35239-42 (2001).
Madurga et al., "Design of enhanced agonists through the use of a new virtual screening method: application to peptides that bind class I major histocompatibility complex (MHC) molecules," Protein Science, 14, 2069-2079 (2005).
Mitchell et al., "The cytotoxic T cell response to peptide analogs of the HLA-A*0201—restricted MUC1 signal sequence epitope, M1.2," Cancer Immunol. Immunother., 5, 287-301 (2007).
Raina et al., "Direct targeting of the mucin 1 oncoprotein blocks survival and tumorigenicity of human breast carcinoma cells," Cancer Res., 69 (12), 5133-41 (2009).
Ren et al., "Human MUC1 carcinoma-associated protein confers resistance to genotoxic anticancer agents," Cancer Cell., 5, 163-75 (2004).
Roulois et al., "MUC1-Specific Cytotoxic T Lymphocytes in Cancer Therapy: Induction and Challenge," BioMed Research International, 2013 (871936), 1-10 (2013).
Swissprot Accession No. P15941.3 (dated Apr. 13, 2016).
Terasawa et al., "Identification and characterization of a human agonist cytotoxic T-lymphocyte epitope of human prostate-specific antigen," Clin. Cancer Res., 8, 41-53 (2002).
Tsang et al., "A human cytotoxic T-lymphocyte epitope and its agonist epitope from the nonvariable number of tandem repeat sequence of MUC-1," Clinical Cancer Research, 10, 2139-2149 (2004).
Vermeer et al., "Segregation of receptor and ligand regulates activation of epithelial growth factor receptor," Nature, 442, 322-6 (2003).
Wei et al., "Human mucin 1 oncoprotein represses transcription of the p53 tumor suppressor gene," Cancer Res., 67 (4), 1853-8 (2007).
International Search Report, Application No. PCT/US2014/061723, dated Jul. 10, 2015.
International Preliminary Report on Patentability, Application No. PCT/US2014/061723, dated Apr. 26, 2016.

* cited by examiner

```
                         SEQUENCE LISTING

<160> NUMBER OF SEQ ID NOS: 19

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide

<400> SEQUENCE: 1

Lys Tyr His Pro Met Ser Glu Tyr Ala Leu
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide

<400> SEQUENCE: 2

Lys Tyr Thr Asn Pro Ala Val Ala Leu
1               5

<210> SEQ ID NO 3
<211> LENGTH: 10
<212> TYPE: PRT
<213> ORGANISM: Artificial Sequence
<220> FEATURE:
<223> OTHER INFORMATION: Synthetic peptide

<400> SEQUENCE: 3

Thr Tyr His Pro Met Ser Glu Tyr Pro Thr
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4

Ser Tyr Thr Asn Pro Ala Val Ala Ala
1               5

<210> SEQ ID NO 5
<211> LENGTH: 1255
<212> TYPE: PRT
<213> ORGANISM: Homo sapiens

<400> SEQUENCE: 5

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
                20                  25                  30

Gly Glu Lys Glu Thr Ser Ala Thr Gln Arg Ser Ser Val Pro Ser Ser
            35                  40                  45

Thr Glu Lys Asn Ala Val Ser Met Thr Ser Ser Val Leu Ser Ser His
        50                  55                  60
```

```
Ser Pro Gly Ser Gly Ser Thr Thr Gln Gly Gln Asp Val Thr Leu
 65                  70                  75                  80

Ala Pro Ala Thr Glu Pro Ala Ser Gly Ser Ala Ala Thr Trp Gly Gln
                 85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
            115                 120                 125

Gly Ser Thr Ala Pro Pro Ala His Gly Val Thr Ser Ala Pro Asp Thr
        130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
            195                 200                 205

Gly Ser Thr Ala Pro Pro Ala His Gly Val Thr Ser Ala Pro Asp Thr
        210                 215                 220

Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                245                 250                 255

Gly Val Thr Ser Ala Pro Asp Thr Arg Pro Ala Pro Gly Ser Thr Ala
            260                 265                 270

Pro Pro Ala His Gly Val Thr Ser Ala Pro Asp Thr Arg Pro Ala Pro
            275                 280                 285

Gly Ser Thr Ala Pro Pro Ala His Gly Val Thr Ser Ala Pro Asp Thr
        290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335

Gly Val Thr Ser Ala Pro Asp Thr Arg Pro Ala Pro Gly Ser Thr Ala
            340                 345                 350

Pro Pro Ala His Gly Val Thr Ser Ala Pro Asp Thr Arg Pro Ala Pro
            355                 360                 365

Gly Ser Thr Ala Pro Pro Ala His Gly Val Thr Ser Ala Pro Asp Thr
        370                 375                 380

Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
                405                 410                 415

Gly Val Thr Ser Ala Pro Asp Thr Arg Pro Ala Pro Gly Ser Thr Ala
            420                 425                 430

Pro Pro Ala His Gly Val Thr Ser Ala Pro Asp Thr Arg Pro Ala Pro
            435                 440                 445

Gly Ser Thr Ala Pro Pro Ala His Gly Val Thr Ser Ala Pro Asp Thr
        450                 455                 460

Arg Pro Ala Pro Gly Ser Thr Ala Pro Pro Ala His Gly Val Thr Ser
465                 470                 475                 480

Ala Pro Asp Thr Arg Pro Ala Pro Gly Ser Thr Ala Pro Pro Ala His
```

-continued

```
                485                 490                 495
Gly Val Thr Ser Ala Pro Asp Thr Arg Pro Ala Pro Gly Ser Thr Ala
                500                 505                 510
Pro Pro Ala His Gly Val Thr Ser Ala Pro Asp Thr Arg Pro Ala Pro
                515                 520                 525
Gly Ser Thr Ala Pro Pro Ala His Gly Val Thr Ser Ala Pro Asp Thr
                530                 535                 540
Arg Pro Ala Pro Gly Ser Thr Ala Pro Pro Ala His Gly Val Thr Ser
545                 550                 555                 560
Ala Pro Asp Thr Arg Pro Ala Pro Gly Ser Thr Ala Pro Pro Ala His
                565                 570                 575
Gly Val Thr Ser Ala Pro Asp Thr Arg Pro Ala Pro Gly Ser Thr Ala
                580                 585                 590
Pro Pro Ala His Gly Val Thr Ser Ala Pro Asp Thr Arg Pro Ala Pro
                595                 600                 605
Gly Ser Thr Ala Pro Pro Ala His Gly Val Thr Ser Ala Pro Asp Thr
                610                 615                 620
Arg Pro Ala Pro Gly Ser Thr Ala Pro Pro Ala His Gly Val Thr Ser
625                 630                 635                 640
Ala Pro Asp Thr Arg Pro Ala Pro Gly Ser Thr Ala Pro Pro Ala His
                645                 650                 655
Gly Val Thr Ser Ala Pro Asp Thr Arg Pro Ala Pro Gly Ser Thr Ala
                660                 665                 670
Pro Pro Ala His Gly Val Thr Ser Ala Pro Asp Thr Arg Pro Ala Pro
                675                 680                 685
Gly Ser Thr Ala Pro Pro Ala His Gly Val Thr Ser Ala Pro Asp Thr
                690                 695                 700
Arg Pro Ala Pro Gly Ser Thr Ala Pro Pro Ala His Gly Val Thr Ser
705                 710                 715                 720
Ala Pro Asp Thr Arg Pro Ala Pro Gly Ser Thr Ala Pro Pro Ala His
                725                 730                 735
Gly Val Thr Ser Ala Pro Asp Thr Arg Pro Ala Pro Gly Ser Thr Ala
                740                 745                 750
Pro Pro Ala His Gly Val Thr Ser Ala Pro Asp Thr Arg Pro Ala Pro
                755                 760                 765
Gly Ser Thr Ala Pro Pro Ala His Gly Val Thr Ser Ala Pro Asp Thr
                770                 775                 780
Arg Pro Ala Pro Gly Ser Thr Ala Pro Pro Ala His Gly Val Thr Ser
785                 790                 795                 800
Ala Pro Asp Thr Arg Pro Ala Pro Gly Ser Thr Ala Pro Pro Ala His
                805                 810                 815
Gly Val Thr Ser Ala Pro Asp Thr Arg Pro Ala Pro Gly Ser Thr Ala
                820                 825                 830
Pro Pro Ala His Gly Val Thr Ser Ala Pro Asp Thr Arg Pro Ala Pro
                835                 840                 845
Gly Ser Thr Ala Pro Pro Ala His Gly Val Thr Ser Ala Pro Asp Thr
                850                 855                 860
Arg Pro Ala Pro Gly Ser Thr Ala Pro Pro Ala His Gly Val Thr Ser
865                 870                 875                 880
Ala Pro Asp Thr Arg Pro Ala Pro Gly Ser Thr Ala Pro Pro Ala His
                885                 890                 895
Gly Val Thr Ser Ala Pro Asp Thr Arg Pro Ala Pro Gly Ser Thr Ala
                900                 905                 910
```

Pro Pro Ala His Gly Val Thr Ser Ala Pro Asp Thr Arg Pro Ala Pro
        915                 920                 925

Gly Ser Thr Ala Pro Pro Ala His Gly Val Thr Ser Ala Pro Asp Asn
    930                 935                 940

Arg Pro Ala Leu Gly Ser Thr Ala Pro Pro Val His Asn Val Thr Ser
945                 950                 955                 960

Ala Ser Gly Ser Ala Ser Gly Ser Ala Ser Thr Leu Val His Asn Gly
                965                 970                 975

Thr Ser Ala Arg Ala Thr Thr Thr Pro Ala Ser Lys Ser Thr Pro Phe
            980                 985                 990

Ser Ile Pro Ser His His Ser Asp Thr Pro Thr Thr Leu Ala Ser His
        995                 1000                1005

Ser Thr Lys Thr Asp Ala Ser Ser Thr His His Ser Ser Val Pro
    1010                1015                1020

Pro Leu Thr Ser Ser Asn His Ser Thr Ser Pro Gln Leu Ser Thr
    1025                1030                1035

Gly Val Ser Phe Phe Phe Leu Ser Phe His Ile Ser Asn Leu Gln
    1040                1045                1050

Phe Asn Ser Ser Leu Glu Asp Pro Ser Thr Asp Tyr Tyr Gln Glu
    1055                1060                1065

Leu Gln Arg Asp Ile Ser Glu Met Phe Leu Gln Ile Tyr Lys Gln
    1070                1075                1080

Gly Gly Phe Leu Gly Leu Ser Asn Ile Lys Phe Arg Pro Gly Ser
    1085                1090                1095

Val Val Val Gln Leu Thr Leu Ala Phe Arg Glu Gly Thr Ile Asn
    1100                1105                1110

Val His Asp Val Glu Thr Gln Phe Asn Gln Tyr Lys Thr Glu Ala
    1115                1120                1125

Ala Ser Arg Tyr Asn Leu Thr Ile Ser Asp Val Ser Val Ser Asp
    1130                1135                1140

Val Pro Phe Pro Phe Ser Ala Gln Ser Gly Ala Gly Val Pro Gly
    1145                1150                1155

Trp Gly Ile Ala Leu Leu Val Leu Val Cys Val Leu Val Ala Leu
    1160                1165                1170

Ala Ile Val Tyr Leu Ile Ala Leu Ala Val Cys Gln Cys Arg Arg
    1175                1180                1185

Lys Asn Tyr Gly Gln Leu Asp Ile Phe Pro Ala Arg Asp Thr Tyr
    1190                1195                1200

His Pro Met Ser Glu Tyr Pro Thr Tyr His Thr His Gly Arg Tyr
    1205                1210                1215

Val Pro Pro Ser Ser Thr Asp Arg Ser Pro Tyr Glu Lys Val Ser
    1220                1225                1230

Ala Gly Asn Gly Gly Ser Ser Leu Ser Tyr Thr Asn Pro Ala Val
    1235                1240                1245

Ala Ala Thr Ser Ala Asn Leu
    1250                1255

<210> SEQ ID NO 6
<211> LENGTH: 1209
<212> TYPE: DNA
<213> ORGANISM: Homo sapiens
<220> FEATURE:
<221> NAME/KEY: CDS
<222> LOCATION: (67)..(888)

-continued

<400> SEQUENCE: 6

```
acctctcaag cagccagcgc ctgcctgaat ctgttctgcc ccctccccac ccatttcacc      60 accacc atg aca ccg ggc acc cag tct cct ttc ttc ctg ctg ctg ctc      108
       Met Thr Pro Gly Thr Gln Ser Pro Phe Phe Leu Leu Leu Leu
         1               5                  10 ctc aca gtg ctt aca gtt gtt acg ggt tct ggt cat gca agc tct acc      156
Leu Thr Val Leu Thr Val Val Thr Gly Ser Gly His Ala Ser Ser Thr
 15              20                  25                  30 cca ggt gga gaa aag gag act tcg gct acc cag aga agt tca gtg ccc      204
Pro Gly Gly Glu Lys Glu Thr Ser Ala Thr Gln Arg Ser Ser Val Pro
                 35                  40                  45 agc tct act gag aag aat gct ttg tct act ggg gtc tct ttc ttt ttc      252
Ser Ser Thr Glu Lys Asn Ala Leu Ser Thr Gly Val Ser Phe Phe Phe
             50                  55                  60 ctg tct ttt cac att tca aac ctc cag ttt aat tcc tct ctg gaa gat      300
Leu Ser Phe His Ile Ser Asn Leu Gln Phe Asn Ser Ser Leu Glu Asp
         65                  70                  75 ccc agc acc gac tac tac caa gag ctg cag aga gac att tct gaa atg      348
Pro Ser Thr Asp Tyr Tyr Gln Glu Leu Gln Arg Asp Ile Ser Glu Met
 80                  85                  90 ttt ttg cag att tat aaa caa ggg ggt ttt ctg ggc ctc tcc aat att      396
Phe Leu Gln Ile Tyr Lys Gln Gly Gly Phe Leu Gly Leu Ser Asn Ile
 95                 100                 105                 110 aag ttc agg cca gga tct gtg gtg gta caa ttg act ctg gcc ttc cga      444
Lys Phe Arg Pro Gly Ser Val Val Val Gln Leu Thr Leu Ala Phe Arg
                115                 120                 125 gaa ggt acc atc aat gtc cac gac gtg gag aca cag ttc aat cag tat      492
Glu Gly Thr Ile Asn Val His Asp Val Glu Thr Gln Phe Asn Gln Tyr
            130                 135                 140 aaa acg gaa gca gcc tct cga tat aac ctg acg atc tca gac gtc agc      540
Lys Thr Glu Ala Ala Ser Arg Tyr Asn Leu Thr Ile Ser Asp Val Ser
        145                 150                 155 gtg agt gat gtg cca ttt cct ttc tct gcc cag tct ggg gct ggg gtg      588
Val Ser Asp Val Pro Phe Pro Phe Ser Ala Gln Ser Gly Ala Gly Val
    160                 165                 170 cca ggc tgg ggc atc gcg ctg ctg gtg ctg gtc tgt gtt ctg gtt gcg      636
Pro Gly Trp Gly Ile Ala Leu Leu Val Leu Val Cys Val Leu Val Ala
175                 180                 185                 190 ctg gcc att gtc tat ctc att gcc ttg gct gtc tgt cag tgc cgc cga      684
Leu Ala Ile Val Tyr Leu Ile Ala Leu Ala Val Cys Gln Cys Arg Arg
                195                 200                 205 aag aac tac ggg cag ctg gac atc ttt cca gcc cgg gat acc tac cat      732
Lys Asn Tyr Gly Gln Leu Asp Ile Phe Pro Ala Arg Asp Thr Tyr His
            210                 215                 220 cct atg agc gag tac ccc acc tac cac acc cat ggg cgc tat gtg ccc      780
Pro Met Ser Glu Tyr Pro Thr Tyr His Thr His Gly Arg Tyr Val Pro
        225                 230                 235 cct agc agt acc gat cgt agc ccc tat gag aag gtt tct gca ggt aat      828
Pro Ser Ser Thr Asp Arg Ser Pro Tyr Glu Lys Val Ser Ala Gly Asn
    240                 245                 250 ggt ggc agc agc ctc tct tac aca aac cca gca gtg gca gcc act tct      876
Gly Gly Ser Ser Leu Ser Tyr Thr Asn Pro Ala Val Ala Ala Thr Ser
255                 260                 265                 270 gcc aac ttg tag gggcacgtcg cccgctgagc tgagtggcca gccagtgcca         928
Ala Asn Leu ttccactcca ctcaggttct tcagggccag agccctgca ccctgtttgg gctggtgagc    988
tgggagttca ggtgggctgc tcacagcctc cttcagaggc cccaccaatt tctcggacac   1048
```

```
ttctcagtgt gtggaagctc atgtgggccc ctgagggctc atgcctggga agtgttgtgg    1108
tgggggctcc caggaggact ggcccagaga gccctgagat agcggggatc ctgaactgga    1168
ctgaataaaa cgtggtctcc cactgcgcca aaaaaaaaaa a                        1209
```

<210> SEQ ID NO 7
<211> LENGTH: 273
<212> TYPE: PRT
<213> ORGANISM: Homo sapiens

<400> SEQUENCE: 7

```
Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Leu Ser Thr Gly Val Ser Phe Phe Phe Leu Ser
50                  55                  60

Phe His Ile Ser Asn Leu Gln Phe Asn Ser Ser Leu Glu Asp Pro Ser
65                  70                  75                  80

Thr Asp Tyr Tyr Gln Glu Leu Gln Arg Asp Ile Ser Glu Met Phe Leu
                85                  90                  95

Gln Ile Tyr Lys Gln Gly Gly Phe Leu Gly Leu Ser Asn Ile Lys Phe
            100                 105                 110

Arg Pro Gly Ser Val Val Val Gln Leu Thr Leu Ala Phe Arg Glu Gly
        115                 120                 125

Thr Ile Asn Val His Asp Val Glu Thr Gln Phe Asn Gln Tyr Lys Thr
130                 135                 140

Glu Ala Ala Ser Arg Tyr Asn Leu Thr Ile Ser Asp Val Ser Val Ser
145                 150                 155                 160

Asp Val Pro Phe Pro Phe Ser Ala Gln Ser Gly Ala Gly Val Pro Gly
                165                 170                 175

Trp Gly Ile Ala Leu Leu Val Leu Val Cys Val Leu Val Ala Leu Ala
            180                 185                 190

Ile Val Tyr Leu Ile Ala Leu Ala Val Cys Gln Cys Arg Arg Lys Asn
        195                 200                 205

Tyr Gly Gln Leu Asp Ile Phe Pro Ala Arg Asp Thr Tyr His Pro Met
    210                 215                 220

Ser Glu Tyr Pro Thr Tyr His Thr His Gly Arg Tyr Val Pro Pro Ser
225                 230                 235                 240

Ser Thr Asp Arg Ser Pro Tyr Glu Lys Val Ser Ala Gly Asn Gly Gly
                245                 250                 255

Ser Ser Leu Ser Tyr Thr Asn Pro Ala Val Ala Ala Thr Ser Ala Asn
            260                 265                 270

Leu
```

<210> SEQ ID NO 8
<211> LENGTH: 1182
<212> TYPE: DNA
<213> ORGANISM: Homo sapiens
<220> FEATURE:
<221> NAME/KEY: CDS
<222> LOCATION: (67)..(861)

<400> SEQUENCE: 8

```
acctctcaag cagccagcgc ctgcctgaat ctgttctgcc ccctcccac ccatttcacc     60
```

```
accacc atg aca ccg ggc acc cag tct cct ttc ttc ctg ctg ctg ctc         108
       Met Thr Pro Gly Thr Gln Ser Pro Phe Phe Leu Leu Leu Leu
       1               5                   10 ctc aca gtg ctt aca gct acc aca gcc cct aaa ccc gca aca gtt gtt         156
Leu Thr Val Leu Thr Ala Thr Thr Ala Pro Lys Pro Ala Thr Val Val
15              20                  25                  30 acg ggt tct ggt cat gca agc tct acc cca ggt gga gaa aag gag act         204
Thr Gly Ser Gly His Ala Ser Ser Thr Pro Gly Gly Glu Lys Glu Thr
                35                  40                  45 tcg gct acc cag aga agt tca gtg ccc agc tct act gag aag aat gct         252
Ser Ala Thr Gln Arg Ser Ser Val Pro Ser Ser Thr Glu Lys Asn Ala
            50                  55                  60 ttt aat tcc tct ctg gaa gat ccc agc acc gac tac tac caa gag ctg         300
Phe Asn Ser Ser Leu Glu Asp Pro Ser Thr Asp Tyr Tyr Gln Glu Leu
        65                  70                  75 cag aga gac att tct gaa atg ttt ttg cag att tat aaa caa ggg ggt         348
Gln Arg Asp Ile Ser Glu Met Phe Leu Gln Ile Tyr Lys Gln Gly Gly
    80                  85                  90 ttt ctg ggc ctc tcc aat att aag ttc agg cca gga tct gtg gtg gta         396
Phe Leu Gly Leu Ser Asn Ile Lys Phe Arg Pro Gly Ser Val Val Val
95              100                 105                 110 caa ttg act ctg gcc ttc cga gaa ggt acc atc aat gtc cac gac gtg         444
Gln Leu Thr Leu Ala Phe Arg Glu Gly Thr Ile Asn Val His Asp Val
                115                 120                 125 gag aca cag ttc aat cag tat aaa acg gaa gca gcc tct cga tat aac         492
Glu Thr Gln Phe Asn Gln Tyr Lys Thr Glu Ala Ala Ser Arg Tyr Asn
            130                 135                 140 ctg acg atc tca gac gtc agc gtg agt gat gtg cca ttt cct ttc tct         540
Leu Thr Ile Ser Asp Val Ser Val Ser Asp Val Pro Phe Pro Phe Ser
        145                 150                 155 gcc cag tct ggg gct ggg gtg cca ggc tgg ggc atc gcg ctg ctg gtg         588
Ala Gln Ser Gly Ala Gly Val Pro Gly Trp Gly Ile Ala Leu Leu Val
    160                 165                 170 ctg gtc tgt gtt ctg gtt gcg ctg gcc att gtc tat ctc att gcc ttg         636
Leu Val Cys Val Leu Val Ala Leu Ala Ile Val Tyr Leu Ile Ala Leu
175                 180                 185                 190 gct gtc tgt cag tgc cgc cga aag aac tac ggg cag ctg gac atc ttt         684
Ala Val Cys Gln Cys Arg Arg Lys Asn Tyr Gly Gln Leu Asp Ile Phe
                195                 200                 205 cca gcc cgg gat acc tac cat cct atg agc gag tac ccc acc tac cac         732
Pro Ala Arg Asp Thr Tyr His Pro Met Ser Glu Tyr Pro Thr Tyr His
            210                 215                 220 acc cat ggg cgc tat gtg ccc cct agc agt acc gat cgt agc ccc tat         780
Thr His Gly Arg Tyr Val Pro Pro Ser Ser Thr Asp Arg Ser Pro Tyr
        225                 230                 235 gag aag gtt tct gca ggt aat ggt ggc agc agc ctc tct tac aca aac         828
Glu Lys Val Ser Ala Gly Asn Gly Gly Ser Ser Leu Ser Tyr Thr Asn
    240                 245                 250 cca gca gtg gca gcc act tct gcc aac ttg tag gggcacgtcg cccgctgagc       881
Pro Ala Val Ala Ala Thr Ser Ala Asn Leu
255                 260 tgagtggcca gccagtgcca ttccactcca ctcaggttct tcagggccag agccctgca        941 ccctgtttgg gctggtgagc tgggagttca ggtgggctgc tcacagcctc cttcagaggc      1001
cccaccaatt tctcggacac ttctcagtgt gtggaagctc atgtgggccc ctgagggctc      1061
atgcctggga agtgttgtgg tgggggctcc caggaggact ggcccagaga gccctgagat      1121
agcggggatc ctgaactgga ctgaataaaa cgtggtctcc cactgcgcca aaaaaaaaaa      1181
``` a                                                              1182

<210> SEQ ID NO 9
<211> LENGTH: 264
<212> TYPE: PRT
<213> ORGANISM: Homo sapiens

<400> SEQUENCE: 9

Met Thr Pro Gly Thr Gln Ser Pro Phe Phe Leu Leu Leu Leu Leu Thr
1               5                   10                  15

Val Leu Thr Ala Thr Thr Ala Pro Lys Pro Ala Thr Val Val Thr Gly
            20                  25                  30

Ser Gly His Ala Ser Ser Thr Pro Gly Gly Glu Lys Glu Thr Ser Ala
        35                  40                  45

Thr Gln Arg Ser Ser Val Pro Ser Ser Thr Glu Lys Asn Ala Phe Asn
    50                  55                  60

Ser Ser Leu Glu Asp Pro Ser Thr Asp Tyr Tyr Gln Glu Leu Gln Arg
65                  70                  75                  80

Asp Ile Ser Glu Met Phe Leu Gln Ile Tyr Lys Gln Gly Gly Phe Leu
                85                  90                  95

Gly Leu Ser Asn Ile Lys Phe Arg Pro Gly Ser Val Val Val Gln Leu
            100                 105                 110

Thr Leu Ala Phe Arg Glu Gly Thr Ile Asn Val His Asp Val Glu Thr
        115                 120                 125

Gln Phe Asn Gln Tyr Lys Thr Glu Ala Ala Ser Arg Tyr Asn Leu Thr
    130                 135                 140

Ile Ser Asp Val Ser Val Ser Asp Val Pro Phe Pro Phe Ser Ala Gln
145                 150                 155                 160

Ser Gly Ala Gly Val Pro Gly Trp Gly Ile Ala Leu Leu Val Leu Val
                165                 170                 175

Cys Val Leu Val Ala Leu Ala Ile Val Tyr Leu Ile Ala Leu Ala Val
            180                 185                 190

Cys Gln Cys Arg Arg Lys Asn Tyr Gly Gln Leu Asp Ile Phe Pro Ala
        195                 200                 205

Arg Asp Thr Tyr His Pro Met Ser Glu Tyr Pro Thr Tyr His Thr His
    210                 215                 220

Gly Arg Tyr Val Pro Pro Ser Ser Thr Asp Arg Ser Pro Tyr Glu Lys
225                 230                 235                 240

Val Ser Ala Gly Asn Gly Gly Ser Ser Leu Ser Tyr Thr Asn Pro Ala
                245                 250                 255

Val Ala Ala Thr Ser Ala Asn Leu
            260

<210> SEQ ID NO 10
<211> LENGTH: 1032
<212> TYPE: DNA
<213> ORGANISM: Homo sapiens
<220> FEATURE:
<221> NAME/KEY: CDS
<222> LOCATION: (51)..(845)

<400> SEQUENCE: 10
gcgcctgcct gaatctgttc tgccccctcc ccacccattt caccaccacc atg aca      56
                                                         Met Thr
                                                           1 ccg ggc acc cag tct cct ttc ttc ctg ctg ctg ctc aca gtg ctt         104
Pro Gly Thr Gln Ser Pro Phe Phe Leu Leu Leu Leu Thr Val Leu
         5                  10                  15

| | | | | | | | | | | | | | | | |
|---|---|---|---|---|---|---|---|---|---|---|---|---|---|---|---|
| aca | gct | acc | aca | gcc | cct | aaa | ccc | gca | aca | gtt | gtt | aca | ggt | tct | ggt | 152 |
| Thr | Ala | Thr | Thr | Ala | Pro | Lys | Pro | Ala | Thr | Val | Val | Thr | Gly | Ser | Gly |
| | | 20 | | | | 25 | | | | 30 | | | | | | cat gca agc tct acc cca ggt gga gaa aag gag act tcg gct acc cag   200
His Ala Ser Ser Thr Pro Gly Gly Glu Lys Glu Thr Ser Ala Thr Gln
 35              40                  45                  50 aga agt tca gtg ccc agc tct act gag aag aat gct ttt aat tcc tct   248
Arg Ser Ser Val Pro Ser Ser Thr Glu Lys Asn Ala Phe Asn Ser Ser
                 55                  60                  65 ctg gaa gat ccc agc acc gac tac tac caa gag ctg cag aga gac att   296
Leu Glu Asp Pro Ser Thr Asp Tyr Tyr Gln Glu Leu Gln Arg Asp Ile
                 70                  75                  80 tct gaa atg ttt ttg cag att tat aaa caa ggg ggt ttt ctg ggc ctc   344
Ser Glu Met Phe Leu Gln Ile Tyr Lys Gln Gly Gly Phe Leu Gly Leu
             85                  90                  95 tcc aat att aag ttc agg cca gga tct gtg gtg gta caa ttg act ctg   392
Ser Asn Ile Lys Phe Arg Pro Gly Ser Val Val Val Gln Leu Thr Leu
            100                 105                 110 gcc ttc cga gaa ggt acc atc aat gtc cac gac atg gag aca cag ttc   440
Ala Phe Arg Glu Gly Thr Ile Asn Val His Asp Met Glu Thr Gln Phe
115                 120                 125                 130 aat cag tat aaa acg gaa gca gcc tct cga tat aac ctg acg atc tca   488
Asn Gln Tyr Lys Thr Glu Ala Ala Ser Arg Tyr Asn Leu Thr Ile Ser
                135                 140                 145 gac gtc agc gtg agt ggt gtg cca ttt cct ttc tct gcc cag tct ggg   536
Asp Val Ser Val Ser Gly Val Pro Phe Pro Phe Ser Ala Gln Ser Gly
            150                 155                 160 gct ggg gtg cca ggc tgg ggc atc gcg ctg ctg gtg ctg gtc tgt gtt   584
Ala Gly Val Pro Gly Trp Gly Ile Ala Leu Leu Val Leu Val Cys Val
            165                 170                 175 ctg gtt gcg ctg gcc att gtc tat ctc att gcc ttg gct gtc tgt cag   632
Leu Val Ala Leu Ala Ile Val Tyr Leu Ile Ala Leu Ala Val Cys Gln
        180                 185                 190 tgc cgc cga aag aac tac ggg cag ctg gac atc ttt cca gcc cgg gat   680
Cys Arg Arg Lys Asn Tyr Gly Gln Leu Asp Ile Phe Pro Ala Arg Asp
195                 200                 205                 210 acc tac cat cct atg agc gag tac ccc acc tac cac acc cat ggg cgc   728
Thr Tyr His Pro Met Ser Glu Tyr Pro Thr Tyr His Thr His Gly Arg
                215                 220                 225 tat gtg ccc cct agc agt acc gat cgt agc ccc tat gag aag gtt tct   776
Tyr Val Pro Pro Ser Ser Thr Asp Arg Ser Pro Tyr Glu Lys Val Ser
            230                 235                 240 gca ggt aat ggt ggc agc agc ctc tct tac aca aac cca gca gtg gca   824
Ala Gly Asn Gly Gly Ser Ser Leu Ser Tyr Thr Asn Pro Ala Val Ala
        245                 250                 255 gcc act tct gcc aac ttg tag gggcacgtcg cccgctgagc tgagtggcca      875
Ala Thr Ser Ala Asn Leu
        260 gccagtgcca ttccactcca ctcaggttct tcagggccag agcccctgca ccctgtttgg   935 gctggtgagc tgggagttca ggtgggctgc tcacagcctc cttcagaggc cccaccaatt   995 tctcggacac ttctcagtgt gtggaagctc atgtggg                           1032

<210> SEQ ID NO 11
<211> LENGTH: 264
<212> TYPE: PRT
<213> ORGANISM: Homo sapiens

<400> SEQUENCE: 11

Met Thr Pro Gly Thr Gln Ser Pro Phe Phe Leu Leu Leu Leu Thr
1               5                   10                  15

Val Leu Thr Ala Thr Thr Ala Pro Lys Pro Ala Thr Val Val Thr Gly
            20                  25                  30

Ser Gly His Ala Ser Ser Thr Pro Gly Gly Glu Lys Glu Thr Ser Ala
        35                  40                  45

Thr Gln Arg Ser Ser Val Pro Ser Ser Thr Glu Lys Asn Ala Phe Asn
    50                  55                  60

Ser Ser Leu Glu Asp Pro Ser Thr Asp Tyr Tyr Gln Glu Leu Gln Arg
65                  70                  75                  80

Asp Ile Ser Glu Met Phe Leu Gln Ile Tyr Lys Gln Gly Gly Phe Leu
                85                  90                  95

Gly Leu Ser Asn Ile Lys Phe Arg Pro Gly Ser Val Val Gln Leu
            100                 105                 110

Thr Leu Ala Phe Arg Glu Gly Thr Ile Asn Val His Asp Met Glu Thr
        115                 120                 125

Gln Phe Asn Gln Tyr Lys Thr Glu Ala Ala Ser Arg Tyr Asn Leu Thr
    130                 135                 140

Ile Ser Asp Val Ser Val Ser Gly Val Pro Phe Pro Phe Ser Ala Gln
145                 150                 155                 160

Ser Gly Ala Gly Val Pro Gly Trp Gly Ile Ala Leu Leu Val Leu Val
                165                 170                 175

Cys Val Leu Val Ala Leu Ala Ile Val Tyr Leu Ile Ala Leu Ala Val
            180                 185                 190

Cys Gln Cys Arg Arg Lys Asn Tyr Gly Gln Leu Asp Ile Phe Pro Ala
        195                 200                 205

Arg Asp Thr Tyr His Pro Met Ser Glu Tyr Pro Thr Tyr His Thr His
210                 215                 220

Gly Arg Tyr Val Pro Pro Ser Ser Thr Asp Arg Ser Pro Tyr Glu Lys
225                 230                 235                 240

Val Ser Ala Gly Asn Gly Gly Ser Ser Leu Ser Tyr Thr Asn Pro Ala
                245                 250                 255

Val Ala Ala Thr Ser Ala Asn Leu
            260

<210> SEQ ID NO 12
<211> LENGTH: 1166
<212> TYPE: DNA
<213> ORGANISM: Homo sapiens
<220> FEATURE:
<221> NAME/KEY: CDS
<222> LOCATION: (73)..(840)

<400> SEQUENCE: 12
cgctccacct ctcaagcagc cagcgcctgc ctgaatctgt tctgcccct ccccacccat      60 ttcaccacca cc atg aca ccg ggc acc cag tct cct ttc ttc ctg ctg ctg   111
              Met Thr Pro Gly Thr Gln Ser Pro Phe Phe Leu Leu Leu
                1               5                   10 ctc ctc aca gtg ctt aca gtt gtt acg ggt tct ggt cat gca agc tct      159
Leu Leu Thr Val Leu Thr Val Val Thr Gly Ser Gly His Ala Ser Ser
 15                  20                  25 acc cca ggt gga gaa aag gag act tcg gct acc cag aga agt tca gtg      207
Thr Pro Gly Gly Glu Lys Glu Thr Ser Ala Thr Gln Arg Ser Ser Val
 30                  35                  40                  45 ccc agc tct act gag aag aat gct ttt aat tcc tct ctg gaa gat ccc      255
Pro Ser Ser Thr Glu Lys Asn Ala Phe Asn Ser Ser Leu Glu Asp Pro
                 50                  55                  60

```
agc acc gac tac tac caa gag ctg cag aga gac att tct gaa atg ttt     303
Ser Thr Asp Tyr Tyr Gln Glu Leu Gln Arg Asp Ile Ser Glu Met Phe
            65                  70                  75 ttg cag att tat aaa caa ggg ggt ttt ctc ggc ctc tcc aat att aag     351
Leu Gln Ile Tyr Lys Gln Gly Gly Phe Leu Gly Leu Ser Asn Ile Lys
        80                  85                  90 ttc agg cca gga tct gtg gtg gta caa ttg act ctg gcc ttc cga gaa     399
Phe Arg Pro Gly Ser Val Val Val Gln Leu Thr Leu Ala Phe Arg Glu
    95                 100                 105 ggt acc atc aat gtc cac gac gtg gag aca cag ttc aat cag tat aaa     447
Gly Thr Ile Asn Val His Asp Val Glu Thr Gln Phe Asn Gln Tyr Lys
110                 115                 120                 125 acg gaa gca gcc tct cga tat aac ctg acg atc tca gac gtc agc gtg     495
Thr Glu Ala Ala Ser Arg Tyr Asn Leu Thr Ile Ser Asp Val Ser Val
                130                 135                 140 agt gat gtg cca ttt cct ttc tct gcc cag tct ggg gct ggg gtg cca     543
Ser Asp Val Pro Phe Pro Phe Ser Ala Gln Ser Gly Ala Gly Val Pro
            145                 150                 155 ggc tgg ggc atc gcg ctg ctg gtg ctg gtc tgt gtt ctg gtt gcg ctg     591
Gly Trp Gly Ile Ala Leu Leu Val Leu Val Cys Val Leu Val Ala Leu
        160                 165                 170 gcc att gtc tat ctc att gcc ttg gct gtc tgt cag tgc cgc cga aag     639
Ala Ile Val Tyr Leu Ile Ala Leu Ala Val Cys Gln Cys Arg Arg Lys
    175                 180                 185 aac tac ggg cag ctg gac atc ttt cca gcc cgg gat acc tac cat cct     687
Asn Tyr Gly Gln Leu Asp Ile Phe Pro Ala Arg Asp Thr Tyr His Pro
190                 195                 200                 205 atg agc gag tac ccc acc tac cac acc cat ggg cgc tat gtg ccc cct     735
Met Ser Glu Tyr Pro Thr Tyr His Thr His Gly Arg Tyr Val Pro Pro
                210                 215                 220 agc agt acc gat cgt agc ccc tat gag aag gtt tct gca ggt aat ggt     783
Ser Ser Thr Asp Arg Ser Pro Tyr Glu Lys Val Ser Ala Gly Asn Gly
            225                 230                 235 ggc agc agc ctc tct tac aca aac cca gca gtg gca gcc act tct gcc     831
Gly Ser Ser Leu Ser Tyr Thr Asn Pro Ala Val Ala Ala Thr Ser Ala
        240                 245                 250 aac ttg tag gggcacgtcg cccgctgagc tgagtggcca gccagtgcca              880
Asn Leu
    255 ttccactcca ctcaggttct tcagggccag agccctgca ccctgtttgg gctggtgagc    940 tgggagttca ggtgggctgc tcacagcctc cttcagaggc cccaccaatt tctcggacac   1000 ttctcagtgt gtgaagctc atgtgggccc ctgagggctc atgcctggga agtgttgtgg   1060 tgggggctcc caggaggact ggcccagaga gccctgagat agcgggatc ctgaactgga   1120 ctgaataaaa cgtggtctcc cactgcgcca aaaaaaaaaa aaaaaa                  1166

<210> SEQ ID NO 13
<211> LENGTH: 255
<212> TYPE: PRT
<213> ORGANISM: Homo sapiens

<400> SEQUENCE: 13

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45
```

```
Thr Glu Lys Asn Ala Phe Asn Ser Ser Leu Glu Asp Pro Ser Thr Asp
         50                  55                  60

Tyr Tyr Gln Glu Leu Gln Arg Asp Ile Ser Glu Met Phe Leu Gln Ile
 65                  70                  75                  80

Tyr Lys Gln Gly Gly Phe Leu Gly Leu Ser Asn Ile Lys Phe Arg Pro
                 85                  90                  95

Gly Ser Val Val Val Gln Leu Thr Leu Ala Phe Arg Glu Gly Thr Ile
                100                 105                 110

Asn Val His Asp Val Glu Thr Gln Phe Asn Gln Tyr Lys Thr Glu Ala
            115                 120                 125

Ala Ser Arg Tyr Asn Leu Thr Ile Ser Asp Val Ser Val Ser Asp Val
        130                 135                 140

Pro Phe Pro Phe Ser Ala Gln Ser Gly Ala Gly Val Pro Gly Trp Gly
145                 150                 155                 160

Ile Ala Leu Leu Val Leu Val Cys Val Leu Val Ala Leu Ala Ile Val
                165                 170                 175

Tyr Leu Ile Ala Leu Ala Val Cys Gln Cys Arg Arg Lys Asn Tyr Gly
                180                 185                 190

Gln Leu Asp Ile Phe Pro Ala Arg Asp Thr Tyr His Pro Met Ser Glu
            195                 200                 205

Tyr Pro Thr Tyr His Thr His Gly Arg Tyr Val Pro Pro Ser Ser Thr
        210                 215                 220

Asp Arg Ser Pro Tyr Glu Lys Val Ser Ala Gly Asn Gly Gly Ser Ser
225                 230                 235                 240

Leu Ser Tyr Thr Asn Pro Ala Val Ala Ala Thr Ser Ala Asn Leu
                245                 250                 255

<210> SEQ ID NO 14
<211> LENGTH: 475
<212> TYPE: PRT
<213> ORGANISM: Homo sapiens

<400> SEQUENCE: 14

Met Thr Pro Gly Thr Gln Ser Pro Phe Phe Leu Leu Leu Leu Leu Thr
 1               5                  10                  15

Val Leu Thr Val Val Thr Gly Ser Gly His Ala Ser Ser Thr Pro Gly
                20                  25                  30

Gly Glu Lys Glu Thr Ser Ala Thr Gln Arg Ser Ser Val Pro Ser Ser
                35                  40                  45

Thr Glu Lys Asn Ala Val Ser Met Thr Ser Ser Val Leu Ser Ser His
         50                  55                  60

Ser Pro Gly Ser Gly Ser Ser Thr Thr Gln Gly Gln Asp Val Thr Leu
 65                  70                  75                  80

Ala Pro Ala Thr Glu Pro Ala Ser Gly Ser Ala Ala Thr Trp Gly Gln
                 85                  90                  95

Asp Val Thr Ser Val Pro Val Thr Arg Pro Ala Leu Gly Ser Thr Thr
                100                 105                 110

Pro Pro Ala His Asp Val Thr Ser Ala Pro Asp Asn Lys Pro Ala Pro
            115                 120                 125

Gly Ser Thr Ala Pro Pro Ala His Gly Val Thr Ser Ala Pro Asp Thr
        130                 135                 140

Arg Pro Ala Pro Gly Ser Thr Ala Pro Pro Ala His Gly Val Thr Ser
145                 150                 155                 160

Ala Pro Asp Asn Arg Pro Ala Leu Gly Ser Thr Ala Pro Pro Val His
```

```
                    165                 170                 175
Asn Val Thr Ser Ala Ser Gly Ser Ala Ser Gly Ser Ala Ser Thr Leu
                180                 185                 190

Val His Asn Gly Thr Ser Ala Arg Ala Thr Thr Pro Ala Ser Lys
            195                 200                 205

Ser Thr Pro Phe Ser Ile Pro Ser His His Ser Asp Thr Pro Thr Thr
        210                 215                 220

Leu Ala Ser His Ser Thr Lys Thr Asp Ala Ser Ser Thr His His Ser
225                 230                 235                 240

Thr Val Pro Pro Leu Thr Ser Ser Asn His Ser Thr Ser Pro Gln Leu
                245                 250                 255

Ser Thr Gly Val Ser Phe Phe Leu Ser Phe His Ile Ser Asn Leu
            260                 265                 270

Gln Phe Asn Ser Ser Leu Glu Asp Pro Ser Thr Asp Tyr Tyr Gln Glu
        275                 280                 285

Leu Gln Arg Asp Ile Ser Glu Met Phe Leu Gln Ile Tyr Lys Gln Gly
    290                 295                 300

Gly Phe Leu Gly Leu Ser Asn Ile Lys Phe Arg Pro Gly Ser Val Val
305                 310                 315                 320

Val Gln Leu Thr Leu Ala Phe Arg Glu Gly Thr Ile Asn Val His Asp
                325                 330                 335

Val Glu Thr Gln Phe Asn Gln Tyr Lys Thr Glu Ala Ala Ser Arg Tyr
            340                 345                 350

Asn Leu Thr Ile Ser Asp Val Ser Val Ser Asp Val Pro Phe Pro Phe
        355                 360                 365

Ser Ala Gln Ser Gly Ala Gly Val Pro Gly Trp Gly Ile Ala Leu Leu
    370                 375                 380

Val Leu Val Cys Val Leu Val Ala Leu Ala Ile Val Tyr Leu Ile Ala
385                 390                 395                 400

Leu Ala Val Cys Gln Cys Arg Arg Lys Asn Tyr Gly Gln Leu Asp Ile
                405                 410                 415

Phe Pro Ala Arg Asp Thr Tyr His Pro Met Ser Glu Tyr Pro Thr Tyr
            420                 425                 430

His Thr His Gly Arg Tyr Val Pro Pro Ser Ser Thr Asp Arg Ser Pro
        435                 440                 445

Tyr Glu Lys Val Ser Ala Gly Asn Gly Gly Ser Ser Leu Ser Tyr Thr
    450                 455                 460

Asn Pro Ala Val Ala Ala Thr Ser Ala Asn Leu
465                 470                 475

<210> SEQ ID NO 15
<211> LENGTH: 1727
<212> TYPE: DNA
<213> ORGANISM: Artificial Sequence
<220> FEATURE:
<223> OTHER INFORMATION: Synthetic Construct
<220> FEATURE:
<221> NAME/KEY: CDS
<222> LOCATION: (1)..(1719)

<400> SEQUENCE: 15 atg aga ttt cct tca att ttt act gca gtt tta ttc gca gca tcc tcc     48
Met Arg Phe Pro Ser Ile Phe Thr Ala Val Leu Phe Ala Ala Ser Ser
1               5                   10                  15 gca tca gct gct cca gtc aac act aca aca gaa gat gaa acg gca caa     96
Ala Ser Ala Ala Pro Val Asn Thr Thr Thr Glu Asp Glu Thr Ala Gln
            20                  25                  30
```

| | | | | | | | | | | | | | | | | |
|---|---|---|---|---|---|---|---|---|---|---|---|---|---|---|---|---|
| att | ccg | gct | gaa | gct | gtc | atc | ggt | tac | tta | gat | tta | gaa | ggg | gat | ttc | 144 |
| Ile | Pro | Ala | Glu | Ala | Val | Ile | Gly | Tyr | Leu | Asp | Leu | Glu | Gly | Asp | Phe | |
| | | 35 | | | | | 40 | | | | | 45 | | | | |
| gat | gtt | gct | gtt | ttg | cca | ttt | tcc | aac | agc | aca | aat | aac | ggg | tta | ttg | 192 |
| Asp | Val | Ala | Val | Leu | Pro | Phe | Ser | Asn | Ser | Thr | Asn | Asn | Gly | Leu | Leu | |
| | 50 | | | | | 55 | | | | | 60 | | | | | |
| ttt | ata | aat | act | act | att | gcc | agc | att | gct | gct | aaa | gaa | gaa | ggg | gta | 240 |
| Phe | Ile | Asn | Thr | Thr | Ile | Ala | Ser | Ile | Ala | Ala | Lys | Glu | Glu | Gly | Val | |
| 65 | | | | | 70 | | | | | 75 | | | | | 80 | |
| tct | cta | gat | aaa | aga | gag | gct | gaa | gct | act | agt | atg | act | cca | ggt | aca | 288 |
| Ser | Leu | Asp | Lys | Arg | Glu | Ala | Glu | Ala | Thr | Ser | Met | Thr | Pro | Gly | Thr | |
| | | | | 85 | | | | | 90 | | | | | 95 | | |
| caa | tca | cca | ttc | ttt | ttg | ttg | cta | ttg | tta | acc | gtt | ctg | acc | gtc | gtt | 336 |
| Gln | Ser | Pro | Phe | Phe | Leu | Leu | Leu | Leu | Leu | Thr | Val | Leu | Thr | Val | Val | |
| | | | 100 | | | | | 105 | | | | | 110 | | | |
| act | gga | tca | ggt | cac | gcc | tct | agt | acg | cca | gga | ggt | gaa | aaa | gag | act | 384 |
| Thr | Gly | Ser | Gly | His | Ala | Ser | Ser | Thr | Pro | Gly | Gly | Glu | Lys | Glu | Thr | |
| | | | 115 | | | | | 120 | | | | | 125 | | | |
| tct | gcc | aca | caa | aga | tcc | tct | gtc | cca | tca | tct | act | gag | aaa | aat | gca | 432 |
| Ser | Ala | Thr | Gln | Arg | Ser | Ser | Val | Pro | Ser | Ser | Thr | Glu | Lys | Asn | Ala | |
| | | 130 | | | | | 135 | | | | | 140 | | | | |
| gtt | tct | atg | aca | tcc | tca | gta | ttg | tcc | tca | cat | tcc | cct | ggt | tct | ggt | 480 |
| Val | Ser | Met | Thr | Ser | Ser | Val | Leu | Ser | Ser | His | Ser | Pro | Gly | Ser | Gly | |
| 145 | | | | | 150 | | | | | 155 | | | | | 160 | |
| tcc | tct | aca | act | cag | gga | caa | gat | gtg | acg | ttg | gct | cct | gca | acc | gaa | 528 |
| Ser | Ser | Thr | Thr | Gln | Gly | Gln | Asp | Val | Thr | Leu | Ala | Pro | Ala | Thr | Glu | |
| | | | | 165 | | | | | 170 | | | | | 175 | | |
| cca | gcc | tcc | ggg | agt | gcg | gct | cta | tgg | ggg | caa | gat | gtc | aca | tca | gtc | 576 |
| Pro | Ala | Ser | Gly | Ser | Ala | Ala | Leu | Trp | Gly | Gln | Asp | Val | Thr | Ser | Val | |
| | | | 180 | | | | | 185 | | | | | 190 | | | |
| cca | gta | aca | aga | cct | gca | tta | gga | tca | aca | act | cct | gct | cac | gat | | 624 |
| Pro | Val | Thr | Arg | Pro | Ala | Leu | Gly | Ser | Thr | Thr | Pro | Ala | His | Asp | | |
| | | 195 | | | | | 200 | | | | | 205 | | | | |
| gta | aca | agc | gca | cca | gat | aac | aag | cct | gca | cct | ggc | tct | acc | gct | cca | 672 |
| Val | Thr | Ser | Ala | Pro | Asp | Asn | Lys | Pro | Ala | Pro | Gly | Ser | Thr | Ala | Pro | |
| 210 | | | | | 215 | | | | | 220 | | | | | | |
| cct | gcc | cac | ggc | gta | aca | agt | tat | ttg | gat | aca | aga | cca | gca | cct | gtt | 720 |
| Pro | Ala | His | Gly | Val | Thr | Ser | Tyr | Leu | Asp | Thr | Arg | Pro | Ala | Pro | Val | |
| 225 | | | | 230 | | | | | 235 | | | | | 240 | | |
| tac | ttg | gca | cct | cct | gct | cac | ggt | gtt | aca | tct | gct | cct | gac | aat | aga | 768 |
| Tyr | Leu | Ala | Pro | Pro | Ala | His | Gly | Val | Thr | Ser | Ala | Pro | Asp | Asn | Arg | |
| | | | | 245 | | | | | 250 | | | | | 255 | | |
| cca | gct | tta | gga | tct | act | gct | cct | cca | gtg | cat | aac | gta | act | tca | gcc | 816 |
| Pro | Ala | Leu | Gly | Ser | Thr | Ala | Pro | Pro | Val | His | Asn | Val | Thr | Ser | Ala | |
| | | | 260 | | | | | 265 | | | | | 270 | | | |
| tca | ggc | tcc | gca | tcc | ggt | tct | gct | tca | aca | ctt | gtc | cac | aat | gga | act | 864 |
| Ser | Gly | Ser | Ala | Ser | Gly | Ser | Ala | Ser | Thr | Leu | Val | His | Asn | Gly | Thr | |
| | | | 275 | | | | | 280 | | | | | 285 | | | |
| tct | gct | aga | gca | aca | aca | aca | cca | gcc | tct | aaa | agt | act | cct | ttc | tct | 912 |
| Ser | Ala | Arg | Ala | Thr | Thr | Thr | Pro | Ala | Ser | Lys | Ser | Thr | Pro | Phe | Ser | |
| | | 290 | | | | | 295 | | | | | 300 | | | | |
| atc | cca | tct | cat | cat | tct | gat | act | cct | aca | act | tta | gct | tca | cac | tca | 960 |
| Ile | Pro | Ser | His | His | Ser | Asp | Thr | Pro | Thr | Thr | Leu | Ala | Ser | His | Ser | |
| 305 | | | | | 310 | | | | | 315 | | | | | 320 | |
| act | aaa | aca | gat | gcc | agt | agt | act | cat | cat | tcc | tct | gta | cca | cct | ctt | 1008 |
| Thr | Lys | Thr | Asp | Ala | Ser | Ser | Thr | His | His | Ser | Ser | Val | Pro | Pro | Leu | |
| | | | | 325 | | | | | 330 | | | | | 335 | | |
| aca | tct | tct | aat | cat | tca | aca | tca | cca | caa | ctc | tcc | act | ggt | gtg | agc | 1056 |
| Thr | Ser | Ser | Asn | His | Ser | Thr | Ser | Pro | Gln | Leu | Ser | Thr | Gly | Val | Ser | |

```
                340                 345                 350
ttc ttc ttc ctc tct ttt cac att tca aac ctg caa ttc aac tct tcc    1104
Phe Phe Phe Leu Ser Phe His Ile Ser Asn Leu Gln Phe Asn Ser Ser
            355                 360                 365 cta gag gac cca tct acg gac tat tat caa gag ttg caa aga gat atc    1152
Leu Glu Asp Pro Ser Thr Asp Tyr Tyr Gln Glu Leu Gln Arg Asp Ile
370                 375                 380 agc gaa atg ttt cta cag atc tac aag caa ggt gga ttt ttg gga cta    1200
Ser Glu Met Phe Leu Gln Ile Tyr Lys Gln Gly Gly Phe Leu Gly Leu
385                 390                 395                 400 tca aac ata aag ttt aga cca ggc agc gtt gtc gtc caa ctt acc tta    1248
Ser Asn Ile Lys Phe Arg Pro Gly Ser Val Val Val Gln Leu Thr Leu
                405                 410                 415 gct ttt aga gaa ggg act att aat gtt cat gat gtg gaa acc cag ttt    1296
Ala Phe Arg Glu Gly Thr Ile Asn Val His Asp Val Glu Thr Gln Phe
            420                 425                 430 aat caa tac aag aca gaa gca gct tca cga tac aat ttg aca att tcc    1344
Asn Gln Tyr Lys Thr Glu Ala Ala Ser Arg Tyr Asn Leu Thr Ile Ser
        435                 440                 445 gat gtt tct gtt tcc gac gta cct ttt cca ttc tct gcc caa agt ggt    1392
Asp Val Ser Val Ser Asp Val Pro Phe Pro Phe Ser Ala Gln Ser Gly
450                 455                 460 gcg ggt gtt cca ggt tgg ggg att gct ctg tta gtg tta gtc tgt gtt    1440
Ala Gly Val Pro Gly Trp Gly Ile Ala Leu Leu Val Leu Val Cys Val
465                 470                 475                 480 ctc gtt tac tta gct atc gta tac tta ata gcc cta gca gtt gcc cag    1488
Leu Val Tyr Leu Ala Ile Val Tyr Leu Ile Ala Leu Ala Val Ala Gln
                485                 490                 495 gtg aga agg aaa aac tat ggc caa ttg gat atc ttt cct gct aga gac    1536
Val Arg Arg Lys Asn Tyr Gly Gln Leu Asp Ile Phe Pro Ala Arg Asp
            500                 505                 510 aag tac cat cca atg tct gaa tat gcc ctc tac cat aca cat ggt agg    1584
Lys Tyr His Pro Met Ser Glu Tyr Ala Leu Tyr His Thr His Gly Arg
        515                 520                 525 tac gtg cca cca tca agt ctt ttt cgt tca cca tac gaa aaa gtt agc    1632
Tyr Val Pro Pro Ser Ser Leu Phe Arg Ser Pro Tyr Glu Lys Val Ser
530                 535                 540 gca ggt aat ggc ggc agt tac ctg tca tac act aac cca gcg gtt gct    1680
Ala Gly Asn Gly Gly Ser Tyr Leu Ser Tyr Thr Asn Pro Ala Val Ala
545                 550                 555                 560 gcg gct agt gcc aat ctt cat cac cat cat cac cat taa gcggccgc       1727
Ala Ala Ser Ala Asn Leu His His His His His His
                565                 570

<210> SEQ ID NO 16
<211> LENGTH: 572
<212> TYPE: PRT
<213> ORGANISM: Artificial Sequence
<220> FEATURE:
<223> OTHER INFORMATION: Synthetic Construct

<400> SEQUENCE: 16

Met Arg Phe Pro Ser Ile Phe Thr Ala Val Leu Phe Ala Ala Ser Ser
1               5                   10                  15

Ala Ser Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60
```

-continued

```
Phe Ile Asn Thr Thr Ile Ala Ser Ile Ala Ala Lys Glu Glu Gly Val
 65                  70                  75                  80

Ser Leu Asp Lys Arg Glu Ala Glu Ala Thr Ser Met Thr Pro Gly Thr
                 85                  90                  95

Gln Ser Pro Phe Phe Leu Leu Leu Leu Thr Val Leu Thr Val Val
            100                 105                 110

Thr Gly Ser Gly His Ala Ser Ser Thr Pro Gly Gly Glu Lys Glu Thr
            115                 120                 125

Ser Ala Thr Gln Arg Ser Ser Val Pro Ser Ser Thr Glu Lys Asn Ala
130                 135                 140

Val Ser Met Thr Ser Ser Val Leu Ser Ser His Ser Pro Gly Ser Gly
145                 150                 155                 160

Ser Ser Thr Thr Gln Gly Gln Asp Val Thr Leu Ala Pro Ala Thr Glu
                165                 170                 175

Pro Ala Ser Gly Ser Ala Ala Leu Trp Gly Gln Asp Val Thr Ser Val
            180                 185                 190

Pro Val Thr Arg Pro Ala Leu Gly Ser Thr Thr Pro Pro Ala His Asp
            195                 200                 205

Val Thr Ser Ala Pro Asp Asn Lys Pro Ala Pro Gly Ser Thr Ala Pro
210                 215                 220

Pro Ala His Gly Val Thr Ser Tyr Leu Asp Thr Arg Pro Ala Pro Val
225                 230                 235                 240

Tyr Leu Ala Pro Pro Ala His Gly Val Thr Ser Ala Pro Asp Asn Arg
                245                 250                 255

Pro Ala Leu Gly Ser Thr Ala Pro Pro Val His Asn Val Thr Ser Ala
            260                 265                 270

Ser Gly Ser Ala Ser Gly Ser Ala Ser Thr Leu Val His Asn Gly Thr
            275                 280                 285

Ser Ala Arg Ala Thr Thr Thr Pro Ala Ser Lys Ser Thr Pro Phe Ser
290                 295                 300

Ile Pro Ser His His Ser Asp Thr Pro Thr Thr Leu Ala Ser His Ser
305                 310                 315                 320

Thr Lys Thr Asp Ala Ser Ser Thr His His Ser Ser Val Pro Pro Leu
                325                 330                 335

Thr Ser Ser Asn His Ser Thr Ser Pro Gln Leu Ser Thr Gly Val Ser
            340                 345                 350

Phe Phe Phe Leu Ser Phe His Ile Ser Asn Leu Gln Phe Asn Ser Ser
            355                 360                 365

Leu Glu Asp Pro Ser Thr Asp Tyr Tyr Gln Glu Leu Gln Arg Asp Ile
            370                 375                 380

Ser Glu Met Phe Leu Gln Ile Tyr Lys Gln Gly Gly Phe Leu Gly Leu
385                 390                 395                 400

Ser Asn Ile Lys Phe Arg Pro Gly Ser Val Val Val Gln Leu Thr Leu
                405                 410                 415

Ala Phe Arg Glu Gly Thr Ile Asn Val His Asp Val Glu Thr Gln Phe
            420                 425                 430

Asn Gln Tyr Lys Thr Glu Ala Ala Ser Arg Tyr Asn Leu Thr Ile Ser
            435                 440                 445

Asp Val Ser Val Ser Asp Val Pro Phe Pro Phe Ser Ala Gln Ser Gly
            450                 455                 460

Ala Gly Val Pro Gly Trp Gly Ile Ala Leu Leu Val Leu Val Cys Val
465                 470                 475                 480
```

```
Leu Val Tyr Leu Ala Ile Val Tyr Leu Ile Ala Leu Ala Val Ala Gln
            485                 490                 495

Val Arg Arg Lys Asn Tyr Gly Gln Leu Asp Ile Phe Pro Ala Arg Asp
        500                 505                 510

Lys Tyr His Pro Met Ser Glu Tyr Ala Leu Tyr His Thr His Gly Arg
            515                 520                 525

Tyr Val Pro Pro Ser Ser Leu Phe Arg Ser Pro Tyr Glu Lys Val Ser
        530                 535                 540

Ala Gly Asn Gly Gly Ser Tyr Leu Ser Tyr Thr Asn Pro Ala Val Ala
545                 550                 555                 560

Ala Ala Ser Ala Asn Leu His His His His His His
            565                 570

<210> SEQ ID NO 17
<211> LENGTH: 89
<212> TYPE: PRT
<213> ORGANISM: Saccharomyces cerevisiae

<400> SEQUENCE: 17

Met Arg Phe Pro Ser Ile Phe Thr Ala Val Leu Phe Ala Ala Ser Ser
1               5                   10                  15

Ala Ser Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala
                85

<210> SEQ ID NO 18
<211> LENGTH: 89
<212> TYPE: PRT
<213> ORGANISM: Saccharomyces cerevisiae

<400> SEQUENCE: 18

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala
                85

<210> SEQ ID NO 19
<211> LENGTH: 6
<212> TYPE: PRT
```

```
<213> ORGANISM: Artificial Sequence
<220> FEATURE:
<223> OTHER INFORMATION: Synthetic peptide

<400> SEQUENCE: 19

Met Ala Asp Glu Ala Pro
1               5
```

HLA-A24 AGONIST EPITOPES OF MUC1-C ONCOPROTEIN AND COMPOSITIONS AND METHODS OF USE

CROSS-REFERENCE TO RELATED APPLICATIONS

This patent application is a divisional application of U.S. Ser. No. 16/715,038, filed Dec. 16, 2019, which is a is a divisional application of U.S. Ser. No. 16/034,654, filed Jul. 13, 2018, now U.S. Pat. No. 10,508,141, which is a divisional application of U.S. Ser. No. 15/031,435, filed Apr. 22, 2016, now U.S. Pat. No. 10,035,832, which is the U.S. national phase of PCT/US2014/061723, filed Oct. 22, 2014, which claims the benefit of U.S. Provisional Patent Application No. 61/894,482, filed Oct. 23, 2013, all of which are incorporated herein by reference.

REFERENCE TO SEQUENCE LISTING

This application contains a Sequence Listing submitted electronically as a text file by EFS-Web. The text file, named "723806_ST25", has a size in bytes of 58,000 Bytes, and was recorded on Apr. 22, 2016. The information contained in the text file is incorporated herein by reference in its entirety pursuant to 37 CFR § 1.52(e)(5)

BACKGROUND OF THE INVENTION

MUC1 (CD227) is a type I membrane glycoprotein composed of heterodimers of a large N-terminal subunit (MUC1-N) covalently bound to a small C-terminal subunit (MUC1-C).

The N-terminal subunit (MUC1-N) is the large extracellular domain, which consists of the variable number of tandem repeats region (VNTR) and the non-VNTR region. MUC1-N is shed from the cells and can be found in the circulation of patients with advanced cancer. MUC1-N is used as a tumor marker (CA15.3) in breast cancer patients (see Hayes et al., *J. Clin. Oncol.*, 4: 1542-50 (1986)).

The C-terminal region of MUC1 (MUC1-C) has three distinctive parts: a small extracellular domain that is covalently bound to MUC1-N, a single transmembrane domain, and a cytoplasmic tail (see Lan et al., *J. Biol. Chem.*, 265: 15294-9 (1990)). The cytoplasmic tail contains sites for interaction with signaling proteins, such as β-catenin, epidermal growth factor receptor (EGFR), and Src (see Li et al., *J. Biol. Chem.*, 276: 35239-42 (2001)). Since these proteins are situated at the basolateral part of healthy cells, protein-MUC1 interactions are not believed to be significant. However, loss of polarity in human tumor cells allows the cytoplasmic tail to be exposed to the signaling proteins, and interaction can occur (see Vermeer et al., *Nature*, 422: 322-6 (2003)).

The MUC1-C region has been shown to act as an oncogene, leading to transformation of human cells when MUC1-C binds to β-catenin (see Li et al., *Oncogene*, 22: 6107-10 (2003); Raina et al., *Cancer Res.*, 69: 5133-41 (2009); and Wei et al., *Cancer Res.*, 67: 1853-8 (2007)). Moreover, MUC1-C transfection has been demonstrated to be sufficient to induce transformation and confer oncogenic activities previously attributed to the full-length MUC1 protein, such as increased growth rate, anchorage-independent cell growth, and resistance to chemotherapy agents (see Ren et al., *Cancer Cell.* 5: 163-75 (2004)). In addition, MUC1-C signaling activated by c-Src is involved in the disruption of both E-cadherin adherens junctions and integrin focal adhesions that stimulate cancer cell motility, invasion, and metastasis, thereby suggesting a possible role for MUC1-C in epithelial to mesenchymal transition (EMT) (see Hu et al., *Expert Rev. Anticancer Ther.*, 6: 1261-71 (2006)). Overexpression of genes related to MUC1 has also been found to be highly associated with poor prognosis in patients with lung and breast cancer and with drug resistance (see Ren et al., supra; and Khodarev et al., *Cancer Res.*, 69: 2833-7 (2009)).

Numerous clinical trials have evaluated MUC1 as a potential target for vaccine therapy of a range of human tumors. The majority of these have employed polypeptides of the VNTR region. One agonist epitope (P93L) was shown, compared to the native epitope, to enhance the generation of T cells that can also more efficiently lyse human tumor cells (see Tsang et al., *Cancer Res.*, 10: 2139-49 (2004)). Two other potential agonist epitopes in this region were shown to enhance T-cell cytokine production, but no tumor cell killing was reported (see Mitchell et al., *Cancer Immunol. Immunother.*, 56: 287-301 (2007)).

One method that has been shown to enhance the ability of a vaccine to be more efficacious is to make alterations in the amino acid sequence of putative T-cell epitopes, which in turn can enhance T-cell activation and specific T-cell killing of tumor cells (see Grey et al., *Cancer Surv.*, 22: 37-49 (1995); and Terasawa et al., *Clin. Cancer Res.* 8: 41-53 (2002)). Not all substitutions of an amino acid of a potential cytotoxic T lymphocyte (CTL) epitope, however, will lead to an enhancer agonist epitope, and some substitutions will lead to antagonist epitopes. Moreover, the generation of a putative agonist epitope of a tumor associated antigen may well lead to enhanced T-cell activation by IFN-γ production, but will be useless unless the activated T cell will recognize the endogenous (native) epitope expressed in the context of the MHC on the surface of human tumor cells, and consequently lyse those tumor cells.

There is a desire to identify new specific cytotoxic T lymphocyte (CTL) epitopes and enhancer agonist peptides or epitopes of MUC1-C, and to develop compositions and methods that use these epitopes for the diagnosis and/or treatment of cancer.

BRIEF SUMMARY OF THE INVENTION

The invention provides a peptide comprising the amino acid sequence of SEQ ID NO: 1 or SEQ ID NO: 2.

In another aspect, the invention provides a polypeptide (protein) comprising the peptide, a nucleic acid encoding the peptide, a vector comprising the nucleic acid, a cell comprising the peptide, polypeptide (protein), nucleic acid, or vector, and compositions thereof.

In particular, the invention provides a MUC1 protein or polypeptide comprising the amino acid sequence of SEQ ID NO: 1 or SEQ ID NO: 2 (e.g., SEQ ID NO: 16).

In another aspect, the invention provides a yeast-MUC1 immunotherapeutic composition comprising (a) a yeast vehicle and (b) a fusion protein comprising at least one MUC1 antigen, wherein the MUC1 antigen comprises the amino acid sequence of SEQ ID NO: 1 or SEQ ID NO: 2.

The invention also provides a yeast-MUC1 immunotherapeutic composition comprising (a) a yeast vehicle and (b) a fusion protein comprising at least one MUC1 antigen, wherein the MUC1 antigen comprises an amino acid sequence that is at least 80% identical to (i) SEQ ID NO: 16, (ii) positions 92-566 of SEQ ID NO: 16, or (iii) a corresponding sequence from a different MUC1 protein, and wherein the MUC1 antigen comprises the amino acid sequence of SEQ ID NO: 1 or SEQ ID NO: 2.

The invention also provides a yeast-MUC1 immunotherapeutic composition comprising (a) a yeast vehicle and (b) a fusion protein comprising at least one MUC1 antigen, wherein the MUC1 antigen comprises an amino acid sequence that differs from an amino acid sequence of a wild-type MUC1 protein by at least one amino acid substitution at a sequence position, with respect to a wild-type MUC1 amino acid sequence such as SEQ ID NO: 14, that is selected from: T422, P430, T431, 5462, and A470.

The invention also provides a method of enhancing an immune response against a MUC1-expressing cancer in a host comprising administering a therapeutically effective amount of a composition comprising the peptide, protein, polynucleotide, nucleic acid, vector, cell, or yeast-MUC1 immunotherapeutic composition to the host, wherein the immune response in the host is enhanced.

The invention also provides a method of treating a MUC1-expressing cancer in an individual comprising administering a therapeutically effective amount of a composition comprising the peptide, polypeptide (protein), nucleic acid, vector, cell, or yeast-MUC1 immunotherapeutic composition to the individual.

The invention also provides a method of reducing, arresting, reversing or preventing the metastatic progression of cancer in an individual who has a MUC1-expressing cancer comprising administering a therapeutically effective amount of a composition comprising the peptide, polypeptide (protein), nucleic acid, vector, cell, or yeast-MUC1 immunotherapeutic composition to the individual.

The invention also provides a method of preventing or delaying the onset of a MUC1-expressing cancer in an individual comprising administering a therapeutically effective amount of a composition comprising the peptide, polypeptide (protein), nucleic acid, vector, cell, or yeast-MUC1 immunotherapeutic composition to the individual.

The invention further provides a method of inhibiting a MUC1-expressing cancer in a subject comprising (a) obtaining (isolating) lymphocytes from the subject, (b) stimulating the lymphocytes with a composition comprising the peptide, polypeptide (protein), nucleic acid, vector, or cell to the host to generate cytotoxic T lymphocytes ex vivo, and (c) administering the cytotoxic T lymphocytes to the subject, wherein the MUC1-expressing cancer in the subject is inhibited.

The invention provides a method of inhibiting a MUC1-expressing cancer in a subject comprising (a) obtaining (isolating) dendritic cells from the subject, (b) treating the dendritic cells with a composition comprising the peptide, polypeptide (protein), nucleic acid, vector, cell, or yeast-MUC1 immunotherapeutic composition ex vivo, and (c) administering the treated dendritic cells to the subject, wherein the MUC1-expressing cancer in the subject is inhibited.

Additionally, the invention provides inhibiting a MUC1-expressing cancer in a subject comprising (a) obtaining peripheral blood mononuclear cells (PBMCs) from a subject suffering from cancer, (b) isolating dendritic cells from the PBMCs, (c) treating the dendritic cells with a composition comprising the peptide, polypeptide (protein), nucleic acid, vector, cell, or yeast-MUC1 immunotherapeutic composition ex vivo, (d) activating the PBMCs with the treated dendritic cells ex vivo, and (e) administering the activated PBMCs to the subject, wherein the MUC1-expressing cancer in the subject is inhibited.

The invention further provides inhibiting a MUC1-expressing cancer in a subject comprising (a) obtaining peripheral blood mononuclear cells (PBMCs) from a subject suffering from cancer, (b) isolating dendritic cells from the PBMCs, (c) treating the dendritic cells with a composition comprising the peptide, polypeptide (protein), nucleic acid, vector, cell or yeast-MUC1 immunotherapeutic composition ex vivo, (d) activating the PBMCs with the treated dendritic cells ex vivo, (e) isolating T lymphocytes from the activated PBMCs ex vivo, and (f) administering the isolated T lymphocytes to the subject, wherein the MUC1-expressing cancer in the subject is inhibited.

The invention provides the use of adoptively transferred T cells stimulated in vitro with a composition comprising the peptide, polypeptide (protein), nucleic acid, vector, cell, or yeast-MUC1 immunotherapeutic composition to treat a cancer, to inhibit a MUC1-expressing cancer in a subject, to reduce, arrest, reverse, or prevent the metastatic progression of cancer in an individual that has cancer, or to prevent or delay the onset of a MUC1-expressing cancer.

In an additional aspect, the invention provides a method of inducing an immune response against a MUC1-expressing cancer in a subject comprising (a) administering to the subject a first poxviral vector comprising a nucleic acid encoding the amino acid sequence of SEQ ID NO: 1 or SEQ ID NO: 2 and (b) administering to the subject a second poxviral vector comprising a nucleic acid encoding the amino acid sequence of SEQ ID NO: 1 or SEQ ID NO: 2. In one embodiment, the nucleic acid encoding the amino acid sequence of SEQ ID NO: 1 or SEQ ID NO: 2 is a nucleic acid encoding a MUC1 protein comprising the amino acid sequence of SEQ ID NO: 1 or SEQ ID NO: 2 (e.g., SEQ ID NO: 16).

DETAILED DESCRIPTION OF THE INVENTION

The invention provides peptides comprising a human cytotoxic T lymphocyte (CTL) epitope from the C-terminal subunit of human tumor-associated antigen (TAA) mucin 1 (MUC1) and analogs thereof, which can be used in vaccines and other compositions for the prevention or therapeutic treatment of cancer, including, but not limited to, a cancer that expresses or overexpresses MUC1. In particular, the invention provides peptides, polypeptides, and proteins comprising, consisting essentially of, or consisting of the amino acid sequence of KYHPMSEYAL (SEQ ID NO: 1) or KYTNPAVAL (SEQ ID NO: 2).

In another embodiment, the invention provides a polypeptide that comprises the MUC1 amino acid sequence (i.e., a MUC1 protein) or fragment thereof, wherein one or more of the corresponding amino acid residues have been replaced with one or more of the enhancer agonist epitopes SEQ ID NO: 1 or SEQ ID NO: 2 (e.g., SEQ ID NO: 16).

A "polypeptide" is generally understood to be a linear organic polymer consisting of a large number of amino acid residues bonded together in a continuous, unbranched chain, forming part of, or the whole of, a protein molecule. A "peptide" is generally considered to be distinguished from a full-length protein or polypeptide on the basis of size, and, in one embodiment, as an arbitrary benchmark can be understood to contain approximately 50 or fewer amino acids, while polypeptides or full-length proteins are generally longer. However, the terms "peptide" and "polypeptide" can be used interchangeably in some embodiments to describe a protein useful in the present invention, or the term "protein" can be used generally.

The inventive peptide or polypeptide can be any suitable length. In one embodiment, a peptide of the invention has no more than 20 (e.g., no more than 19, no more than 18, no more than 17, no more than 16, no more than 15, no more than 14, no more than 13, no more than 12, no more than 11, or no more than 10) amino acid residues. The additional amino acid residues, if present, preferably are from the MUC1 (e.g., MUC1-C) protein or based on the sequence of MUC1 as described herein. The additional amino acid residues can be positioned at either end or both ends of the amino acid sequence of SEQ ID NO: 1 or SEQ ID NO: 2.

A polypeptide for expression in a host cell, such as a yeast, is of a minimum size capable of being expressed recombinantly in the host cell. Accordingly, the polypeptide that is expressed by the host cell is preferably at least 25 amino acids in length, and is typically at least or greater than 25 amino acids in length, or at least or greater than 26 amino acids, at least or greater than 27 amino acids, at least or greater than 28 amino acids, at least or greater than 29 amino acids, at least or greater than 30 amino acids, at least or greater than 31 amino acids, at least or greater than 32 amino acids, at least or greater than 33 amino acids, at least or greater than 34 amino acids, at least or greater than 35 amino acids, at least or greater than 36 amino acids, at least or greater than 37 amino acids, at least or greater than 38 amino acids, at least or greater than 39 amino acids, at least or greater than 40 amino acids, at least or greater than 41 amino acids, at least or greater than 42 amino acids, at least or greater than 43 amino acids, at least or greater than 44 amino acids, at least or greater than 45 amino acids, at least or greater than 46 amino acids, at least or greater than 47 amino acids, at least or greater than 48 amino acids, at least or greater than 49 amino acids, or at least or greater than 50 amino acids in length, or at least 25-50 amino acids in length, at least 30-50 amino acids in length, or at least 35-50 amino acids in length, or at least 40-50 amino acids in length, or at least 45-50 amino acids in length, although smaller proteins may be expressed, and considerably larger proteins (e.g., hundreds of amino acids in length or even a few thousand amino acids in length) may be expressed.

In another embodiment, the invention provides a polypeptide which can be used in vaccines and other compositions for the prevention or therapeutic treatment of cancer, including but not limited to cancers that express or overexpress MUC1, wherein the polypeptide comprises, consists essentially of, or consists of a MUC1 amino acid sequence or fragment thereof (e.g., an immunogenic domain thereof), wherein one or more of the corresponding amino acid residues of the polypeptide have been replaced (e.g., substituted) such that the polypeptide comprises one or more of the enhancer agonist epitopes of SEQ ID NO: 1 or SEQ ID NO: 2 (i.e., the polypeptide has an amino acid sequence that differs from a native, or wild-type, MUC1 amino acid sequence in that the amino acid sequence of the polypeptide comprises one or more of the enhancer agonist epitopes, which typically involves the substitution of one, two, three or more amino acids in a given wild-type epitope sequence with a different amino acid). In one aspect of this embodiment, the polypeptide can further comprise additional MUC1 enhancer agonist epitopes, examples of which are described in detail below.

Peptides and polypeptides (proteins) of the invention are, in some embodiments of the invention, used as antigens. According to the present invention, the general use herein of the term "antigen" refers to any portion of a protein (e.g., peptide, partial protein, full-length protein), wherein the protein is naturally occurring or synthetically derived or designed, to a cellular composition (whole cell, cell lysate or disrupted cells), to an organism (whole organism, lysate or disrupted cells), or to a carbohydrate, or other molecule, or a portion thereof. An antigen may elicit an antigen-specific immune response (e.g., a humoral and/or a cell-mediated immune response) against the same or similar antigens that are encountered in vitro, in vivo, or ex vivo by an element of the immune system (e.g., T cells, antibodies).

An antigen can be as small as a single epitope (e.g., SEQ ID NO: 1 or SEQ ID NO: 2 described herein), a single immunogenic domain or larger, and can include multiple epitopes or immunogenic domains. As such, the size of a protein antigen can be as small as about 8-11 amino acids (e.g., a peptide) and as large as a domain of a protein, a full-length protein, a multimer, a fusion protein, or a chimeric protein. Antigens useful in various immunotherapeutic compositions described herein include peptides, polypeptides, protein domain(s) (e.g., immunogenic domains), protein subunits, full-length proteins, multimers, fusion proteins, and chimeric proteins.

When referring to stimulation of an immune response, the term "immunogen" is a subset of the term "antigen" and, therefore, in some instances, can be used interchangeably with the term "antigen." An immunogen, as used herein, describes an antigen which elicits a humoral and/or cell-mediated immune response (i.e., is immunogenic), such that administration of the immunogen to an individual mounts an antigen-specific immune response against the same or similar antigens that are encountered by the immune system of the individual. In one embodiment, the immunogen elicits a cell-mediated immune response, including a $CD4^+$ T cell response (e.g., TH1, TH2, and/or TH17) and/or a $CD8^+$ T cell response (e.g., a CTL response).

An "immunogenic domain" or "immunological domain" of a given protein (polypeptide) can be any portion, fragment or epitope of an antigen (e.g., a peptide fragment or subunit or an antibody epitope or other conformational epitope) that contains at least one epitope that can act as an immunogen when administered to an animal. Therefore, an immunogenic domain is larger than a single amino acid and is at least of a size sufficient to contain at least one epitope that can act as an immunogen. For example, a single protein can contain multiple different immunogenic domains. Immunogenic domains need not be linear sequences within a protein, such as in the case of a humoral immune response, where conformational domains are contemplated.

An epitope is defined herein as a single immunogenic site within a given antigen that is sufficient to elicit an immune response when provided to the immune system in the context of appropriate costimulatory signals and/or activated cells of the immune system. In other words, an epitope is the part of an antigen that is recognized by components of the immune system, and may also be referred to as an antigenic determinant. Those of skill in the art will recognize that T cell epitopes are different in size and composition from B cell or antibody epitopes, and that epitopes presented through the Class I MHC pathway differ in size and structural attributes from epitopes presented through the Class II MHC pathway. For example, T cell epitopes presented by Class I MHC molecules are typically between 8 and 11 amino acids in length, whereas epitopes presented by Class II MHC molecules are less restricted in length and may be up to 25 amino acids or longer. In addition, T cell epitopes have predicted structural characteristics depending on the specific MHC molecules bound by the epitope. Epitopes can be linear sequence epitopes or conformational epitopes (conserved binding regions). Most antibodies recognize conformational epitopes.

A "target antigen" is an antigen that is specifically targeted by an immunotherapeutic composition of the invention (i.e., an antigen, usually the native antigen, against which elicitation of an immune response is desired, even if the antigen used in the immunotherapeutic is an agonist of the native antigen). A "cancer antigen," which also is referred to as a tumor-associated antigen (TAA), is an antigen that comprises at least one antigen that is associated with a cancer, such as an antigen expressed by a tumor cell, so that targeting the antigen also targets the tumor cell and/or cancer. A cancer antigen can include one or more antigens from one or more proteins, including one or more tumor-associated proteins. In particular, a "MUC1 antigen" is an antigen that is derived, designed, or produced from a MUC1 protein (including MUC1-N, MUC1-C or both MUC1-N and MUC1-C). A "MUC1 agonist antigen" is an antigen derived, designed, or produced from a MUC1 protein (including MUC1-N, MUC1-C or both MUC1-N and MUC1-C) that includes at least one agonist epitope, such as the enhancer agonist epitopes described herein. Preferred enhancer agonist epitopes of the invention have an amino acid sequence of SEQ ID NO: 1 or SEQ ID NO: 2.

MUC1 (which may also be referred to as "mucin-1," "DF3 antigen," or "HMFG1") is a large glycoprotein expressed by most epithelial secretory tissues at basal levels and is expressed at high levels by malignancies of epithelial cell origin. MUC1 is most typically found as a polymorphic, type I transmembrane protein with a large extracellular domain (also referred to as MUC1-N subunit) that includes variable numbers of tandem repeats (VNTR; typically between 20 and 125 repeats) that are highly glycosylated through 0-linkages. The MUC1 protein is encoded as a single transcript, and then processed into subunits post-translationally, known as MUC1-N and MUC1-C, or α and β subunits, respectively, which then form a heterodimeric protein by a strong noncovalent interaction of the two subunits. MUC1 is cleaved into its N- and C-subunits within the "sea urchin sperm protein, enterokinase and agrin" (SEA) domain, a highly conserved protein domain that was named based on its initial identification in a sperm protein, in enterokinase, and in agrin, and that is found in a number of heavily glycosylated mucin-like proteins that are typically membrane-tethered. The MUC1 protein is cleaved between glycine and serine residues present in the sequence GSVVV, which corresponds to positions 1097-1101 of SEQ ID NO: 11, within the SEA domain (Lillehoj et al., *Biochem. Biophys. Res. Commun.*, 307: 743-749 (2003); Parry et al., *Biochem. Biophys. Res. Commun.*, 283: 715-720 (2001); Wreschner et al., *Protein Sci.*, 11: 698-706 (2002)).

The MUC1-C subunit includes the extracellular domain (ED), which is glycosylated and binds the galectin-3 ligand, which in turn serves as a bridge to physically associate MUC1 with the epidermal growth factor receptor (EGFR) and possibly other receptor tyrosine kinases. MUC1-C also comprises a transmembrane (TM) domain, and a cytoplasmic domain (CD) which contains several tyrosine residues which, when phosphorylated, could act as binding motifs for proteins with SH2 domains (for a detailed discussion of the MUC1 protein and known and putative functions, see Kufe, *Cancer Biol. & Ther.*, 7: 81-84 (2008)). Alternative splice variants of MUC1 (known as MUC1/Y and MUC1/X, for example) are "short" versions of MUC1 that lack most of MUC1-N, including the large VNTR region, but that include the ED, TM and CD regions, as well as the SEA domain and portions of the N-terminal region signal sequence region. Cleavage within the SEA domain may not occur in these short versions.

The isolation and sequencing of DNA and cDNA encoding human MUC1 has been reported (see, e.g., Siddiqui et al., *PNAS*, 85: 2320-2323 (1998); Abe and Kufe, *PNAS*, 90: 282-286 (1993); Hareuveni et al., *Eur. J. Biochem.*, 189(3): 475-486 (1990); Gendler et al., *J. Biol. Chem.*, 265(25): 15286-15293 (1990); Lan et al., *J. Biol. Chem.*, 265(25): 15294-15299 (1990); Tsarfaty et al., *Gene*, 93(2): 313-318 (1990); Lancaster, *Biochem. Biophys. Res. Commun.*, 173 (3): 1019-1029 (1990)). An example of a full-length human MUC1 precursor protein containing both the MUC1-N and MUC1-C regions is described in SwissProt Accession No. P15941.3 (GI:296439295), and is represented here by SEQ ID NO: 5. 10 different MUC1 isoforms can be created from the gene encoding SEQ ID NO: 5 by alternative transcript splicing. For example, an isoform known as MUC1/Y lacks positions 54-1053 of SEQ ID NO: 5. Various other isoforms are described in the database description of this protein.

A variety of transcript variants of MUC1 are known, but the MUC1 subunits, domains, or regions described in the exemplary SEQ ID NO: 5 above can readily be identified in the variants, such that a MUC1 antigen useful in the invention can be designed or produced based on a given MUC1 sequence, or a corresponding sequence from another MUC1 protein. For example, one nucleotide sequence encoding a human MUC1 protein is represented herein by SEQ ID NO: 6, which corresponds to GENBANK® Accession No. NM_002456.4 (GI: 65301116). SEQ ID NO: 6 encodes a 273 amino acid human MUC1 protein (transcript variant 1, also known as MUC1/ZD), the amino acid sequence of which is represented here as SEQ ID NO: 7 (also found in GENBANK® Accession No. NP_002447.4; GI:65301117). Another nucleotide sequence encoding another human MUC1 protein is represented herein by SEQ ID NO: 8, which corresponds to GENBANK® Accession No. NM_001018016.1 (GI:67189006). SEQ ID NO: 8 encodes a 264 amino acid human MUC1 protein (transcript variant 2, also known as "MUC1/Y"), the amino acid sequence of which is represented here as SEQ ID NO: 9 (also found in GENBANK® Accession No. NP_001018016.1; GI:67189007). Another nucleotide sequence encoding another human MUC1 protein is represented herein by SEQ ID NO: 10, which corresponds to GENBANK® Accession No. AY327587.1 (GI:33150003). SEQ ID NO: 10 encodes a 264 amino acid human MUC1 protein (transcript variant 2, also known as "MUC1/Y"), the amino acid sequence of which is represented here as SEQ ID NO: 11 (also found in GENBANK® Accession No. AAP97018.1 (GI: 33150004). Another nucleotide sequence encoding another human MUC1 protein is represented herein by SEQ ID NO: 12, which corresponds to GENBANK® Accession No. NM_001018017 (GI:324120954). SEQ ID NO: 12 encodes a 255 amino acid human MUC1 protein (transcript variant 3), the amino acid sequence of which is represented here as SEQ ID NO: 13 (also found in GENBANK® Accession No. NP_001018017.1; GI:67189069). Yet another exemplary wild-type MUC1 amino acid sequence is represented here by SEQ ID NO: 14 (also found in GENBANK® Accession No. NP_001191214). SEQ ID NO: 14 is used as a reference for some of the amino acid positions of MUC1 described herein, but the corresponding positions in other MUC1 sequences can be identified by those of skill in the art.

Human MUC1, including the human MUC1 proteins and MUC1 antigens described herein, contains various $CD4^+$ and $CD8^+$ T cell epitopes. Such T cell epitopes have been described, for example, in U.S. Pat. Nos. 6,546,643; 7,118, 738; 7,342,094; 7,696,306; and U.S. Patent Application Publication No. 2008/0063653, as well as in PCT Publication No. WO 2013/024972, and any one or more of these epitopes can be used in a MUC1 antigen of the present invention, including by adding, deleting or substituting one or more amino acids within a sequence described herein to conform the sequence to the published epitope sequence at that position(s).

Examples of MUC1 agonist antigens discovered in the present invention are provided herein (see Examples). A peptide, protein, or polypeptide useful in the present invention comprises, consists essentially of, or consists of at least one of the MUC1 enhancer agonist peptides represented by SEQ ID NO: 1 and SEQ ID NO: 2. However, other MUC1 agonist epitopes can be additionally included in a MUC1 antigen for use in the present invention. In one embodiment, a MUC1 agonist antigen suitable for use in the present invention comprises a MUC1 protein or polypeptide or peptide thereof having an amino acid sequence that differs from the wild-type (native) MUC1 protein or polypeptide or peptide thereof by at least 1, 2, 3, 4, 5, 6, 7, 8, 9, 10, 11, 12, 13, 14, 15, or more amino acid substitutions, where the amino acid substitutions introduce one or more MUC1 agonist epitopes into the antigen. Such amino acid substitutions can include substitutions at the following amino acid positions, where the positions of the substitutions are provided with respect to a wild-type MUC1 having an amino acid sequence represented by Accession No. NP 001191214 (SEQ ID NO: 14) (although the same or equivalent positions can be readily identified in any other wild-type MUC1 sequence): T93, A141, P142, G149, S150, T151, A392, C406, T422, P430, T431, T444, D445, S460, S462, and/or A470. In one embodiment, the substitution is: T93L, A141Y, P142L, G149V, S150Y, T151L, A392Y, C406V, T422K, P430A, T431L, T444L, D445F, S460Y, S462K, and/or A470L.

In addition, a MUC1 antigen useful in the present invention may include one or more additional amino acid mutations (substitutions, insertions or deletions), for example, to inactivate or delete a natural biological function of the native protein (e.g., to improve expression or enhance safety of the antigen). One example of such a mutation is an inactivating mutation that is a substitution at position C404 with respect to the wild-type protein using SEQ ID NO: 14 as a reference sequence. In one aspect, the inactivating substitution is C404A (with respect to SEQ ID NO: 14).

The peptide or polypeptide (protein) of the invention can be prepared by any method, such as by synthesizing the peptide or by expressing a nucleic acid encoding an appropriate amino acid sequence for the peptide or polypeptide in a cell and, in some embodiments, harvesting the peptide or polypeptide from the cell. In some embodiments, the peptide or polypeptide is not harvested from the cell, such as in embodiments of the invention directed to a yeast-based immunotherapy composition, which is described in detail below. A combination of such methods of production of peptides and polypeptides also can be used. Methods of de novo synthesizing peptides and methods of recombinantly producing peptides or polypeptides are known in the art (see, e.g., Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2000; Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, N Y, 1994).

The invention also provides a nucleic acid molecule comprising a nucleic acid sequence encoding the peptide or the polypeptide. The nucleic acid molecule can comprise DNA (genomic or cDNA) or RNA, and can be single or double stranded. Furthermore, the nucleic acid molecule can comprise nucleotide analogues or derivatives (e.g., inosine or phophorothioate nucleotides and the like). The nucleic acid sequence can encode the peptide or polypeptide alone or as part of a fusion protein. The nucleic acid sequence encoding the peptide or polypeptide can be provided as part of a construct comprising the nucleic acid molecule and elements that enable delivery of the nucleic acid molecule to a cell, and/or expression of the nucleic acid molecule in a cell. Such elements include, for example, expression vectors, promoters, and transcription and/or translation control sequences. Such constructs can also be referred to as "recombinant nucleic acid molecules". Suitable vectors, promoters, transcription/translation sequences, and other elements, as well as methods of preparing such nucleic acid molecules and constructs, are known in the art (e.g., Sambrook et al., supra; and Ausubel et al., supra). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a peptide or polypeptide. Similarly, the phrase "recombinant nucleic acid molecule" primarily refers to a nucleic acid molecule operatively linked to an element such as a transcription control sequence, but can be used interchangeably with the phrase "nucleic acid molecule."

The invention further provides a vector comprising the nucleic acid molecule. Examples of suitable vectors include plasmids (e.g., DNA plasmids) and viral vectors, such as poxvirus, retrovirus, adenovirus, adeno-associated virus, herpes virus, polio virus, alphavirus, baculorvirus, and Sindbis virus.

In a first embodiment, the vector is a plasmid (e.g., DNA plasmid). The plasmid can be complexed with chitosan.

In a second embodiment, the vector is a poxvirus (e.g., chordopox virus vectors and entomopox virus vectors). Suitable poxviruses include orthopox, avipox, parapox, yatapox, and molluscipox, raccoon pox, rabbit pox, capripox (e.g., sheep pox), leporipox, and suipox (e.g., swinepox). Examples of avipox viruses include fowlpox, pigeonpox, canarypox, such as ALVAC, mynahpox, uncopox, quailpox, peacockpox, penguinpox, sparrowpox, starlingpox, and turkeypox. Examples of orthopox viruses include smallpox (also known as variola), cowpox, monkeypox, vaccinia, ectromelia, camelpox, raccoonpox, and derivatives thereof.

The term "vaccinia virus" refers to both the wild-type vaccinia virus and any of the various attenuated strains or isolates subsequently isolated including, for example, modified vaccinia Ankara (MVA), NYVAC, TROYVAC, DryVax (also known as vaccinia virus-Wyeth), PDXVAC-TC (Schering-Plough Corporation), vaccinia virus-Western Reserve, vaccinia virus-EM63, vaccinia virus-Lister, vaccinia virus-New York City Board of Health, vaccinia virus-Temple of Heaven, vaccinia virus-Copenhagen, ACAM1000, ACAM2000, and modified vaccinia virus Ankara-Bavarian Nordic ("MVA-BN").

In certain embodiments, the MVA is selected from the group consisting of MVA-572, deposited at the European Collection of Animal Cell Cultures ("ECACC"), Health Protection Agency, Microbiology Services, Porton Down, Salisbury SP4 0JG, United Kingdom ("UK"), under the deposit number ECACC 94012707 on Jan. 27, 1994; MVA-575, deposited at the ECACC under deposit number ECACC 00120707 on Dec. 7, 2000; MVA-Bavarian Nordic ("MVA-BN"), deposited at the ECACC under deposit number V00080038 on Aug. 30, 2000; and derivatives of MVA-BN. Additional exemplary poxvirus vectors are described in U.S. Pat. No. 7,211,432.

The vaccinia virus MVA was generated by 516 serial passages on chicken embryo fibroblasts of the Ankara strain of Vaccinia virus, referred to as chorioallantois virus Ankara (CVA) (see Mayr et al., Infection, 3: 6-14 (1975)). The genome of the resulting attenuated MVA lacks approximately 31 kilobase pairs of genomic DNA compared to the parental CVA strain and is highly host-cell restricted to avian cells (see Meyer et al., J. Gen. Virol., 72: 1031-1038 (1991)). It was shown in a variety of animal models that the resulting MVA was significantly avirulent (Mayr et al., Dev. Biol. Stand., 41: 225-34 (1978)). This MVA strain has been tested in clinical trials as a vaccine to immunize against smallpox in humans (see Mary et al., Zbl. Bakt. Hyg. I, Abt. Org. B, 167: 375-390 (1987); and Stickl et al., Dtsch. Med. Wschr., 99: 2386-2392 (1974)). Those studies involved over 120,000 humans, including high-risk patients, and proved that compared to vaccinia virus-based vaccines, MVA had diminished virulence or infectiousness while still able to induce a good specific immune response. Although MVA-BN is preferred for its better safety profile because it is less replication competent than other MVA strains, all MVAs are suitable for this invention, including MVA-BN and its derivatives.

Both MVA and MVA-BN are able to efficiently replicate their DNA in mammalian cells even though they are avirulent. This trait is the result of losing two important host range genes among at least 25 additional mutations and deletions that occurred during its passages through chicken embryo fibroblasts (see Meyer et al., Gen. Virol., 72: 1031-1038 (1991); and Antoine et al., Virol., 244: 365-396 (1998)). In contrast to the attenuated Copenhagen strain (NYVAC) and host range restricted avipox (ALVAC), both-early and late transcription in MVA are unimpaired, which allows for continuous gene expression throughout the viral life cycle (see Sutter et al., Proc. Nat'l Acad. Sci. USA, 89:10847-10851 (1992)). In addition, MVA can be used in conditions of pre-existing poxvirus immunity (Ramirez et al., J. Virol., 74: 7651-7655 (2000)).

Both MVA and MVA-BN lack approximately 15% (31 kb from six regions) of the genome compared with the ancestral chorioallantois vaccinia virus Ankara ("CVA"). The deletions affect a number of virulence and host range genes, as well as the gene for Type A inclusion bodies. MVA-BN can attach to and enter human cells where virally-encoded genes are expressed very efficiently. However, assembly and release of progeny virus does not occur. MVA-BN is strongly adapted to primary chicken embryo fibroblast (CEF) cells and does not replicate in human cells. In human cells, viral genes are expressed, and no infectious virus is produced. Despite its high attenuation and reduced virulence, in preclinical studies, MVA-BN has been shown to elicit both humoral and cellular immune responses to vaccinia and to heterologous gene products encoded by genes cloned into the MVA genome (see Harrer et al., Antivir. Ther., 10(2): 285-300 (2005); Cosma et al., Vaccine, 22(1): 21-29 (2003); Di Nicola et al., Hum. Gene Ther., 14(14): 1347-1360 (2003); and Di Nicola et al., Clin. Cancer Res., 10(16): 5381-5390 (2004)).

The reproductive replication of a virus is typically expressed by the amplification ratio. The term "amplification ratio" refers to the ratio of virus produced from an infected cell ("output") to the amount originally used to infect the cells in the first place ("input"). An amplification ratio of "1" defines an amplification status in which the amount of virus produced from infected cells is the same as the amount initially used to infect the cells, which means that the infected cells are permissive for virus infection and reproduction. An amplification ratio of less than 1 means that infected cells produce less virus than the amount used to infect the cells in the first place, and indicates that the virus lacks the capability of reproductive replication, which is a measure of virus attenuation.

Thus, the term "not capable of reproductive replication" means that an MVA or MVA derivative has an amplification ratio of less than 1 in one or more human cell lines, such as, for example, the human embryonic kidney 293 cell line (HEK293, which is deposited under deposit number ECACC No. 85120602), the human bone osteosarcoma cell line 143B (deposited under deposit number ECACC No. 91112502), the human cervix adenocarcinoma cell line HeLa (deposited at the American Type Culture Collection (ATTC) under deposit number ATCC No. CCL-2), and the human keratinocyte cell line HaCat (see Boukamp et al., J. Cell Biol., 106(3): 761-71 (1988)).

MVA-BN does not reproductively replicate in the human cell lines HEK293, 143B, HeLa, and HaCat (see U.S. Pat. Nos. 6,761,893 and 6,193,752, and International Patent Application Publication No. WO 2002/042480). For example, in one exemplary experiment, MVA-BN exhibited an amplification ratio of 0.05 to 0.2 in HEK293 cells, an amplification ratio of 0.0 to 0.6 in 143B cells, an amplification ratio of 0.04 to 0.8 in HeLa cells, and an amplification ratio of 0.02 to 0.8 in HaCat cells. Thus, MVA-BN does not reproductively replicate in any of the human cell lines HEK293, 143B, HeLa, and HaCat. In contrast, the amplification ratio of MVA-BN is greater than 1 in primary cultures of chicken embryo fibroblast cells (CEF) and in baby hamster kidney cells (BHK, which is deposited under deposit number ATCC No. CRL-1632). Therefore MVA-BN can easily be propagated and amplified in CEF primary cultures with an amplification ratio above 500, and in BHK cells with an amplification ratio above 50.

As noted above, all MVAs are suitable for this invention, including MVA-BN and its derivatives. The term "derivatives" refers to viruses showing essentially the same replication characteristics as the strain deposited with ECACC on Aug. 30, 2000, under deposit number ECACC No. V00080038 but showing differences in one or more parts of its genome. Viruses having the same "replication characteristics" as the deposited virus are viruses that replicate with similar amplification ratios as the deposited strain in CEF cells, in BHK cells, and in the human cell lines HEK293, 143B, HeLa, and HaCat.

When the vector is for administration to a host (e.g., human), the vector (e.g., poxvirus) preferably has a low replicative efficiency in a target cell (e.g., no more than about 1 progeny per cell or, more preferably, no more than 0.1 progeny per cell are produced). Replication efficiency can readily be determined empirically by determining the virus titer after infection of the target cell.

In addition to the nucleic acid molecule encoding the polypeptide (protein) or polypeptide (i.e., the peptide or polypeptide comprising, consisting essentially of, or consisting of at least one MUC1 enhancer agonist epitope described herein), a vector useful in the invention (e.g., a plasmid or a viral vector) also can comprise a nucleic acid sequence encoding one or more immunostimulatory/regulatory molecules, granulocyte macrophage colony stimulating factor (GM-CSF), cytokines, and/or molecules that can enhance an immune response (e.g., additional tumor-associated antigens). Exemplary additional tumor-associated antigens (TAAs, also referred to as cancer antigens) include, but are not limited to, 5-α-reductase, α-fetoprotein (AFP), AM-1, APC, April, B melanoma antigen gene (BAGE), β-catenin, Bcl12, bcr-abl, Brachyury, CA-125, caspase-8 (CASP-8 also known as FLICE), Cathepsins, CD19, CD20, CD21/complement receptor 2 (CR2), CD22/BL-CAM, CD23/$F_c\varepsilon RII$, CD33, CD35/complement receptor 1 (CR1), CD44/PGP-1, CD45/leucocyte common antigen (LCA), CD46/membrane cofactor protein (MCP), CD52/CAMPATH-1, CD55/decay accelerating factor (DAF), CD59/protectin, CDC27, CDK4, carcinoembryonic antigen (CEA), c-myc, cyclooxygenase-2 (cox-2), deleted in colorectal cancer gene (DCC), DcR3, E6/E7, CGFR, EMBP, Dna78, farnesyl transferase, fibroblast growth factor-8a (FGF8a), fibroblast growth factor-8b (FGF8b), FLK-1/KDR, folic acid receptor, G250, G melanoma antigen gene family (GAGE-family), gastrin 17, gastrin-releasing hormone, ganglioside 2 (GD2)/ganglioside 3 (GD3)/ganglioside-monosialic acid-2 (GM2), gonadotropin releasing hormone (GnRH), UDP-GlcNAc:$R_1$Man($\alpha$1-6)$R_2$ [GlcNAc to Man($\alpha$1-6)] β1,6-N-acetylglucosaminyltransferase V (GnT V), GP1, gp100/Pme117, gp-100-in4, gp15, gp75/tyrosine-related protein-1 (gp75/TRP-1), human chorionic gonadotropin (hCG), heparanase, Her2/neu, human mammary tumor virus (HMTV), 70 kiloDalton heat-shock protein (HSP70), human telomerase reverse transcriptase (hTERT), insulin-like growth factor receptor-1 (IGFR-1), interleukin-13 receptor (IL-13R), inducible nitric oxide synthase (iNOS), Ki67, KIAA0205, K-ras, H-ras, N-ras, KSA, LKLR-FUT, melanoma antigen-encoding family (MAGE-family, including at least MAGE-1, MAGE-2, MAGE-3, and MAGE-4), mammaglobin, MAP17, Melan-A/melanoma antigen recognized by T-cells-1 (MART-1), mesothelin, MIC A/B, MT-MMPs, mucin, testes-specific antigen NY-ESO-1, osteonectin, p15, P170/MDR1, p53, p97/melanotransferrin, PAI-1, platelet-derived growth factor (PDGF), μPA, PRAME, probasin, progenipoietin, prostate-specific antigen (PSA), prostate-specific membrane antigen (PSMA), RAGE-1, Rb, RCAS1, mutated Ras, SART-1, SSX-family, STAT3, STn, TAG-72, transforming growth factor-alpha (TGF-α), transforming growth factor-beta (TGF-β), Thymosin-beta-15, tumor necrosis factor-alpha (TNF-α), TP1, TRP-2, tyrosinase, vascular endothelial growth factor (VEGF), ZAG, p16INK4, and glutathione-S-transferase (GST), as well as modified versions thereof (e.g., CEA-6D).

In the case of a viral vector, the nucleic acid encoding the peptide, as well as any other exogenous gene(s), preferably are inserted into a site or region (insertion region) in the vector (e.g., poxvirus) that does not affect virus viability of the resultant recombinant virus. Such regions can be readily identified by testing segments of virus DNA for regions that allow recombinant formation without seriously affecting virus viability of the recombinant virus.

The thymidine kinase (TK) gene is an insertion region that can readily be used and is present in many viruses. In particular, the TK gene has been found in all examined poxvirus genomes. Additional suitable insertion sites are described in International Patent Application Publication WO 2005/048957. For example, in fowlpox, insertion regions include, but are not limited to, the BamHI J fragment, EcoRI-HindIII fragment, BamHI fragment, EcoRV-HindIII fragment, long unique sequence (LUS) insertion sites (e.g., FPV006/FPV007 and FPV254/FPV255), FP14 insertion site (FPV060/FPV061), and 43K insertion site (FPV107/FPV108). In vaccinia, insertion sites include, but are not limited to, 44/45, 49/50, and 124/125.

When the vector is a recombinant fowlpox virus comprising a nucleic acid encoding the peptide and/or other exogenous gene(s) (e.g., encoding one or more immunostimulatory/regulatory molecules), the nucleic acid encoding the peptide can be inserted in one region (e.g., the FP14 region), and the exogenous gene(s) can be inserted in another region (e.g., the BamHI J region).

The inventive vector can include suitable promoters and regulatory elements, such as a transcriptional regulatory element or an enhancer. Suitable promoters include the SV40 early promoter, an RSV promoter, the retrovirus LTR, the adenovirus major late promoter, the human CMV immediate early I promoter, and various poxvirus promoters, such as the Pr7.5K promoter, 30K promoter, 40K promoter, I3 promoter, Prs promoter, PrsSynIIm promoter, PrLE1 promoter, synthetic early/late (sE/L) promoter, HH promoter, 11K promoter, and Pi promoter. While the promoters typically will be constitutive promoters, inducible promoters also can be used in the inventive vectors. Such inducible systems allow regulation of gene expression.

In one embodiment of the invention, a cell comprising (1) the peptide or polypeptide, (2) a nucleic acid molecule encoding the peptide or polypeptide, and/or (3) a vector comprising the nucleic acid molecule also is provided herein. Suitable cells include prokaryotic and eukaryotic cells, e.g., mammalian cells, yeast, fungi other than yeast, and bacteria (such as *E. coli*). The cell can be used in vitro, such as for research or for production of the peptide or polypeptide, or the cell can be used in vivo. In one embodiment, the cell is a yeast cell, which may be used to provide a yeast vehicle component of the yeast-based immunotherapy composition as described herein. In another embodiment, the cell can be a peptide-pulsed antigen presenting cell. Suitable antigen presenting cells include, but are not limited to, dendritic cells, B lymphocytes, monocytes, macrophages, and the like.

In one embodiment, the cell is dendritic cell. Dendritic cells of different maturation stages can be isolated based on the cell surface expression markers. For example, mature dendritic cells are less able to capture new proteins for presentation but are much better at stimulating resting T cells to grow and differentiate. Thus, mature dendritic cells can be of importance. Mature dendritic cells can be identified by their change in morphology and by the presence of various markers. Such markers include, but are not limited to, cell surface markers such as B7.1, B7.2, CD40, CD11, CD83, and MHC class II. Alternatively, maturation can be identified by observing or measuring the production of pro-inflammatory cytokines.

Dendritic cells can be collected and analyzed using typical cytofluorography and cell sorting techniques and devices, such as a fluorescence-activated cell sorter (FACS). Antibodies specific to cell surface antigens of different stages of dendritic cell maturation are commercially available.

In one embodiment, the cell is a yeast (e.g., *Saccharomyces*). Accordingly, the invention also provides a yeast-based immunotherapeutic composition comprising (a) a yeast vehicle and (b) an antigen comprising a MUC1 peptide or polypeptide (protein) of the invention (also generally referred to herein as "yeast-immunotherapy composition," "yeast-immunotherapy product," "yeast-immunotherapeutic composition," "yeast-based vaccine," or derivatives of these phrases). A yeast-based immunotherapeutic composition that contains a MUC1 antigen can be referred to more specifically as a "yeast-MUC1 immunotherapeutic composition" or derivatives thereof as noted above. An "immunotherapeutic composition" is a composition that elicits an immune response sufficient to achieve at least one therapeutic benefit in a subject. A "yeast-based immunotherapeutic composition" (and derivatives thereof) refers to a composition that includes a yeast vehicle component and an antigen component, and can elicit or induce an immune response, such as a cellular immune response, including without limitation a T cell-mediated cellular immune response. The immune response generally includes both an innate immune response and an adaptive immune response, and is generated against both the yeast component and the antigen component (an antigen-specific immune response). Preferably, the yeast-based immunotherapeutic composition, when administered to an individual, provides at least one protective, preventative, or therapeutic benefit to the individual. In one aspect, a yeast-based immunotherapeutic composition useful in the invention is capable of inducing a $CD8^+$ and/or a $CD4^+$ T cell-mediated immune response and in one aspect, a $CD8^+$ and a $CD4^+$ T cell-mediated immune response, particularly against a target antigen (e.g., a cancer antigen, and preferably against MUC1). A $CD4^+$ immune response can include TH1 immune responses, TH2 immune responses, TH17 immune responses, or any combination of the above. A $CD8^+$ immune response can include a cytotoxic T lymphocyte (CTL) response. In one aspect, a yeast-based immunotherapeutic composition modulates the number and/or functionality of regulatory T cells (Tregs) in a subject.

As described above, a yeast-based immunotherapy composition of the invention includes (a) a yeast vehicle and (b) at least one cancer antigen comprising a MUC1 antigen or immunogenic domain thereof, where the MUC1 antigen comprises, consists essentially of, or consists of, at least one MUC1 enhancer agonist epitope having an amino acid sequence selected from SEQ ID NO: 1 and/or SEQ ID NO: 2. The cancer antigen is expressed by (i.e., recombinantly), attached to, loaded into, or mixed with the yeast vehicle.

In some embodiments, the cancer antigen, MUC1 antigen, or immunogenic domain thereof is provided as a fusion protein. For example, several MUC1 proteins and fusion proteins have been described in PCT Publication No. WO 2013/024972. Such proteins and fusion proteins can be further modified to incorporate the enhancer agonist epitopes of the present invention. In some embodiments, the cancer antigen and the MUC1 antigen are the same element. In some embodiments, the cancer antigen includes other antigens, including other cancer antigens (also referred to herein as tumor associated antigens or TAAs) in addition to the MUC1 antigen. In one aspect of the invention, a fusion protein useful as a cancer antigen can include two or more antigens, e.g., a MUC1 antigen and another cancer antigen (TAA) that is not a MUC1 antigen, or two different MUC1 antigens. In one aspect, the fusion protein can include two or more immunogenic domains of one or more antigens, such as two or more immunogenic domains of a MUC1 antigen, or two or more epitopes of one or more antigens, such as two or more epitopes of a MUC1 antigen. A variety of other cancer antigens or TAAs are known in the art and are described elsewhere herein.

An example of a MUC1 antigen that is useful in an inventive yeast-based immunotherapy composition comprises or consists of the amino acid sequence of SEQ ID NO: 16. SEQ ID NO: 16 is the amino acid sequence of a fusion protein comprising a MUC1 antigen for use in a yeast-based immunotherapy composition, where the MUC1 antigen is a full-length MUC1 agonist protein corresponding to a wild-type MUC1 protein except for (a) the introduction of 15 amino acid substitutions to form several agonist epitopes within the protein, including the enhancer agonist epitope of SEQ ID NO: 1 and (b) a single amino acid substitution that is an inactivating mutation. SEQ ID NO: 16 includes the following sequences in the following order from N- to C-terminus: (1) an alpha factor leader sequence of SEQ ID NO:17 (corresponding to positions 1-89 of SEQ ID NO: 16); (2) a linker sequence of Thr-Ser to facilitate cloning (corresponding to positions 90-91 of SEQ ID NO: 16); (3) a full-length MUC1 agonist protein corresponding to a wild-type protein except for the introduction of the above-mentioned 15 amino acid agonist substitutions and one inactivating substitution (corresponding to positions 92-566 of SEQ ID NO: 16) and (4) a hexapeptide histidine tag (corresponding to positions 567-572 of SEQ ID NO: 16).

SEQ ID NO: 16 is encoded by the nucleotide sequence represented by SEQ ID NO: 15 (codon optimized for yeast expression). The alpha leader sequence (corresponding to positions 1-89 of SEQ ID NO: 16) could be substituted with a different N-terminal sequence designed to impart resistance to proteasomal degradation and/or stabilize expression, such as the peptide represented by SEQ ID NO: 19 or an N-terminal peptide from a different yeast alpha leader sequence, such as SEQ ID NO: 18, or by a MUC1 signal sequence. The hexahistidine C-terminal tag is optional and facilitates identification and/or purification of the protein.

As compared to the wild-type MUC1 protein used as a template, the sequence of SEQ ID NO: 16 contains the following amino acid substitutions: (substitution positions given with reference to SEQ ID NO: 16 with further reference in parentheses to the location of the substitution in a wild-type MUC1 represented by Accession No. NP 001191214 corresponding to SEQ ID NO: 14): T184L (position 93 in wild-type MUC1), A232Y (position 141 in wild-type MUC1), P233L (position 142 in wild-type MUC1), G240V (position 149 in wild-type MUC1), S241Y (position 150 in wild-type MUC1), T242L (position 151 in wild-type MUC1), A483Y (position 392 in wild-type MUC1), C495A (position 404 in wild-type MUC1) C497V (position 406 in wild-type MUC1), T513K (position 422 in wild-type MUC1), P521A (position 430 in wild-type MUC1), T522L (position 431 in wild-type MUC1), T535L (position 444 in wild-type MUC1), D536F (position 445 in wild-type MUC1), and S551Y (position 460 in wild-type MUC1). The substitution C495A (position 404 in the wild-type MUC1 protein) is the inactivating mutation; the remainder of the substitutions are to produce agonist epitopes.

SEQ ID NO: 16 comprises the enhancer agonist peptide referred to herein as SEQ ID NO: 1. SEQ ID NO: 1 is located at positions 513-522 of SEQ ID NO: 16.

The MUC1 antigen for yeast-based immunotherapy represented by SEQ ID NO: 16 contains agonist epitopes for several different HLA types, including A2, A3 and A24, making it a versatile and unique antigen for targeting tumors in a variety of individuals with a MUC1 expressing cancer.

A MUC1 antigen useful in the yeast-based immunotherapy composition of the present invention also includes antigens having an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of SEQ ID NO: 16 over the full length of the fusion protein or over a defined fragment of SEQ ID NO: 16 (e.g., an immunological domain or functional domain (domain with at least one biological activity)) that forms part of the protein, including, but not limited to, positions 92-566 of SEQ ID NO: 16 (the MUC1 antigen within SEQ ID NO: 16).

It is straightforward to use the corresponding portions of any of the MUC1 proteins that are derived or obtained from sequence or sources other than those exemplified herein, and particularly from sequences or sources within the same animal species, to create peptides, polypeptides, and fusion proteins having a similar or the same overall structure as the peptides, polypeptides, and fusion proteins described herein. By way of example, one can readily identify a corresponding sequence in a given human MUC1 protein from any source that corresponds to positions 92-566 of SEQ ID NO: 16 using simple sequence alignment tools or processes. Therefore, sequences with minor and/or conservative differences from the sequences exemplified herein are expressly encompassed by the present invention.

As discussed above, N-terminal expression sequences and the C-terminal tags, such as those described above with respect to the fusion protein of SEQ ID NO: 16 are optional, but may be selected from several different sequences to improve or assist with expression, stability, and/or allow for identification and/or purification of the protein. For example, an exemplary N-terminal synthetic sequence that enhances the stability of expression of an antigen in a yeast cell and/or prevents post-translational modification of the protein in the yeast includes the sequence M-A-D-E-A-P (represented herein by SEQ ID NO: 19). In other embodiments, the MUC1 antigen is linked at the N-terminus to a yeast protein, such as an alpha factor prepro sequence (also referred to as the alpha factor signal leader sequence, the amino acid sequence of which is exemplified herein by SEQ ID NO: 17 or SEQ ID NO: 18). Other sequences for yeast alpha factor prepro sequence are known in the art and are encompassed for use in the present invention. Also, many different promoters suitable for use in yeast are known in the art. Furthermore, short intervening linker sequences (e.g., 1, 2, 3, 4, or 5 amino acid peptides) may be introduced between portions of a fusion protein comprising a MUC1 antigen for a variety of reasons, including the introduction of restriction enzyme sites to facilitate cloning, as cleavage sites for host phagosomal proteases, to accelerate protein or antigen processing, and for future manipulation of the constructs.

For use in embodiments of the invention directed to yeast, any suitable yeast promoter can be used and a variety of such promoters are known to those skilled in the art. Promoters for expression in *Saccharomyces cerevisiae* include, but are not limited to, promoters of genes encoding the following yeast proteins: alcohol dehydrogenase I (ADH1) or II (ADH2), CUP1, phosphoglycerate kinase (PGK), triose phosphate isomerase (TPI), translational elongation factor EF-1 alpha (TEF2), glyceraldehyde-3-phosphate dehydrogenase (GAPDH; also referred to as TDH3, for triose phosphate dehydrogenase), galactokinase (GAL1), galactose-1-phosphate uridyl-transferase (GAL7), UDP-galactose epimerase (GAL10), cytochrome c1 (CYC1), Sec7 protein (SECT) and acid phosphatase (PHOS), including hybrid promoters such as ADH2/GAPDH and CYC1/GAL10 promoters, and including the ADH2/GAPDH promoter, which is induced when glucose concentrations in the cell are low (e.g., about 0.1 to about 0.2 percent), as well as the CUP1 promoter and the TEF2 promoter. Likewise, a number of upstream activation sequences (UASs), also referred to as enhancers, are known. Upstream activation sequences for expression in *Saccharomyces cerevisiae* include, but are not limited to, the UASs of genes encoding the following proteins: PCK1, TPI, TDH3, CYC1, ADH1, ADH2, SUC2, GAL1, GAL7 and GAL10, as well as other UASs activated by the GAL4 gene product, with the ADH2 UAS being used in one aspect. Since the ADH2 UAS is activated by the ADR1 gene product, it may be preferable to overexpress the ADR1 gene when a heterologous gene is operatively linked to the ADH2 UAS. Transcription termination sequences for expression in *Saccharomyces cerevisiae* include the termination sequences of the α-factor, GAPDH, and CYC1 genes.

Transcription control sequences to express genes in methyltrophic yeast include the transcription control regions of the genes encoding alcohol oxidase and formate dehydrogenase.

According to the present invention, a "yeast vehicle" used in a yeast-based immunotherapy composition is any yeast cell (e.g., a whole or intact cell) or a derivative thereof (see below) that can be used in conjunction with one or more antigens, immunogenic domains thereof, or epitopes thereof in a yeast-based immunotherapeutic composition of the invention (e.g., a therapeutic or prophylactic composition). The yeast vehicle therefore can include, but is not limited to, a live intact (whole) yeast microorganism (i.e., a yeast cell having all its components including a cell wall), a killed (dead) or inactivated intact yeast microorganism, derivatives of intact yeast including a yeast spheroplast (i.e., a yeast cell lacking a cell wall), a yeast cytoplast (i.e., a yeast cell lacking a cell wall and nucleus), a yeast ghost (i.e., a yeast cell lacking a cell wall, nucleus, and cytoplasm), a subcellular yeast membrane extract or fraction thereof (also referred to as a yeast membrane particle and previously as a subcellular yeast particle), any other yeast particle, or a yeast cell wall preparation.

Yeast spheroplasts are typically produced by enzymatic digestion of the yeast cell wall. Such a method is described, for example, in Franzusoff et al., *Meth. Enzymol.*, 194: 662-674 (1991). Yeast cytoplasts are typically produced by enucleation of yeast cells. Such a method is described, for example, in Coon, *Natl. Cancer Inst. Monogr.*, 48: 45-55 (1978). Yeast ghosts are typically produced by resealing a permeabilized or lysed cell and can, but need not, contain at least some of the organelles of that cell. Such a method is described, for example, in Franzusoff et al., *J. Biol. Chem.*, 258, 3608-3614 (1983) and Bussey et al., *Biochim. Biophys. Acta*, 553: 185-196 (1979). A yeast membrane particle (subcellular yeast membrane extract or fraction thereof) refers to a yeast membrane that lacks a natural nucleus or cytoplasm. The particle can be of any size, including sizes ranging from the size of a natural yeast membrane to microparticles produced by sonication or other membrane disruption methods known to those skilled in the art, followed by resealing. A method for producing subcellular yeast membrane extracts is described, for example, in Franzusoff et al., *Meth. Enzymol.*, 194, 662-674 (1991). One also can use fractions of yeast membrane particles that contain yeast membrane portions and, when the antigen or other protein is expressed recombinantly by the yeast prior to preparation of the yeast membrane particles, the antigen or other protein of interest. Antigens or other proteins of interest can be carried inside the membrane, on either surface of the membrane, or combinations thereof (i.e., the protein can be both inside and outside the membrane and/or spanning the membrane of the yeast membrane particle). In one embodiment, a yeast membrane particle is a recombinant yeast membrane particle that can be an intact, disrupted, or disrupted and resealed yeast membrane that includes at least one desired antigen or other protein of interest on the surface of the membrane or at least partially embedded within the membrane. An example of a yeast cell wall preparation is a preparation of isolated yeast cell walls carrying an antigen on its surface or at least partially embedded within the cell wall such that the yeast cell wall preparation, when administered to a subject, stimulates a desired immune response against a disease target.

Any yeast strain can be used to produce a yeast vehicle of the present invention, or otherwise used as a host cell in the present invention. Yeast are unicellular microorganisms that belong to one of three classes: Ascomycetes, Basidiomycetes and Fungi Imperfecti. One consideration for the selection of a type of yeast for use as an immune modulator is the pathogenicity of the yeast. In one embodiment, the yeast is a non-pathogenic strain such as *Saccharomyces cerevisiae*. The selection of a non-pathogenic yeast strain minimizes any adverse effects to the individual to whom the yeast vehicle is administered. However, pathogenic yeast may be used if the pathogenicity of the yeast can be negated by any means known to one of skill in the art (e.g., mutant strains). In accordance with one aspect of the present invention, non-pathogenic yeast strains are used.

Genera of yeast strains that may be used in the invention include but are not limited to *Saccharomyces, Candida* (which can be pathogenic), *Cryptococcus, Hansenula, Kluyveromyces, Pichia, Rhodotorula, Schizosaccharomyces* and *Yarrowia*. In one aspect, yeast genera are selected from *Saccharomyces, Candida, Hansenula, Pichia* or *Schizosaccharomyces*, and in one aspect, *Saccharomyces* is used. Species of yeast strains that may be used in the invention include but are not limited to *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus* var. *lactis, Pichia pastoris, Rhodotorula rubra, Schizosaccharomyces pombe*, and *Yarrowia hpolytica*. It is to be appreciated that a number of these species include a variety of subspecies, types, subtypes, etc. that are intended to be included within the aforementioned species. In one aspect, yeast species used in the invention include *S. cerevisiae, C. albicans, H. polymorpha, P. pastoris* and *S. pombe*. *S. cerevisiae* is useful as it is relatively easy to manipulate and being "Generally Recognized As Safe" or "GRAS" for use as food additives (GRAS, FDA proposed Rule 62FR18938, Apr. 17, 1997). One embodiment of the present invention is a yeast strain that is capable of replicating plasmids to a particularly high copy number, such as a *S. cerevisiae* cir° strain. The *S. cerevisiae* strain is one such strain that is capable of supporting expression vectors that allow one or more target antigen(s) and/or antigen fusion protein(s) and/or other proteins to be expressed at high levels. Another yeast strain is useful in the invention is *Saccharomyces cerevisiae* W303α. In addition, any mutant yeast strains can be used in the present invention, including those that exhibit reduced post-translational modifications of expressed target antigens or other proteins, such as mutations in the enzymes that extend N-linked glycosylation. In one aspect of the invention, a yeast-based immunotherapy composition is produced using a mutant yeast strain that produces the MUC1 antigen as an underglycosylated protein as compared to the same antigen produced by the wild-type strain (with normal glycosylation). Such a MUC1 antigen may be more similar to MUC1 antigens expressed by tumor cells, which can then be processed into unique T cell epitopes by antigen presenting cells, thus enhancing the specific anti-tumor response.

In general, the yeast vehicle and antigen(s) and/or other agents can be associated by any technique described herein. In one aspect, the yeast vehicle is loaded intracellularly with the antigen(s) and/or other or additional agent(s) to be included in the composition. In another aspect, the antigen(s) and/or agent(s) is covalently or non-covalently attached to the yeast vehicle. In yet another aspect, the yeast vehicle and the antigen(s) and/or agent(s) are associated by mixing. In another aspect, the antigen(s) and/or agent(s) are expressed recombinantly by the yeast vehicle or by the yeast cell or yeast spheroplast from which the yeast vehicle is derived (if the yeast vehicle is other than a whole intact cell or a spheroplast).

In one embodiment, a yeast cell used to prepare the yeast vehicle is transfected with a heterologous nucleic acid molecule encoding a peptide or polypeptide (e.g., the antigen) such that the peptide or polypeptide is expressed by the yeast cell. Such a yeast also is referred to herein as a recombinant yeast or a recombinant yeast vehicle. The yeast cell can then be formulated with a pharmaceutically acceptable excipient and administered directly to an individual, stored for later administration to an individual, or loaded into a dendritic cell, which can then in turn be administered to an individual. The yeast cell also can be killed, or it can be derivatized such as by formation of yeast spheroplasts, cytoplasts, ghosts, or subcellular particles, any of which may be followed by storing, administering directly to an individual, or loading of the cell or derivative into a dendritic cell. Yeast spheroplasts can also be directly transfected with a recombinant nucleic acid molecule (e.g., the spheroplast is produced from a whole yeast, and then transfected) in order to produce a recombinant spheroplast that expresses the antigen. Yeast cells or yeast spheroplasts that recombinantly express the antigen(s) may be used to produce a yeast vehicle comprising a yeast cytoplast, a yeast ghost, or a yeast membrane particle or yeast cell wall particle, or fraction thereof.

A number of antigens and/or other proteins to be produced by a yeast vehicle of the present invention is any number of antigens and/or other proteins that can be reasonably produced by a yeast vehicle, and typically ranges from at least one to at least about 6 or more, including from about 2 to about 6 antigens and or other proteins.

Expression of an antigen or other proteins in a yeast vehicle of the present invention is accomplished using techniques known to those skilled in the art. Briefly, a nucleic acid molecule encoding at least one desired antigen or other protein is inserted into an expression vector in such a manner that the nucleic acid molecule is operatively linked to a transcription control sequence in order to be capable of effecting either constitutive or regulated expression of the nucleic acid molecule when transformed into a host yeast cell. Nucleic acid molecules encoding one or more antigens and/or other proteins can be in one or more expression vectors operatively linked to one or more expression control sequences. Particularly important expression control sequences are those which control transcription initiation, such as promoter and upstream activation sequences. Promoters suitable for use in yeast have been described above.

Transfection of a nucleic acid molecule into a cell (e.g., yeast cell) according to the present invention can be accomplished by any method by which a nucleic acid molecule can be introduced into the cell and includes, but is not limited to, diffusion, active transport, bath sonication, electroporation, microinjection, lipofection, adsorption, and protoplast fusion. Transfected nucleic acid molecules can be integrated into a yeast chromosome or maintained on extrachromosomal vectors using techniques known to those skilled in the art. Examples of yeast vehicles carrying such nucleic acid molecules are disclosed in detail herein. As discussed above, yeast cytoplast, yeast ghost, and yeast membrane particles or cell wall preparations can also be produced recombinantly by transfecting intact yeast microorganisms or yeast spheroplasts with desired nucleic acid molecules, producing the antigen therein, and then further manipulating the microorganisms or spheroplasts using techniques known to those skilled in the art to produce cytoplast, ghost or subcellular yeast membrane extract or fractions thereof containing desired antigens or other proteins.

Effective conditions for the production of recombinant yeast vehicles and expression of the antigen and/or other protein by the yeast vehicle include an effective medium in which a yeast strain can be cultured. An effective medium is typically an aqueous medium comprising assimilable carbohydrate, nitrogen and phosphate sources, as well as appropriate salts, minerals, metals and other nutrients, such as vitamins and growth factors. The medium may comprise complex nutrients or may be a defined minimal medium. Yeast strains of the present invention can be cultured in a variety of containers, including, but not limited to, bioreactors, Erlenmeyer flasks, test tubes, microtiter dishes, and Petri plates. Culturing is carried out at a temperature, pH and oxygen content appropriate for the yeast strain. Such culturing conditions are well within the expertise of one of ordinary skill in the art (see, for example, Guthrie et al. (eds.), *Methods in Enzymology*, vol. 194, Academic Press, San Diego (1991)). For example, under one protocol, liquid cultures containing a suitable medium can be inoculated using cultures obtained from starter plates and/or starter cultures of yeast-based MUC1 immunotherapy compositions, and are grown for approximately 20 h at 30° C., with agitation at 250 rpm. Primary cultures can then be expanded into larger cultures as desired. Protein expression from vectors with which the yeast were transformed (e.g., MUC1 expression) may be constitutive if the promoter utilized is a constitutive promoter, or may be induced by addition of the appropriate induction conditions for the promoter if the promoter utilized is an inducible promoter (e.g., copper sulfate in the case of the CUP1 promoter). In the case of an inducible promoter, induction of protein expression may be initiated after the culture has grown to a suitable cell density, which may be at about 0.2 YU/ml or higher densities.

One non-limiting example of a medium suitable for the culture of a yeast-based immunotherapy composition of the invention is U2 medium. U2 medium comprises the following components: 15 g/L of glucose, 6.7 g/L of Yeast nitrogen base containing ammonium sulfate, and 0.04 mg/mL each of histidine, tryptophan, and adenine, and 0.06 mg/ml of leucine. Another non-limiting example of a medium suitable for the culture of yeast-based immunotherapy composition of the invention is UL2 medium. UL2 medium comprises the following components: 15 g/L of glucose, 6.7 g/L of Yeast nitrogen base containing ammonium sulfate, and 0.04 mg/mL each of histidine, tryptophan, and adenine.

In some embodiments of the invention, the yeast are grown under neutral pH conditions (sometimes also referred to as "DEC" or "Dec" conditions). As used herein, the general use of the term "neutral pH" refers to a pH range between about pH 5.5 and about pH 8, and in one aspect, between about pH 6 and about 8. One of skill the art will appreciate that minor fluctuations (e.g., tenths or hundredths) can occur when measuring with a pH meter. As such, the use of neutral pH to grow yeast cells means that the yeast cells are grown in neutral pH for the majority of the time that they are in culture. In one embodiment, yeast are grown in a medium maintained at a pH level of at least 5.5 (i.e., the pH of the culture medium is not allowed to drop below pH 5.5). In another aspect, yeast are grown at a pH level maintained at about 6, 6.5, 7, 7.5, or 8. In one aspect, neutral pH is maintained by using a suitable buffer to create a buffered culture or growth medium. The use of a neutral pH in culturing yeast promotes several biological effects that are desirable characteristics for using the yeast as vehicles for immunomodulation. For example, culturing the yeast in neutral pH allows for good growth of the yeast without negative effect on the cell generation time (e.g., slowing of doubling time). The yeast can continue to grow to high densities without losing their cell wall pliability. The use of a neutral pH allows for the production of yeast with pliable cell walls and/or yeast that are more sensitive to cell wall digesting enzymes (e.g., glucanase) at all harvest densities. This trait is desirable because yeast with flexible cell walls can induce different or improved immune responses as compared to yeast grown under more acidic conditions, e.g., by promoting the secretion of cytokines by antigen presenting cells that have phagocytosed the yeast (e.g., TH1-type cytokines including, but not limited to, IFN-γ, interleukin-12 (IL-12), and IL-2, as well as proinflammatory cytokines such as IL-6). In addition, greater accessibility to the antigens located in the cell wall is afforded by such culture methods. In another aspect, the use of neutral pH for some antigens allows for release of the di-sulfide bonded antigen by treatment with dithiothreitol (DTT) that is not possible when such an antigen-expressing yeast is cultured in media at lower pH (e.g., pH 5). In one non-limiting example of the use of neutral pH conditions to culture yeast for use in the present invention, UL2 medium described above is buffered using, for example, 4.2 g/L of Bis-Tris.

In one embodiment, control of the amount of yeast glycosylation is used to control the expression of antigens by the yeast, particularly on the surface. The amount of yeast glycosylation can affect the immunogenicity and antigenicity of the antigen, particularly one expressed on the surface, since sugar moieties tend to be bulky. As such, the existence of sugar moieties on the surface of yeast and its impact on the three-dimensional space around the target antigen(s) should be considered in the modulation of yeast according to the invention. Any method can be used to reduce or increase the amount of glycosylation of the yeast, if desired. For example, one could use a yeast mutant strain that has been selected to have low glycosylation (e.g., mnn1, och1 and mnn9 mutants), or one could eliminate by mutation the glycosylation acceptor sequences on the target antigen. Alternatively, one could use yeast with abbreviated glycosylation patterns, e.g., *Pichia*. One can also treat the yeast using methods that reduce or alter the glycosylation.

In one embodiment of the present invention, as an alternative to expression of an antigen recombinantly in the yeast vehicle, a yeast vehicle is loaded intracellularly with the polypeptide (protein) or peptide and/or other molecules that serve as an antigen and/or are useful as immunomodulatory agents or biological response modifiers according to the invention. Subsequently, the yeast vehicle, which now contains the antigen and/or other proteins intracellularly, can be administered to an individual or, alternatively, loaded into a carrier such as a dendritic cell, which may in turn be administered to an individual. Peptides and proteins can be inserted directly into yeast vehicles of the present invention by techniques known to those skilled in the art, such as by diffusion, active transport, liposome fusion, electroporation, phagocytosis, freeze-thaw cycles, and bath sonication. Yeast vehicles that can be directly loaded with peptides, proteins, carbohydrates, or other molecules include intact yeast, as well as spheroplasts, ghosts or cytoplasts, which can be loaded with antigens and other agents after production. Alternatively, intact yeast can be loaded with the antigen and/or agent, and then spheroplasts, ghosts, cytoplasts, or subcellular particles can be prepared therefrom. Any number of antigens and/or other agents can be loaded into a yeast vehicle in this embodiment, from at least 1, 2, 3, 4 or any whole integer up to hundreds or thousands of antigens and/or other agents, such as would be provided by the loading of a microorganism or portions thereof, for example.

In another embodiment of the present invention, an antigen and/or other agent is physically attached to the yeast vehicle. Physical attachment of the antigen and/or other agent to the yeast vehicle can be accomplished by any method suitable in the art, including covalent and non-covalent association methods which include, but are not limited to, chemically crosslinking the antigen and/or other agent to the outer surface of the yeast vehicle or biologically linking the antigen and/or other agent to the outer surface of the yeast vehicle, such as by using an antibody or other binding partner. Chemical cross-linking can be achieved, for example, by methods including glutaraldehyde linkage, photoaffinity labeling, treatment with carbodiimides, treatment with chemicals capable of linking di-sulfide bonds, and treatment with other cross-linking chemicals standard in the art. Alternatively, a chemical can be contacted with the yeast vehicle that alters the charge of the lipid bilayer of yeast membrane or the composition of the cell wall so that the outer surface of the yeast is more likely to fuse or bind to antigens and/or other agent having particular charge characteristics. Targeting agents such as antibodies, binding peptides, soluble receptors, and other ligands may also be incorporated into an antigen as a fusion protein or otherwise associated with an antigen for binding of the antigen to the yeast vehicle.

When the antigen or other protein is expressed on or physically attached to the surface of the yeast, spacer arms may, in one aspect, be carefully selected to optimize antigen or other protein expression or content on the surface. The size of the spacer arm(s) can affect how much of the antigen or other protein is exposed for binding on the surface of the yeast. Thus, depending on which antigen(s) or other protein(s) are being used, one of skill in the art will select a spacer arm that effectuates appropriate spacing for the antigen or other protein on the yeast surface. In one embodiment, the spacer arm is a yeast protein of at least 450 amino acids. Spacer arms have been discussed in detail above.

In yet another embodiment, the yeast vehicle and the antigen or other protein are associated with each other by a more passive, non-specific or non-covalent binding mechanism, such as by gently mixing the yeast vehicle and the antigen or other protein together in a buffer or other suitable formulation (e.g., admixture).

In one embodiment, intact yeast (with or without expression of heterologous antigens or other proteins) can be ground up or processed in a manner to produce yeast cell wall preparations, yeast membrane particles or yeast fragments (i.e., not intact) and the yeast fragments can, in some embodiments, be provided with or administered with other compositions that include antigens (e.g., DNA vaccines, protein subunit vaccines, killed or inactivated pathogens, viral vector vaccines) to enhance immune responses. For example, enzymatic treatment, chemical treatment or physical force (e.g., mechanical shearing or sonication) can be used to break up the yeast into parts that are used as an adjuvant.

In one embodiment of the invention, yeast vehicles useful in the invention include yeast vehicles that have been killed or inactivated. Killing or inactivating of yeast can be accomplished by any of a variety of suitable methods known in the art. For example, heat inactivation of yeast is a standard way of inactivating yeast, and one of skill in the art can monitor the structural changes of the target antigen, if desired, by standard methods known in the art. Alternatively, other methods of inactivating the yeast can be used, such as chemical, electrical, radioactive or UV methods. See, for example, the methodology disclosed in standard yeast culturing textbooks such as *Methods of Enzymology*, Vol. 194, Cold Spring Harbor Publishing (1990). Any of the inactivation strategies used should take the secondary, tertiary or quaternary structure of the target antigen into consideration and preserve such structure as to optimize its immunogenicity.

Yeast vehicles can be formulated into yeast-based immunotherapy compositions or products of the present invention using a number of techniques known to those skilled in the art. For example, yeast vehicles can be dried by lyophilization. Formulations comprising yeast vehicles can also be prepared by packing yeast in a cake or a tablet, such as is done for yeast used in baking or brewing operations. In addition, yeast vehicles can be mixed with a pharmaceutically acceptable excipient, such as an isotonic buffer that is tolerated by a host or host cell. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity-enhancing agents, such as sodium carboxymethylcellulose, sorbitol, glycerol or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise, for example, dextrose, human serum albumin, and/or preservatives to which sterile water or saline can be added prior to administration.

The peptide, polypeptide, nucleic acid, vector, or cell can be isolated. The term "isolated" as used herein encompasses compounds or compositions that have been removed from a biological environment (e.g., a cell, tissue, culture medium, body fluid, etc.) or otherwise increased in purity to any degree (e.g., isolated from a synthesis medium). Isolated compounds and compositions, thus, can be synthetic or naturally produced.

The peptide, polypeptide, nucleic acid, vector, or cell can be formulated as a composition (e.g., pharmaceutical composition) comprising the peptide, polypeptide, nucleic acid, vector, or cell and a carrier (e.g., a pharmaceutically or physiologically acceptable carrier). Furthermore, the peptide, polypeptide, nucleic acid, vector, cell, or composition of the invention can be used in the methods described herein alone or as part of a pharmaceutical formulation.

The composition (e.g., pharmaceutical composition) can comprise more than one peptide, polypeptide, nucleic acid, vector, or cell or composition of the invention. Vectors and compositions of the invention can further include or can be administered with (concurrently, sequentially, or intermittently with) any other agents or compositions or protocols that are useful for preventing or treating cancer or any compounds that treat or ameliorate any symptom of cancer, and particularly cancers associated with MUC1 expression or overexpression. For example, the composition can comprise one or more other pharmaceutically active agents or drugs. Examples of such other pharmaceutically active agents or drugs that may be suitable for use in the pharmaceutical composition include anticancer agents (e.g., chemotherapeutic or radiotherapeutic agents), antimetabolites, hormones, hormone antagonists, antibiotics, antiviral drugs, antifungal drugs, cyclophosphamide, and combinations thereof. Suitable anticancer agents include, without limitation, alkylating agents, folate antagonists, purine antagonists, pyrimidine antagonists, spindle poisons, topoisomerase inhibitors, apoptosis inducing agents, angiogenesis inhibitors, podophyllotoxins, nitrosoureas, cisplatin, carboplatin, interferon, asparginase, tamoxifen, leuprolide, flutamide, megestrol, mitomycin, bleomycin, doxorubicin, irinotecan, taxol, geldanamycin (e.g., 17-AAG), and various anti-cancer peptides and antibodies known in the art.

Exemplary alkylating agents include, but are not limited to, nitrogen mustards (e.g., mechlorethamine, cyclophosphamide, melphalan, uracil mustard, or chlorambucil), alkyl sulfonates (e.g., busulfan), nitrosoureas (e.g., carmustine, lomustine, semustine, streptozocin, or dacarbazine). Exemplary antimetabolites include, but are not limited to, folic acid analogs (e.g., methotrexate), pyrimidine analogs (e.g., 5-fluorouracil (5-FU) or cytarabine), and purine analogs (e.g., mercaptopurine or thioguanine). Exemplary hormones and hormone antagonists include, but are not limited to, adrenocorticosteroids (e.g., prednisone), progestins (e.g., hydroxyprogesterone caproate, medroxyprogesterone acetate, and magestrol acetate), estrogens (e.g., diethylstilbestrol and ethinyl estradiol), antiestrogens (e.g., tamoxifen), and androgens (e.g., testosterone proprionate and fluoxymesterone). Other exemplary agents include, but are not limited to, vinca alkaloids (e.g., vinblastine, vincristine, or vindesine), epipodophyllotoxins (e.g., etoposide or teniposide), antibiotics (e.g., dactinomycin, daunorubicin, doxorubicin, bleomycin, plicamycin, or mitocycin C), enzymes (e.g., L-asparaginase), platinum coordination complexes (e.g., cis-diamine-dichloroplatinum II also known as cisplatin), substituted ureas (e.g., hydroxyurea), methyl hydrazine derivatives (e.g., procarbazine), and adrenocortical suppressants (e.g., mitotane and aminoglutethimide).

Chemotherapeutics that can be concurrently, sequentially or intermittently administered with the vectors and compositions disclosed herein include Adriamycin, Alkeran, Ara-C, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin, Enzalutamide (MDV-3100 or XTANDI™), and calcitriol. Exemplary immunomodulators and/or cytokines include, but are not limited to, AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, tumor necrosis factor (TNF)-α, and TNF-β.

Other agents, compositions or protocols (e.g., therapeutic protocols) that are useful for the treatment of cancer in conjunction with the peptides, polypeptides (proteins), nucleic acids, vectors, cells, and compositions of the invention include, but are not limited to, surgical resection of a tumor, radiation therapy, allogeneic or autologous stem cell transplantation, T cell adoptive transfer, and/or targeted cancer therapies (e.g., small molecule drugs, biologics, or monoclonal antibody therapies that specifically target molecules involved in tumor growth and progression, including, but not limited to, selective estrogen receptor modulators (SERMs), aromatase inhibitors, tyrosine kinase inhibitors, serine/threonine kinase inhibitors, histone deacetylase (HDAC) inhibitors, retinoid receptor activators, apoptosis stimulators, angiogenesis inhibitors, poly (ADP-ribose) polymerase (PARP) inhibitors, or immunostimulators).

The additional active agent (e.g., chemotherapeutics agent) can be administered before, concurrently with (including simultaneously), alternating with, sequentially, or after administration with the vectors and compositions disclosed herein. In certain embodiments, one or more (e.g., 2, 3, 4, or 5) chemotherapeutic agents is administered in combination with the vectors and compositions disclosed herein. For example, when given to an individual in conjunction with chemotherapy or a targeted cancer therapy, it may be desirable to administer the yeast-based immunotherapy compositions during the "holiday" between doses of chemotherapy or targeted cancer therapy, in order to maximize the efficacy of the immunotherapy compositions. Surgical resection of a tumor may frequently precede administration of a yeast-based immunotherapy composition, but additional or primary surgery may occur during or after administration of a yeast-based immunotherapy composition.

The additional active agent can be administered alone or in a composition. The additional active agent can be formulated by inclusion in a vector (e.g., plasmid or viral vector), in liposomes (tecemotide, which is also known as STIMUVAX™, L-BLP25, or BLP25 liposome vaccine), or in nanoparticles (e.g., VERSAMUNE™ nanotechnology).

The carrier can be any of those conventionally used and is limited only by physio-chemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular peptide, polypeptide, nucleic acid, vector, cell, or composition thereof of the invention and other active agents or drugs used, as well as by the particular method used to administer the peptide, polypeptide, nucleic acid, vector, cell, or composition thereof.

The composition additionally or alternatively can comprise one or more immunostimulatory/regulatory molecules. Any suitable immunostimulatory/regulatory molecule can be used, such as interleukin (IL)-2, IL-4, IL-6, IL-12, IL-15, IL-15/IL-15Ra, IL-15/IL-15Ra-Fc, interferon (IFN)-γ, tumor necrosis factor (TNF)-α, B7.1, B7.2, ICAM-1, ICAM-2, LFA-1, LFA-2, LFA-3, CD70, CD-72, RANTES, G-CSF, GM-CSF, OX-40L, 41 BBL, anti-CTLA-4, IDO inhibitor, anti-PDL1, anti-PD1, and combinations thereof. Preferably, the composition comprises a combination of B7.1, ICAM-1, and LFA-3 (also referred to as TRICOM). The one or more immunostimulatory/regulatory molecules can be administered in the form of a vector (e.g., a recombinant viral vector, such as a poxvirus vector) comprising a nucleic acid encoding one or more immunostimulatory/regulatory molecules. For example, the one or more immunostimulatory/regulatory molecules (e.g., IL-12) can be administered in the form of a DNA plasmid with or without chitosan. Alternatively, the one or more immunostimulatory/regulatory molecules can be administered as a protein (e.g., recombinant protein), such as a protein (e.g., recombinant IL-12) admixed with chitosan. One or more immunostimulatory/regulatory molecules also can be administered in combination with, or concurrently with, a yeast-based immunotherapy composition of the invention.

In one embodiment of the invention, the composition comprises a first recombinant vector comprising the nucleic acid encoding the inventive peptide or polypeptide (protein) and second recombinant vector comprising a nucleic acid encoding B7.1, ICAM-1, and LFA-3. In another embodiment, the nucleic acid encoding the inventive peptide or polypeptide (protein) and the nucleic acid encoding B7.1, ICAM-1, and LFA-3 are in the same recombinant vector. The first and/or second vectors additionally can comprise a nucleic acid encoding another tumor associated antigen (e.g., CEA), a modified version thereof (e.g., CEA-6D), or an epitope thereof.

For example, the recombinant vector can be an avipox vector (e.g., canarypox virus or a fowlpox virus) comprising the nucleic acid encoding the inventive peptide and nucleic acids encoding a B7-1 polypeptide, an ICAM-1 polypeptide, and an LFA-3 polypeptide. Alternatively, the recombinant vector can be an orthopox virus comprising the nucleic acid encoding the inventive peptide and nucleic acids encoding a B7-1 polypeptide, an ICAM-1 polypeptide, and an LFA-3 polypeptide.

In another embodiment of the invention, the composition comprises a yeast-based immunotherapy composition as described herein, wherein the yeast-based immunotherapy composition comprises a yeast vehicle and at least one antigen comprising the inventive peptide or polypeptide.

The invention provides a method of transducing dendritic cells with the peptide, polypeptide, nucleic acid, vector, cell, or composition thereof, and optionally immunostimulatory/regulatory molecules, such as for example, B7-1, ICAM-1 and LFA-3. In one aspect of the invention, dendritic cells transduced with the peptide, polypeptide, nucleic acid, vector, cell, or composition thereof are administered to the host generate an immune response, such as activation of a cytotoxic T cell response.

The invention provides methods of treating a subject suffering from or susceptible to a MUC1-expressing tumor and/or enhancing an immune response against a MUC1-expressing cancer and/or inhibiting a MUC-1 expressing cancer. In a first embodiment, the inventive methods comprise administering a therapeutically effective amount of one or more of the peptide, polypeptide, nucleic acid, vector, cell, or composition thereof to a subject. The inventive peptide, polypeptide, nucleic acid, vector, cell, or composition thereof can be used to prevent the development of a MUC1-expressing cancer, particularly in an individual at higher risk to develop such cancer than other individuals, or to treat a patient afflicted with a MUC1-expressing cancer. The inventive peptide, polypeptide, nucleic acid, vector, cell, or composition thereof is useful for preventing emergence of such cancers, arresting progression of such cancers or eliminating such cancers. More particularly, the inventive peptide, polypeptide, nucleic acid, vector, cell, or composition thereof can be used to prevent, inhibit or delay the development of MUC1-expressing tumors, and/or to prevent, inhibit or delay tumor migration and/or tumor invasion of other tissues (metastases) and/or to generally prevent or inhibit progression of cancer in an individual. The inventive peptide, polypeptide, nucleic acid, vector, cell, or composition thereof can also be used to ameliorate at least one symptom of the cancer, such as by reducing tumor burden in the individual; inhibiting tumor growth in the individual; increasing survival of the individual; and/or preventing, inhibiting, reversing or delaying progression of the cancer in the individual. The inventive peptide, polypeptide, nucleic acid, vector, cell, or composition thereof can be used to treat a subject with any stage MUC1-expressing cancer.

In a second embodiment, the inventive methods comprise obtaining (by isolating) dendritic cells from a subject, treating the dendritic cells with one or more of the therapeutically effective amount of the peptide, polypeptide, nucleic acid, vector, cell, or composition thereof, and administering the treated dendritic cells to the subject.

In a third embodiment, the inventive methods comprise (a) obtaining (isolating) peripheral blood mononuclear cells (PBMCs) from a subject, (b) isolating dendritic cells from the PBMCs, (c) treating the dendritic cells with one or more of the therapeutically effective amount of the peptide, polypeptide, nucleic acid, vector, cell, or composition thereof ex vivo, (d) activating the PBMCs with the treated dendritic cells ex vivo, and (e) administering the activated PBMCs to the subject.

In a fourth embodiment, the inventive methods comprise a method for inhibiting a MUC1-expressing cancer in a subject comprising (a) obtaining (isolating) PBMCs from a subject, (b) isolating dendritic cells from the PBMCs, (c) treating the dendritic cells with one or more of the therapeutically effective amount of the peptide, polypeptide, nucleic acid, vector, cell, or composition thereof ex vivo, (d) activating the PBMCs with the treated dendritic cells ex vivo, (e) isolating T lymphocytes from the activated PBMCs ex vivo, and (f) administering the isolated T lymphocytes to the subject.

The invention also provides the use of adoptively transferred T cells stimulated in vitro with one or more of the therapeutically effective amount of the peptide, polypeptide, nucleic acid, vector, cell, or composition thereof to inhibit a MUC1-expressing cancer in a subject.

Treatment (e.g., inhibiting a MUC-expressing cancer and/or enhancing an immune response against a MUC1-expressing cancer) comprises, but is not limited to, destroying tumor cells, reducing tumor burden, inhibiting tumor growth, reducing the size of the primary tumor, reducing the number of metastatic legions, increasing survival of the individual, delaying, inhibiting, arresting or preventing the onset or development of metastatic cancer (such as by delaying, inhibiting, arresting or preventing the onset of development of tumor migration and/or tumor invasion of tissues outside of primary cancer and/or other processes associated with metastatic progression of cancer), delaying or arresting primary cancer progression, improving immune responses against the tumor, improving long term memory immune responses against the tumor antigens, and/or improving the general health of the individual. It will be appreciated that tumor cell death can occur without a substantial decrease in tumor size due to, for instance, the presence of supporting cells, vascularization, fibrous matrices, etc. Accordingly, while reduction in tumor size is preferred, it is not required in the treatment of cancer.

The MUC1-expressing cancer can be any cancer expressing MUC1 including, but not limited to, human carcinomas (such as ovarian, breast, small intestine, stomach, kidney, bladder, uterus, testicular, pancreatic, colorectal, lung, thyroid, gastric, head and neck, prostate, esophageal, and other cancers of epithelial cell origin), including primary and metastatic cancers and hematologic malignancies such as lymphomas, leukemias and myelomas (e.g., multiple myeloma, chronic lymphocytic leukemia (CLL), multiple myelogenous lymphoma (MML), acute myeloid leukemia (AML), Epstein-Barr virus (EBV) transformed B cells, Burkitt's and Hodgkin's lymphomas and some B-cell non-Hodgkin's lymphomas).

The peptide, polypeptide, nucleic acid, vector, cell, or composition thereof can be administered to the host by any method. For example, the peptide, polypeptide, or nucleic acid encoding the peptide or polypeptide (e.g., as a vector) can be introduced into a cell (e.g., in a host) by any of various techniques, such as by contacting the cell with the peptide, polypeptide, the nucleic acid, or a composition comprising the nucleic acid as part of a construct, as described herein, that enables the delivery and expression of the nucleic acid. Specific protocols for introducing and expressing nucleic acids in cells are known in the art (see, e.g., Sambrook et al. (eds.), supra; and Ausubel et al., supra).

A yeast-based immunotherapy composition of the invention can be administered by various acceptable methods, including, but not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, intraarticular administration, intraventricular administration, inhalation (e.g., aerosol), intracranial, intraspinal, intraocular, aural, intranasal, oral, pulmonary administration, impregnation of a catheter, and direct injection into a tissue. In one aspect, routes of administration include: intravenous, intraperitoneal, subcutaneous, intradermal, intranodal, intramuscular, transdermal, inhaled, intranasal, oral, intraocular, intraarticular, intracranial, and intraspinal. Parenteral delivery can include intradermal, intramuscular, intraperitoneal, intrapleural, intrapulmonary, intravenous, subcutaneous, atrial catheter and venal catheter routes. Aural delivery can include ear drops, intranasal delivery can include nose drops or intranasal injection, and intraocular delivery can include eye drops. Aerosol (inhalation) delivery can also be performed using methods standard in the art (see, for example, Stribling et al., *Proc. Natl. Acad. Sci. USA,* 189: 11277-11281 (1992)). In one aspect, a yeast-based immunotherapeutic composition of the invention is administered subcutaneously. In one aspect, the yeast-based immunotherapeutic composition is administered directly into a tumor milieu.

Suitable methods of administering peptides, polypeptides (proteins), nucleic acids, vectors, cells, and compositions to hosts (subjects) are known in the art. The host (subject or individual) can be any suitable host, such as a mammal (e.g., a rodent, such as a mouse, rat, hamster, or guinea pig, rabbit, cat, dog, pig, goat, cow, horse, primate, or human).

For example, the peptide, polypeptide, nucleic acid, or vector (e.g., recombinant poxvirus) can be administered to a host by exposure of tumor cells to the peptide, polypeptide, nucleic acid, or vector ex vivo or by injection of the peptide, polypeptide, nucleic acid, or vector into the host. The peptide, polypeptide, nucleic acid, vector (e.g., recombinant poxvirus) or combination of vectors, cell, and composition can be directly administered (e.g., locally administered) by direct injection into the cancerous lesion or tumor or by topical application (e.g., with a pharmaceutically acceptable carrier).

The peptide, polypeptide, nucleic acid, vector, cell, or composition thereof can be administered alone or in combination with adjuvants, incorporated into liposomes (as described in, e.g., U.S. Pat. Nos. 5,643,599, 5,464,630, 5,059,421, and 4,885,172), incorporated into nanoparticles (e.g., VERSAMUNE™ nanotechnology), administered with cytokines, administered with biological response modifiers (e.g., interferon, interleukin-2 (IL-2), administered colony-stimulating factors (CSF, GM-CSF, and G-CSF), and/or administered other reagents in the art that are known to enhance immune response.

Examples of suitable adjuvants include alum, aluminum salts, aluminum phosphate, aluminum hydroxide, aluminum silica, calcium phosphate, incomplete Freund's adjuvant, saponins, such as QS21 (an immunological adjuvant derived from the bark of the South American tree *Quillaja saponaria Molina*), monophosphoryl lipid A (MLP-A), and RIBI DETOX™ adjuvant.

A particularly preferred adjuvant for use in the invention is the cytokine GM-CSF. GM-CSF has been shown to be an effective vaccine adjuvant because it enhances antigen processing and presentation by dendritic cells. Experimental and clinical studies suggest that recombinant GM-CSF can boost host immunity directed at a variety of immunogens.

GM-CSF can be administered using a viral vector (e.g., poxvirus vector) or as an isolated protein in a pharmaceutical formulation. GM-CSF can be administered to the host before, during, or after the initial administration of the peptide, polypeptide, nucleic acid, vector, cell, or composition thereof to enhance the antigen-specific immune response in the host. For example, recombinant GM-CSF protein can be administered to the host on each day of vaccination with the peptide, polypeptide, nucleic acid, vector, cell, or composition thereof and for each of the following 3 days (i.e. a total of 4 days). Any suitable dose of GM-CSF can be used. For instance, 50-500 μg (e.g., 100 μg, 200 μg, 300 μg, 400 μg, and ranges therebetween) of recombinant GM-CSF can be administered per day. The GM-CSF can be administered by any suitable method (e.g., subcutaneously) and, preferably, is administered at or near the site of the vaccination of a host with the peptide, polypeptide, nucleic acid, vector, cell, or composition thereof.

In one embodiment, the inventive peptide or polypeptide (protein) can be conjugated to helper peptides or to large carrier molecules to enhance the immunogenicity of the peptide or polypeptide. These molecules include, but are not limited to, influenza peptide, tetanus toxoid, tetanus toxoid CD4 epitope, *Pseudomonas* exotoxin A, poly-L-lysine, a lipid tail, endoplasmic reticulum (ER) signal sequence, and the like.

The inventive peptide or polypeptide (protein) also can be conjugated to an immunoglobulin molecule using art-accepted methods. The immunoglobulin molecule can be specific for a surface receptor present on tumor cells, but absent or in very low amounts on normal cells. The immunoglobulin also can be specific for a specific tissue (e.g., breast, ovarian, colon, or prostate tissue). Such a peptide-immunoglobulin conjugate or polypeptide-immunoglobulin conjugate allows for targeting of the peptide to a specific tissue and/or cell.

The peptide, polypeptide, nucleic acid, vector, cell, or composition thereof is administered to a host (e.g., mammal, such as a human) in an amount effective to generate a MUC1-specific immune response, preferably a cellular immune response. The efficacy of the peptide, polypeptide, nucleic acid, vector, or cell as an immunogen may be determined by in vivo or in vitro parameters as are known in the art. These parameters include but are not limited to antigen-specific cytotoxicity assays, regression of tumors expressing MUC1 or MUC1 epitopes, inhibition of cancer cells expressing MUC1 or MUC1 epitopes, production of cytokines, and the like.

Any suitable dose of the peptide, polypeptide, nucleic acid, vector, or cell or composition thereof can be administered to a host. The appropriate dose will vary depending upon such factors as the host's age, weight, height, sex, general medical condition, previous medical history, disease progression, and tumor burden and can be determined by a clinician. For example, the peptide can be administered in a dose of about 0.05 mg to about 10 mg (e.g., 0.1 mg, 0.5 mg, 1 mg, 2 mg, 3 mg, 4 mg, 5 mg, 6 mg, 7 mg, 8 mg, 9 mg, and ranges therebetween) per vaccination of the host (e.g., mammal, such as a human), and preferably about 0.1 mg to about 5 mg per vaccination. Several doses (e.g., 1, 2, 3, 4, 5, 6, or more) can be provided (e.g., over a period of weeks or months). In one embodiment a dose is provided every month for 3 months.

When the vector is a viral vector, a suitable dose can include about $1 \times 10^5$ to about $1 \times 10^{12}$ (e.g., $1 \times 10^6$, $1 \times 10^7$, $1 \times 10^8$, $1 \times 10^9$, $1 \times 10^{10}$, $1 \times 10^{11}$, and ranges therebetween) plaque forming units (pfus), although a lower or higher dose can be administered to a host. For example, about $2 \times 10^8$ pfus can be administered (e.g., in a volume of about 0.5 mL).

The inventive cells (e.g., cytotoxic T cells) can be administered to a host in a dose of between about $1 \times 10^5$ and $2 \times 10^{11}$ (e.g., $1 \times 10^6$, $1 \times 10^7$, $1 \times 10^8$, $1 \times 10^9$, $1 \times 10^{10}$, and ranges therebetween) cells per infusion. The cells can be administered in, for example, one to three (e.g., one, two, or three) infusions. In addition to the administration of the cells, the host can be administered a biological response modifier, such as interleukin 2 (IL-2). When the cells to be administered are cytotoxic T cells, the administration of the cytotoxic T cells can be followed by the administration of the peptide, polypeptide, nucleic acid, vector, or composition thereof in order to prime the cytotoxic T cells to further expand the T cell number in vivo.

In general, a suitable single dose of a yeast-based immunotherapeutic composition is a dose that is capable of effectively providing a yeast vehicle and the MUC1 antigen to a given cell type, tissue, or region of the patient body in an amount effective to elicit an antigen-specific immune response against one or more MUC1 antigens or epitopes, when administered one or more times over a suitable time period. For example, in one embodiment, a single dose of a Yeast-MUC1 of the present invention is from about $1 \times 10^5$ to about $5 \times 10^7$ yeast cell equivalents per kilogram body weight of the organism being administered the composition. One Yeast Unit (YU) is $1 \times 10^7$ yeast cells or yeast cell equivalents. In one aspect, a single dose of a yeast vehicle of the present invention is from about 0.1 YU ($1 \times 10^6$ yeast cells or yeast cell equivalents) to about 100 YU ($1 \times 10^9$ cells) per dose (i.e., per organism), including any interim dose, in increments of $0.1 \times 10^6$ cells (i.e., $1.1 \times 10^6$, $1.2 \times 10^6$, $1.3 \times 10^6$, etc.). In one embodiment, a suitable dose includes doses between 1 YU and 40 YU and, in one aspect, between 10 YU and 40 YU or between 10 YU and 80 YU In one embodiment, the doses are administered at different sites on the individual but during the same dosing period. For example, a 40 YU dose may be administered by injecting 10 YU doses to four different sites on the individual during one dosing period. The invention includes administration of an amount of the Yeast-MUC1 immunotherapy composition (e.g., 1, 2, 3, 4, 5, 6, 7, 8, 9 10, 11, 12, 13, 14, 15, 16, 17, 18, 19, 20 YU or more) at 1, 2, 3, 4, 5, 6, 7, 8, 9, 10, or more different sites on an individual to form a single dose.

When the cells to be administered are dendritic cells, the amount of dendritic cells administered to the subject will vary depending on the condition of the subject and should be determined via consideration of all appropriate factors by the practitioner. Preferably, about $1 \times 10^6$ to about $1 \times 10^{12}$ (e.g., about $1 \times 10^7$, about $1 \times 10^8$, about $1 \times 10^9$, about $1 \times 10^{10}$, or about $1 \times 10^{11}$ including ranges between of any of the cell numbers described herein) dendritic cells are utilized for adult humans. These amounts will vary depending on the age, weight, size, condition, sex of the subject, the type of tumor to be treated, the route of administration, whether the treatment is regional or systemic, and other factors. Those skilled in the art should be readily able to derive appropriate dosages and schedules of administration to suit the specific circumstance and needs of the subject.

The invention provides a method of generating peptide-specific cytotoxic T lymphocytes in vivo, ex vivo, or in vitro by stimulation of lymphocytes with an effective amount of the inventive peptide, polypeptide, nucleic acid, vector, or cell, alone or in a composition with one or more immunostimulatory/regulatory molecules and/or adjuvants or in a liposome formulation. The lymphocytes can be lymphocytes from any suitable source, e.g., peripheral blood, tumor tissues, lymph nodes, and effusions, such as pleural fluid or ascites fluid.

The MUC1 peptide specific cytotoxic T lymphocytes are immunoreactive with MUC1. Preferably, the cytotoxic T lymphocytes inhibit the occurrence of tumor cells and cancer and inhibit the growth of, or kill, tumor cells expressing MUC1 or epitopes thereof. The cytotoxic T lymphocytes, in addition to being antigen specific, can be MEW class I restricted. In one embodiment, the cytotoxic T lymphocytes are MEW class I HLA-A24 restricted. The cytotoxic T lymphocytes preferably have a $CD8^+$ phenotype.

In one embodiment, lymphocytes are removed from the host and stimulated ex vivo with the peptide, polypeptide, nucleic acid, vector, cell, or composition thereof to generate cytotoxic T lymphocytes. The cytotoxic T lymphocytes can be administered to the host in order to enhance an immune response to cancer, thereby inhibiting the cancer. Accordingly, the invention provides a method of inhibiting cancer in a host comprising (a) obtaining lymphocytes (e.g., from the host), (b) stimulating the lymphocytes with the peptide, polypeptide, nucleic acid, vector, cell, or composition thereof to generate cytotoxic T lymphocytes, and (c) administering the cytotoxic T lymphocytes to the host, wherein the cancer is inhibited.

In another embodiment, lymphocytes within the host are stimulated by administration to the host of the peptide, polypeptide, nucleic acid, vector, cell, or composition thereof to generate cytotoxic T lymphocytes, which cytotoxic T lymphocytes enhance an immune response to cancer, thereby inhibiting the cancer.

The invention includes a prime and boost protocol. In particular, in one embodiment related to peptides, polypeptides, and vectors of the invention, the protocol includes an initial "prime" with a composition comprising one or more recombinant vectors encoding the inventive peptide or polypeptide and optionally one or more immunostimulatory/ regulatory molecules and/or other tumor-associated antigens (e.g., CEA), modified versions thereof, and immunogenic epitopes thereof, followed by one or preferably multiple "boosts" with a composition containing the inventive peptide or polypeptide or one or more poxvirus vectors encoding the inventive peptide or polypeptide and optionally one or more immunostimulatory/regulatory molecules and/or other tumor-associated antigens (e.g., CEA), modified versions thereof, and immunogenic epitopes thereof.

In this embodiment, the initial priming vaccination can comprise one or more vectors. In one embodiment, a single vector (e.g., poxvirus vector) is used for delivery of the inventive peptide and one or more immunostimulatory/regulatory molecules and/or other tumor-associated antigens (e.g., CEA), modified versions thereof, and immunogenic epitopes thereof. In another embodiment, two or more vectors (e.g., poxvirus vectors) comprise the priming vaccination, which are administered simultaneously in a single injection.

The boosting vaccinations also can comprise one or more vectors (e.g., poxvirus vectors). In one embodiment, a single vector is used for delivery of the inventive peptide and the one or more immunostimulatory/regulatory molecules and/or other tumor-associated antigens (e.g., CEA), modified versions thereof, and immunogenic epitopes thereof of the boosting vaccination. In another embodiment, two or more vectors comprise the boosting vaccination, which are administered simultaneously in a single injection.

Different vectors (e.g., poxvirus vectors) can be used to provide a heterologous prime/boost protocol using vectors carrying different sets of therapeutic molecules for inoculations at different time intervals. For example, in one heterologous prime/boost combination, a first orthopox vector composition is used to prime, and a second avipox vector composition is used to boost.

The schedule for administration of the vectors (e.g., poxvirus vectors) typically involves repeated administration of the boosting vector. The boosting vector can be administered 1-3 times (e.g., 1, 2, or 3 times) at any suitable time period (e.g., every 2-4 weeks) for any suitable length of time (e.g., 6-12 weeks for a total of at least 5 to 15 boosting vaccinations). For example, the primary vaccination can comprise a recombinant vaccinia or MVA vector followed by multiple booster vaccinations with an avipox vector. In a particular embodiment, the host receives one vaccination with the priming vector, followed every 2 weeks thereafter with the boosting vector for 6 boosts, followed by every 4 weeks thereafter with the boosting vector, and continuing with the boosting vector for a period of time dependent on disease progression.

The present invention also includes the delivery (administration, immunization, vaccination) of a yeast-based immunotherapeutic composition of the invention to a subject or individual. The administration process can be performed ex vivo or in vivo, but is typically performed in vivo. Suitable routes of administration and suitable single doses for yeast-based immunotherapeutic compositions have been described above. Following an initial (original or priming) dose of a yeast-based immunotherapeutic composition, "boosters" or "boosts" of a yeast-based immunotherapeutic composition are administered, for example, when the immune response against the antigen has waned or as needed to provide an immune response or induce a memory response against a particular antigen or antigen(s). Boosters can be administered about 1, 2, 3, 4, 5, 6, 7, or 8 weeks apart, or monthly, bimonthly, quarterly, annually, and/or in a few or several year increments after the original administration (the priming dose), depending on the status of the individual being treated and the goal of the therapy at the time of administration (e.g., prophylactic, active treatment, maintenance). In one embodiment, an administration schedule is one in which doses of yeast-based immunotherapeutic composition is administered at least 1, 2, 3, 4, 5, 6, 7, 8, 9, 10, or more times over a time period of from weeks, to months, to years. In one embodiment, the doses are administered weekly or biweekly or triweekly or monthly for 1, 2, 3, 4, 5, 6, 7, 8, 9, 10 or more doses, followed by weekly, biweekly, triweekly or monthly doses as needed to achieve the desired preventative or therapeutic treatment for cancer. Additional boosters can then be given at similar or longer intervals (months or years) as a maintenance or remission therapy, if desired.

The invention further provides a kit that, in one embodiment, has at least a first recombinant vector (e.g., poxvirus vector) that has incorporated into its genome or portion thereof a nucleic acid encoding the inventive peptide or polypeptide in a pharmaceutically acceptable carrier. The first recombinant vector (e.g., poxvirus vectors) also can comprise one or more nucleic acids encoding one or more immunostimulatory/regulatory molecules and/or other tumor-associated antigens (e.g., CEA), modified versions thereof, and immunogenic epitopes thereof. In addition to the first recombinant vector, the kit can have a second recombinant vector that comprises one or more nucleic acids encoding one or more immunostimulatory/regulatory molecules and/or other tumor-associated antigens (e.g., CEA), modified versions thereof, and immunogenic epitopes thereof in a pharmaceutically acceptable carrier. The kit further provides containers, injection needles, and instructions on how to use the kit. In another embodiment, the kit further provides an adjuvant such as GM-CSF and/or instructions for use of a commercially available adjuvant with the kit components.

The invention also includes a kit comprising any of the yeast-based immunotherapeutic compositions described herein, or any of the individual components of such compositions described herein. Kits may include additional reagents and written instructions or directions for using any of the compositions of the invention to prevent or treat cancer associated with or characterized by MUC1 expression or overexpression.

As discussed above, the peptide, polypeptide, nucleic acid, vector, cell, or composition thereof can be administered to a host by various routes including, but not limited to, subcutaneous, intramuscular, intradermal, intraperitoneal, intravenous, and intratumoral. When multiple administrations are given, the administrations can be at one or more sites in a host and, in the case of yeast-based immunotherapy, a single dose can be administered by dividing the single dose into equal portions for administration at one, two, three, four or more sites on the individual.

Administration of the peptide, polypeptide, nucleic acid, vector, cell, or composition thereof can be "prophylactic" or "therapeutic." When provided prophylactically, the peptide, polypeptide, nucleic acid, vector, cell, or composition thereof is provided in advance of tumor formation, or the detection of the development of MUC1-expressing tumors, with the goal of preventing, inhibiting or delaying the development of MUC1-expressing tumors; and/or preventing, inhibiting or delaying metastases of such tumors and/or generally preventing or inhibiting progression of cancer in an individual, and generally to allow or improve the ability of the host's immune system to fight against a tumor that the host is susceptible of developing. For example, hosts with hereditary cancer susceptibility are a preferred group of patients treated with such prophylactic immunization. The prophylactic administration of the peptide, polypeptide, nucleic acid, vector, cell, or composition thereof prevents, ameliorates, or delays the MUC1-expressing cancer. When provided therapeutically, the peptide, polypeptide, nucleic acid, vector, cell, or composition thereof is provided at or after the diagnosis of the MUC1-expressing cancer, with the goal of ameliorating the cancer, such as by reducing tumor burden in the individual; inhibiting tumor growth in the individual; increasing survival of the individual; and/or preventing, inhibiting, reversing or delaying progression of the cancer in the individual.

When the host has already been diagnosed with the MUC1-expressing cancer or metastatic cancer, the peptide, polypeptide, nucleic acid, vector, cell, or composition thereof can be administered in conjunction with other therapeutic treatments such as chemotherapy, surgical resection of a tumor, treatment with targeted cancer therapy, allogeneic or autologous stem cell transplantation, T cell adoptive transfer, other immunotherapies, and/or radiation.

In a preferred embodiment, the administration of the peptide, polypeptide, nucleic acid, vector, cell, or composition thereof to a host results in a host cell expressing the inventive peptide and optionally one or more immunostimulatory/regulatory molecules and/or other tumor-associated antigens (e.g., CEA), modified versions thereof, and immunogenic epitopes thereof that were co-administered. The inventive peptide (i.e., MUC1 antigen) can be expressed at the cell surface of the infected host cell. The one or more immunostimulatory/regulatory molecules and/or other tumor-associated antigens (e.g., CEA), modified versions thereof, and immunogenic epitopes thereof can be expressed at the cell surface or may be actively secreted by the host cell. The expression of both the MUC1 antigen and the immunostimulatory/regulatory molecule provides the necessary MEW restricted peptide to specific T cells and the appropriate signal to the T cells to aid in antigen recognition and proliferation or clonal expansion of antigen specific T cells. The overall result is an upregulation of the immune system. Preferably, the upregulation of the immune response is an increase in antigen specific T-helper lymphocytes and/or cytotoxic lymphocytes, which are able to kill or inhibit the growth of a cancer (e.g., breast cancer, ovarian cancer, colon cancer, lung cancer, thyroid cancer, gastric cancer, head and neck cancer, or prostate cancer) cell.

There are a variety of suitable formulations of the pharmaceutical composition for the inventive methods. The following formulations for parenteral, subcutaneous, intravenous, intramuscular, and intraperitoneal administration are exemplary and are in no way limiting. One skilled in the art will appreciate that these routes of administering the peptide, polypeptide, nucleic acid, vector, cell, or composition of the invention are known, and, although more than one route can be used to administer a particular compound, a particular route can provide a more immediate and more effective response than another route.

Injectable formulations are among those formulations that are preferred in accordance with the present invention. The requirements for effective pharmaceutical carriers for injectable compositions are well-known to those of ordinary skill in the art (see, e.g., Pharmaceutics and Pharmacy Practice, J.B. Lippincott Company, Philadelphia, Pa., Banker and Chalmers, eds., pages 238-250 (1982), and ASHP Handbook on Injectable Drugs, Toissel, 4th ed., pages 622-630 (1986)).

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The peptide, polypeptide, nucleic acid, vector, cell, or composition thereof can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1, 3-dioxolane-4-methanol, ethers, such as poly(ethylene glycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, and synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-b-aminopropionates, and 2-alkyl-imidazoline quaternary ammonium salts, and (e) mixtures thereof.

Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Yeast-based immunotherapeutic compositions of the invention are most typically administered without adjuvant or other carriers and as an injectable formulation of the yeast-based composition in a simple pharmaceutically acceptable excipient, such as PBS or other buffer.

The following example further illustrates the invention but, of course, should not be construed as in any way limiting its scope.

Example 1

This example describes the analysis of HLA-A24 MUC1-C agonist epitopes.

I. Materials and Methods

Patients—PBMCs were used from two patients with prostate cancer enrolled in a previously described clinical trial of PSA-TRICOM vaccine in combination with ipilimumab (Madan et al., *Lancet Oncol.*, 13: 501-8 (2012)). An institutional review board of the National Institutes of Health (NIH) Clinical Center had approved the procedures, and informed consent was obtained in accordance with the Declaration of Helsinki.

Peptides—The MUC1 amino acid sequence was scanned for matches to consensus motifs for HLA-A24 binding peptides. The computer algorithm developed by Parker et al. to rank potential MHC-binding peptides according to the predicted one-half-time dissociation of peptide/MHC complexes was used (Parker et al., *J. Immunol.*, 152: 163-75 (1994)). American Peptide Company (Sunnyvale, Calif.) synthesized 9-mer and 10-mer peptide analogues from the MUC1-C region of MUC1 with single amino acid substitutions in order to increase binding affinity (Table 1). The purity of the peptides was >90%.

TABLE 1

MUC1 HLA-A24 binding peptides and potential agonists with predicted binding and T2-cell binding assay.

| Peptide | Position | Sequence^ | Predicted Binding* |
|---------|----------|-----------|--------------------|
| C6 | 462-471 | TYHPMSEYPT (SEQ ID NO: 3) | 6 |
| C6A | | KYHPMSEYAL (SEQ ID NO: 1) | 480 |
| C7 | 502-510 | SYTNPAVAA (SEQ ID NO: 4) | 5 |
| C7A | | KYTNPAVAL (SEQ ID NO: 2) | 400 |

^Amino acids that were changed to generate an agonist epitope are in bold.
*Predicted binding on the basis of reported motif (Parker et al., supra); score estimate of half time of disassociation of a molecule containing this sequence.

Affinity and avidity assays—Despite numerous attempts to establish binding assays for HLA-A24 peptides using T2-A24 cells, reliable assays could not be established. Therefore, these peptides were evaluated based solely on the ability to lyse cells pulsed with the corresponding peptide and tumor cells expressing the native peptide.

Establishment of T-cell lines—A modified version of the protocol described by Tsang et al., *J. Natl. Cancer Inst.*, 87: 982-90 (1995), was used to generate MUC1-specific CTLs. Irradiated autologous DCs were pulsed with 20 µg/mL of peptide for 2 hours, and then PBMCs were added at a 10:1 ratio. After 3 days, human IL-2 (20 Cetus units/mL) was added. Cells were restimulated every 7 days. After the third in vitro stimulation, cells were restimulated using autologous Epstein-Barr virus transformed B cells as antigen presenting cells at a ratio of 2:1, and maintained in medium containing IL-7 (10 ng/mL) and IL-15 (5 ng/mL).

Detection of cytokines—Autologous B cells pulsed with peptides at different concentrations (25, 12.5, 6.25 and 3, 13, and 1.56 µg/ml) were incubated with MUC1-specific T-cell lines at a 2:1 ratio for 24 hours. The supernatants were analyzed for IFN-γ by ELISA (Invitrogen, Frederick, Md.).

Tumor cell cultures—The pancreatic carcinoma cell line ASPC-1 (HLA-A3$^{neg}$, HLA-A24$^{neg}$, MUC1$^+$), colon cancer cell line SW620 (HLA-A24$^+$, MUC1$^+$), and prostate cancer cell line PC3 (HLA-A24$^+$, MUC1$^+$) were purchased from American Type Culture Collection (Manassas, Va.). All cell cultures were free of mycoplasma and maintained in complete medium (RPMI 1640 supplemented with 10% fetal calf serum, 100 U/mL penicillin, 100 µg/mL streptomycin, and 2 mM L-glutamine) (Mediatech, Herndon, Va.). K562-A2.1 cells were obtained from Dr. C. Britten (Johannes Gutenberg University, Mainz, Germany), and maintained in complete medium supplemented with 0.5 mg/mL of G418 (Mediatech, Manassas, Va.).

Cytotoxicity assay, cold target inhibition and antibody blocking of tumor cell lysis—To determine T-cell-mediated killing, a 16-hour $^{111}$Indium release assay was used (Tsang et al., *J. Natl. Cancer Inst.*, 87: 982-90 (1995)). 2×10$^6$ target cells were labeled with 60 µCi $^{111}$In oxide (GE Health Care, Vienna, Va.) at 37° C. for 20 minutes, and used at 3000 cells/well in 96-well round-bottom culture plates. T-cells were added at different ratios. All assays were performed in RPMI medium substituted with 10% human AB serum (Omega Scientific, Tarzana, Calif.), glutamine and antibiotics (Mediatech, Manassas, Va.). Spontaneous release was determined by incubating target cells with medium alone, and complete lysis was determined by incubation with 2.5% Triton X-100. Lysis was calculated using the formula:

$$\text{Lysis (\%)} = \frac{\text{observed release } (cpm) - \text{spontaneous release } (cpm)}{\text{complete release } (cpm) - \text{spontaneous release } (cpm)} \times 100$$

A cold target inhibition assay was performed by adding K562-A2.1 or K562-A3 cells, with or without prior pulsing with the corresponding peptide, at a ratio of 1:10 to the wells (Tsang et al., *J. Natl. Cancer Inst.*, 87: 982-90 (1995)). Antibody blocking was performed by pre-incubating tumor cells with 10 µg/ml of anti-HLA-A24 antibody or isotype control antibody (UPC10).

II. Analysis

The algorithm for HLA-A24 class I binding peptides in the MUC1-C region revealed no potential A24 binders. Changes in anchor residues revealed the potential for three HLA-A24 agonists. Studies were performed with two of these agonists (C6A and C7A, Table 1). The third potential agonist is not described since a T-cell line generated with the third potential agonist did not lyse tumor cells.

Attempts to generate T-cell lines with the native peptide designated C6 were unsuccessful using PBMCs from two different vaccinated cancer patients. T-cell lines, however, could be generated from these same patients using APCs pulsed with the corresponding agonist peptide C6A (SEQ ID NO: 1).

The T-cell line derived from APCs pulsed with the C6A peptide was evaluated for lysis versus two different MUC1$^+$, HLA-A24$^+$ tumor cell lines (SW620; colon cancer, and PC3; prostate cancer) and the ASPC-1 pancreatic cancer cell line (MUC1$^+$, HLA-A24$^{neg}$). Lysis of both of the HLA-A24$^+$ cell lines was observed (see Table 2) in contrast to the HLA-A24$^{neg}$ line.

TABLE 2

MUC1 native and agonist epitope-specific T-cell lines lyse tumor cells expressing native MUC1 and HLA-A24.

| T-cell Line | E:T Ratio | SW620 MUC1+HLA-A24+ | PC3 MUC1+HLA-A24+ | ASPC-1 MUC1+HLA-A24$^{neg}$ |
|---|---|---|---|---|
| T-C6 | 25:1 | NA | NA | NA |
|  | 12.5:1 | NA | NA | NA |
| T-C6A | 25:1 | 41.2 | 35.5 | 2.4 |
|  | 12.5:1 | 26.0 | 22.8 | 1.9 |
| T-C7 | 25:1 | 22.2 | NA | 0 |
|  | 12.5:1 | 13.7 | NA | NA |
| T-C7A | 25:1 | 41.9 | 22.6 | 3.4 |
|  | 12.5:1 | 32.6 | NA | 2.1 |

Results are expressed as percent (%) specific lysis. The assays were performed at 2 effector (E)-to-target (T) ratios.
NA: not available.

The T-cell line derived with the native C7 peptide grew poorly, but enough cells were available to evaluate this T-cell line in a cytotoxicity assay using the colon cancer cell line SW620. As can be seen in Table 3, the T-cell line derived with the agonist C7A peptide lysed SW620 cells more efficiently than the T-cell line derived with the native C7 peptide. Neither T-cell line lysed the ASPC-1 tumor cell line. The addition of an anti-HLA-A24 antibody greatly reduced the lysis of tumor cells, thereby demonstrating the MHC restriction of the lysis for both the C6A and C7A specific T-cell lines (Table 3).

TABLE 3

MUC1 HLA-A24 agonist epitope-specific T-cell lines lyse tumor cell lines expressing native MUC1 in an HLA-restricted manner.

| T-cell line | Blocking | % Lysis of SW620 MUC1+HLA-A24+ | % Lysis of PC3 MUC1+HLA-A24+ |
|---|---|---|---|
| T-C6A | — | 41.2 | 22.8 |
|  | Anti-HLA-A24 | 14.6 | 10.2 |
|  | Isotype Control | 37.0 | 20.1 |
| T-C7A | — | 22.7 | 22.6 |
|  | Anti-HLA-A24 | 8.6 | 3.1 |
|  | Isotype Control | 17.9 | 19.7 |

Results are expressed as % specific lysis. The assays were performed at an E:T ratio of 25:1 except the T-C6A lysis of PC3 cells, which was performed at an E:T ratio of 12.5:1.

Stimulation of the T-cell line generated with the C6A agonist peptide produced high levels (pg/mL/10$^5$ cells) of IFN-γ (2,651), GM-CSF (>10,000), IL-8 (>10,000), and TNF-α (372), and low levels (<50) of IL-2, IL-6, IL-10, and IL-12.

T-cell lines could be generated from the same patient using autologous APCs pulsed with the native C7 or agonist C7A peptides. Each cell line was then stimulated for 24 hours with B-cells pulsed with either the native C7 or agonist C7A peptide, and cytokine levels in the supernatant were analyzed.

As shown in Table 4, the T-cell line generated with the native peptide produced more Type I cytokine IFN-γ when simulated with the agonist C7A versus the native C7 peptide. Additionally, when the T-cell line generated with the agonist C7A peptide was stimulated with both native and agonist peptides, more IFN-γ, GM-CSF, IL-8, IL-10 and TNF-α was produced by stimulation with APCs pulsed with agonist C7A peptide versus the native C7 peptide (Table 4).

TABLE 4

MUC1 HLA-A24 agonist epitope-specific T-cell lines produce Type 1 cytokines upon stimulation.

| T-cell line | Peptide | IFN-γ | GM-CSF | IL-2 | TNFα | IL-8 | IL-6 | IL-10 |
|---|---|---|---|---|---|---|---|---|
| T-C6A | C6A | 3060 | 1277 | 3630 | 1021 | 11.8 | 7.6 | 16.4 |
| T-C7 | C7 | 750 | 237 | <2.4 | 21 | 6.8 | 6.4 | 25 |
|  | C7A | 1279 | 300 | <2.4 | 30 | 7.3 | 7.7 | 45 |
| T-C7A | C7 | 680 | 215 | <2.4 | 30 | 112 | <2.4 | 92 |
|  | C7A | 2000 | 910 | <2.4 | 70 | 360 | 40 | 375 |

Results are expressed as pg/mL/2.5 × 10$^5$ T cells. For the T-C7 and T-C7A experiments, the levels of IL-12p70 and IL-1β were <100 pg/mL for the native and agonist epitopes.

The results of these studies support the therapeutic usefulness of agonist epitopes of MUC1-C in the context of the invention described herein, including the use of peptides alone, on dendritic cells, with classical or novel adjuvant formulation, or with a range of biologic adjuvants, or cytokines such as IL-12, GM-CSF, or IL-15. These agonist peptides can also be used to activate T cells in vitro in adoptive T-cell therapy approaches. The T-cell receptors directed against these agonist epitopes also can be used in genetically engineered T-cell adoptive transfer studies. Longer peptides or the MUC1 protein itself containing the agonist epitopes also can be employed as described herein. Finally, recombinant vector-based vaccines can be employed, which encode the MUC1 transgene and include the sequences for these agonist epitopes.

Example 2

This example demonstrates the production of a Yeast-based MUC1 agonist immunotherapeutic composition comprising SEQ ID NO: 1 and known as GI-6108.

Yeast (*Saccharomyces cerevisiae*) were engineered to express a human MUC1 agonist antigen under the control of the copper-inducible promoter, CUP1, producing a yeast-MUC1 agonist immunotherapy composition. The MUC1 agonist antigen comprises the enhancer agonist peptide of SEQ ID NO: 1, and was designed using a full-length wild-type MUC1 antigen having Accession No. NP_001191214 (SEQ ID NO: 14) although other wild-type MUC1 proteins could be utilized to design similar agonists.

Briefly, a fusion protein comprising a MUC1 agonist antigen was produced as a single polypeptide with the following sequence elements fused in frame from N- to C-terminus, represented by SEQ ID NO: 16: (1) an alpha factor leader sequence of SEQ ID NO: 17 (corresponding to positions 1-89 of SEQ ID NO:16); (2) a linker sequence of Thr-Ser (corresponding to positions 90-91 of SEQ ID NO: 16); (3) a full-length MUC1 agonist protein corresponding to a wild-type protein except for the introduction of 15 amino acid agonist substitutions and one inactivating substitution (corresponding to positions 92-566 of SEQ ID NO: 16) and (4) a hexapeptide histidine tag (corresponding to positions 567-572 of SEQ ID NO: 16). SEQ ID NO: 16 is encoded by the nucleotide sequence represented by SEQ ID NO: 15 (codon optimized for yeast expression). The alpha leader sequence (corresponding to positions 1-89 of SEQ ID NO: 16) could be substituted with a different N-terminal sequence designed to impart resistance to proteasomal degradation and/or stabilize expression, such as the peptide represented by SEQ ID NO: 19, or an N-terminal peptide from a different yeast alpha leader sequence such as SEQ ID NO: 18, or by a MUC1 signal sequence. The hexahistidine C-terminal tag is optional, and facilitates identification and/ or purification of the protein. As compared to the wild-type MUC1 protein used as a template, the sequence of SEQ ID NO: 16 contains the following amino acid substitutions: (substitution positions given with reference to SEQ ID NO: 16 with further reference in parentheses to the location of the substitution in a wild-type MUC1 represented by Accession No. NP 001191214 identified as SEQ ID NO: 14): T184L (position 93 in wild-type MUC1), A232Y (position 141 in wild-type MUC1), P233L (position 142 in wild-type MUC1), G240V (position 149 in wild-type MUC1), S241Y (position 150 in wild-type MUC1), T242L (position 151 in wild-type MUC1), A483Y (position 392 in wild-type MUC1), C495A (position 404 in wild-type MUC1), C497V (position 406 in wild-type MUC1), T513K (position 422 in wild-type MUC1), P521A (position 430 in wild-type MUC1), T522L (position 431 in wild-type MUC1), T535L (position 444 in wild-type MUC1), D536F (position 445 in wild-type MUC1), and S551Y (position 460 in wild-type MUC1). The substitution C495A (position 404 in the wild-type MUC1 protein) is the inactivating mutation; the remainder of the substitutions are to produce agonist epitopes. SEQ ID NO: 16 comprises the enhancer agonist peptide referred to herein as SEQ ID NO: 1. SEQ ID NO: 1 is located at positions 513-522 of SEQ ID NO: 16. The yeast-based immunotherapy composition comprising the whole *Saccharomyces cerevisiae* yeast expressing the fusion protein of SEQ ID NO: 16 is referred to herein as GI-6108.

A plasmid containing MUC1 agonist antigen for GI-6108 was transfected into W303α yeast and transformants were selected after 3 days of growth at 30° C. on uridine dropout agar (UDA). Single colonies were re-streaked onto uridine and leucine dropout agar (ULDA) plates and incubated at 30° C. for an additional 4 days to select for cells with elevated plasmid copy number.

A single colony of GI-6108 was removed from the ULDA plate and used to inoculate 25 mL of UL2 liquid medium (starter culture). pH buffered UL2 medium containing 4.2 g/L of Bis-Tris (BT-UL2) also was inoculated with GI-6108 to evaluate this yeast-based immunotherapeutic produced under neutral pH manufacturing conditions (the resulting yeast referred to herein as "GI-6108-DEC"). Culturing in pH buffered UL2 medium exposes β-glucans on the yeast cell wall and is believed to modify the cellular immune responses induced by the yeast as a result of modifying the interactions with dectin receptors on antigen presenting cells. Accordingly, GI-6108 yeast are structurally and functionally different from GI-6108-DEC yeast. The starter cultures were incubated with shaking at 30° C. to a density of ~3 YU/mL, and then used to inoculate an intermediate culture to 0.3 YU/mL. The intermediate cultures were grown to a density of 3 YU/mL, and then used to inoculate final cultures to a density of 0.04 YU/mL. The final cultures were grown to a density of 3 YU/mL, and then treated with 0.5 mM copper sulfate for 3 h at 30° C. to induce MUC1 agonist antigen expression.

The induced cells were washed once with PBS, heat killed at 56° C. for 1 h, and then thrice washed in PBS. Total protein content of the heat killed cells was measured by Amidoschwarz assay and the agonist antigen content was measured by Western blot, with a monoclonal antibody recognizing a C-terminal hexahistidine epitope tag. Antigen quantity was determined by interpolation against a standard curve comprised of his tagged HCV NS3 protein.

Results showed that the GI-6108 yeast expressed the antigen well in the UL2 medium, and antigen content for GI-6108 was estimated to be approximately 2531 Ng/YU (data not shown). Expression of antigen by GI-6108-DEC yeast (i.e., GI-6108 grown in BT-UL2 medium, neutral pH conditions) was too low to result in accurate quantification by Western blot (data not shown). Nonetheless, both GI-6108 and GI-6108-DEC were used in the experiments described in Example 3.

Example 3

This example demonstrates that yeast-MUC1 immunotherapy compositions of the invention known as GI-6108 and GI-6108-DEC can activate MUC1-specific T cells.

T cell lines—T-3-P93L is a MUC-1 specific T cell line that specifically recognizes the MUC1 agonist peptide, denoted P93L, in the context of HLA-A2. P93L is a peptide spanning positions 92-101 of a full-length MUC1-C protein (e.g., ATWGQDVTSV, which corresponds to positions 92-101 of SEQ ID NO: 14) except that the threonine at position 2 of this peptide (position 93 of positions 92-101 of SEQ ID NO: 14) is substituted with a leucine, thereby creating an agonist peptide. P93L binds to HLA-A2 at higher levels than the native (wild-type) peptide, and is a better inducer of MUC1-specific T cells than the native peptide (higher production of TH1 cytokines) (see U.S. Patent Application Publication No. 2008/0063653). The T cell line T-3-P93L can specifically lyse HLA-A2-positive, MUC1-positive tumor targets in vitro. This T cell line is specific for a portion of MUC1 that is within the MUC1-N subunit.

C1A T cell is a MUC-1 specific T cell line that specifically recognizes the MUC1 agonist peptide, denoted C1A, in the context of HLA-A2. C1A is a peptide spanning positions 392-401 of a full-length MUC1 protein (e.g., ALAIVYLIAL, which corresponds to positions 392-401 of SEQ ID NO: 14) except that the alanine at position 1 of this peptide (position 392 of SEQ ID NO: 14) is substituted with a tyrosine, thereby creating an agonist peptide.

C2A T cell is a MUC-1 specific T cell line that specifically recognizes the MUC1 agonist peptide, denoted C2A, in the context of HLA-A2. C2A is a peptide spanning positions 397-406 of a full-length MUC1 protein (e.g., YLIALA-VCQC; which corresponds to positions 397-406 of SEQ ID NO: 14) except that the cysteine at position 10 of this peptide (position 406 of SEQ ID NO: 14) is substituted with a valine, thereby creating an agonist peptide.

C3A T cell is a MUC-1 specific T cell line that specifically recognizes the MUC1 agonist peptide, denoted C3A, in the context of HLA-A2. C3A is a peptide spanning positions 460-468 of a full-length MUC1 protein (e.g., SLSYTNPAV, which corresponds to positions 460-468 of SEQ ID NO: 14) except that the serine at position 1 of this peptide (position 460 in SEQ ID NO: 14) is substituted with a tyrosine, thereby creating an agonist peptide.

V1A T cell is a MUC-1 specific T cell line that specifically recognizes the MUC1 agonist peptide, denoted VNTR-3, in the context of HLA-A2. V1A is a peptide spanning positions 150-158 of a full-length MUC1 protein (e.g., STAPPAHGV, which corresponds to positions 150-158 of SEQ ID NO: 14) except that the serine at position 1 of this peptide (position 150 of SEQ ID NO: 14) is substituted with a tyrosine, and the threonine at position 2 of this peptide (position 151 of SEQ ID NO: 14) is substituted with a leucine, thereby creating an agonist peptide.

V2A T cell is a MUC-1 specific T cell line that specifically recognizes the MUC1 agonist peptide, denoted VNTR-5, in the context of HLA-A2. V2A is a peptide spanning positions 141-149 of a full-length MUC1 protein (e.g., APDTRPAPG, which corresponds to positions 141-149 of SEQ ID NO: 14) except that the alanine at position 1 of this peptide (position 141 of SEQ ID NO: 14) is substituted with a tyrosine, and the proline at position 2 of this peptide (position 142 of SEQ ID NO: 14) is substituted with a leucine, thereby creating an agonist peptide.

C5A T cell is a MUC-1 specific T cell line that specifically recognizes the MUC1 agonist peptide, denoted CSA, in the context of HLA-A3. C5A is a peptide spanning positions 443-451 of a full-length MUC1 protein (e.g., STDRSPYEK, which corresponds to positions 443-451 of SEQ ID NO: 14) except that the threonine at position 2 of this peptide (position 444 of SEQ ID NO: 14) is substituted with a leucine, and the aspartate at position 3 of this peptide (position 445 of SEQ ID NO: 14) is substituted with a phenylalanine, thereby creating an agonist peptide.

C6A T cell is a MUC-1 specific T cell line that specifically recognizes the MUC1 agonist peptide, denoted C6A, in the context of HLA-A24. C6A is a peptide spanning positions 422-431 of a full-length MUC1 protein (e.g., TYHPM-SEYPT; which corresponds to positions 422-431 of SEQ ID NO: 14) except that the threonine at position 1 of this peptide (position 422 of SEQ ID NO: 14) is substituted with a tyrosine, the proline at position 9 of this peptide (position 430 of SEQ ID NO: 14) is substituted with an alanine, and the threonine at position 10 of this peptide (position 431 of SEQ ID NO:14) is substituted with a leucine, thereby creating an agonist peptide. This T cell line also is described in Example 1.

A modified version of the protocol described by Tsang et al., *J. Natl. Cancer Inst.*, 87: 982-90 (1995), was used to generate MUC1-specific CTLs. Irradiated autologous DCs were pulsed with 20 µg/mL of peptide for 2 hours, and then PBMCs were added at a 10:1 ratio. After 3 days, human IL-2 (20 Cetus units/mL) was added. Cells were restimulated every 7 days. After the third in vitro stimulation (IVS), cells were restimulated using autologous Epstein-Barr virus transformed B cells as antigen presenting cells at a ratio of 2:1, and maintained in medium containing IL-7 (10 ng/mL) and IL-15 (5 ng/mL).

In a first experiment, dendritic cells (DCs) from a normal HLA-A2 human donor were cultured for 48 hours with: (1) medium alone (Medium); (2) GI-6106-DEC yeast (a positive control yeast-MUC1 immunotherapeutic composition grown under neutral pH conditions, previously described in PCT Publication No. WO 2013/024972); (3) GI-6108 yeast (a yeast-MUC1 immunotherapeutic composition of the invention described in Example 2 expressing a MUC1 antigen comprising HLA-A2, HLA-A3 and HLA-A24 agonist epitopes); (4) GI-6108-DEC (a yeast-MUC1 immunotherapeutic composition of the invention expressing a MUC1 antigen comprising HLA-A2, HLA-A3 and HLA-A24 agonist epitopes that was grown under neutral pH conditions also as described in Example 2); and (5) GI-Vec (Yeast Control), a yeast comprising an empty vector (no MUC1 antigen insert). Treated DCs then were used as antigen presenting cells (APCs) to evaluate their ability to stimulate the MUC1-specific, HLA-A2-restricted T cell lines P93L, C1A, C2A, C3A, V1A and V2A (T cell:DC ratio=10:1). A "no T cell" control was also included for each set of DCs. 24 hour culture supernatants were collected and screened for the secretion of interferon-γ (IFN-γ). The results are shown in Table 5, expressed as the amount of IFN-γ produced by the T cells in pg/ml.

TABLE 5

Production of IFN-γ by MUC1-specific HLA-A2 T cells stimulated with human DC (HLA-A2) treated with yeast-MUC1 agonist constructs (GI-6108 and GI-6108-DEC)

| DCs treated with: | P93L T cells | C1A T cells | C2A T cells | C3A T cells | V1A (VNTR-3) T cells | V2A (VNTR-5) T cells | No T cell |
|---|---|---|---|---|---|---|---|
| Medium | <15.6 | <15.6 | <15.6 | <15.6 | <15.6 | <15.6 | <15.6 |
| GI-6106-DEC (positive control) HLA-A2/A3 | 1572 | 103 | 1603 | 321 | 266 | 148 | <15.6 |
| GI-6108 HLA-A2/A3/A24 | 1528 | 50 | 1607 | 272 | 153 | 55 | <15.6 |
| GI-6108-DEC HLA-A2/A3/A24 | 1165 | 40 | 1514 | 147 | 81 | 75 | <15.6 |
| GI-Vec (Yeast Control) | <15.6 | 17 | <15.6 | <15.6 | 36 | 28 | <15.6 |

Ratio DCs:Yeast = 1:10. Results are expressed in pg/ml
$2 \times 10^4$ DCs: $2 \times 10^5$ T cells in 1 ml As shown in Table 5, dendritic cells treated with GI-6108, produced under both standard (GI-6108) and neutral pH conditions (GI-6108-DEC), and which express several different MUC1 agonist epitopes, were able to stimulate MUC1-specific, HLA-A2-restricted T cells to produce significant amounts of IFN-γ in a manner and at an level similar to the positive control.

In a second experiment, DCs from a normal HLA-A3 or HLA-A24 human donor were cultured for 48 hours with: (1) medium alone (Medium); (2) GI-6106-DEC yeast; (3) GI-6108 yeast; (4) GI-6108-DEC; and (5) GI-Vec (Yeast Control. Treated DCs were then used as APCs to evaluate their ability to stimulate the MUC1-specific HLA-A3-restricted T cell line C5A or the MUC1-specific HLA-A24-restricted T cell line C6A (T cell:DC ratio=10:1). A "no T cell" control was also included for each set of DCs. 24 hour culture supernatants were collected and screened for the secretion IFN-γ. The results are shown in Table 6, expressed as the amount of IFN-γ produced by the T cells in pg/ml.

TABLE 6

Production of IFN-γ by MUC1-specific T cells stimulated with human DC (HLA-A3/HLA-A24) treated with Yeast-MUC1 agonist constructs (GI-6108 and GI-6108-DEC)

| DCs treated with: | C5A (P483A) HLA-A3 T cell line | C6A (P-462A) HLA-A24 T cell line | No T cell |
|---|---|---|---|
| Medium | <15.6 | <15.6 | <15.6 |
| GI-6106-DEC (positive control) HLA-A2/A3 | 4230 | 1048 | <15.6 |
| GI-6108 HLA-A2/A3/A24 | 3664 | 2938 | <15.6 |
| GI-6108-DEC HLA-A2/A3/A24 | 3211 | 2590 | <15.6 |
| GI-Vec (Yeast Control) | <15.6 | <15.6 | <15.6 |

Ratio DCs:Yeast = 1:10. Results are expressed in pg/ml of IFN-γ $2 \times 10^4$ DCs: $2 \times 10^5$ T cells in 1 ml As shown in Table 6, dendritic cells treated with GI-6108, produced under both standard (GI-6108) and neutral pH conditions (GI-6108-DEC), and which express A3 and A24 MUC1 agonist epitopes, were able to stimulate both MUC1-specific, HLA-A3-restricted T cells and MUC1-specific HLA-A24-restricted T cells to produce significant amounts of IFN-γ in a manner and at an level similar to the positive control.

This data indicates that a MUC1-specific HLA-A24 T cell line established using MUC1 HLA-A24 agonist epitope C6A can be activated with human DC (HLA-A24 positive) treated with yeast-MUC1 agonist constructs (GI-6108 and GI-6108-DEC) containing HLA-A2/A3/A24 MUC1 agonist epitopes and produce high levels of IFN-γ. Additionally, this data indicates that the MUC1 HLA-A24 agonist epitope-specific T cell line can be activated by the native HLA-A24 epitope since GI-6106-DEC vector does not contain the HLA-A24 MUC1 agonist epitope.

Example 4

This example describes a phase 1 clinical trial in subjects with MUC1-positive cancer.

An open-label, dose-escalation phase 1 clinical trial is run using a yeast-MUC1 immunotherapy composition known as GI-6108 described in Example 2 (grown either under standard growth conditions or under neutral pH conditions). 12-24 subjects with a MUC1-positive tumor that can be HLA-A2, HLA-A3, or HLA-A24 positive are administered the yeast-MUC1 immunotherapy composition in a sequential dose cohort escalation protocol utilizing dose ranges of 4 YU (1 YU×4 sites), 16 YU (4 YU×4 sites), 40 YU (10 YU×4 sites), and 80 YU (20 YU×4 sites) administered subcutaneously. The yeast-MUC1 immunotherapy is administered at 2 week intervals for 3 months, and then monthly, or is administered monthly. An expansion cohort of patients (n=10) at maximum tolerated dose (MTD) or the observed best dose are selected for additional study. The results monitor safety as a primary endpoint, and as secondary endpoints, antigen-specific T cell responses (e.g., MUC1-specific CD8+ T cells emerging or expanding on treatment) as well as clinical activity.

GI-6108 is expected to be safe and well-tolerated with no significant toxicities. In addition, GI-6108 is expected to produce treatment-emergent MUC1-specific T cell responses or an improvement in pre-existing MUC1-specific baseline T cell responses in a statistically significant number of patients. Some patients are also expected to have stabilized disease.

Example 5

This example demonstrates that HLA-A24 agonist epitopes of MUC1-C can activate MUC1-specific cells.

A MUC1-specific HLA-A24 T cell line established using MUC1 HLA-A24 agonist epitope C6A was activated with HLA-A24 positive human DC transfected with poxvirus (MVA) vectors containing MUC1 HLA-A2/A3 MUC1 agonist epitopes (MVA-mBN-CV301). In particular, the human DC were treated with 10 MOI of either (1) MVA-mBN336 clone 73 or (2) MVA-mBN336 clone 77 and high levels of IFN-γ were produced (see Table 7).

TABLE 7

MUC1 HLA-A24 agonist epitope (C6A)-specific T cells can be activated with human DC (HLA-A24 positive) transfected with MVA-mBN-CV-301 vectors and produce high levels of IFN-γ

| DCs treated with: | MUC1 HLA-A24 agonist epitope (C6A)-specific T cell line | No T cell |
|---|---|---|
| Medium | 33.0 | <15.6 |
| MVA-mBN336 clone 73 (containing MUC1 HLA-A2/A3 agonist epitopes and native HLA-A24 epitope) | 1034 | 24.6 |
| MVA-mBN336 clone 77 (containing MUC1 HLA-A2/A3 agonist epitopes and native HLA-A24 epitope) | 996 | 22.4 |

Results are expressed in pg/ml of IFN-γ 2 × 10$^4$ DCs: 2 × 10$^5$ T cells in 1 ml As shown in Table 7, MUC1 HLA-A24 agonist epitope-specific T cell lines can be activated by the native HLA-A24 epitope since MVA-mBN-CV301 vectors do not contain the HLA-A24 MUC1 agonist epitope.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A yeast-MUC1 immunotherapeutic composition, wherein the immunotherapeutic composition comprises:
   (a) a yeast vehicle; and
   (b) a fusion protein comprising at least one MUC1 antigen, wherein the MUC1 antigen has an amino acid sequence that differs from the amino acid sequence of a wild-type MUC1 protein comprising SEQ ID NO:14 by at least one amino acid substitution at a sequence position, with respect to the wild-type MUC1 amino acid sequence, selected from the group consisting of: T93, A141, P142, G149, S150, and T151, and wherein the fusion protein has been expressed by the yeast vehicle.

2. The Yeast-MUC1 immunotherapeutic composition of claim 1, wherein the yeast vehicle is a whole yeast.

3. The Yeast-MUC1 immunotherapeutic composition of claim 1, wherein the yeast vehicle has been heat-inactivated.

4. The Yeast-MUC1 immunotherapeutic composition of claim 1, wherein the yeast vehicle is from *Saccharomyces cerevisiae*.

5. The Yeast-MUC1 immunotherapeutic composition of claim 1, wherein the MUC1 antigen has an amino acid sequence that differs from the amino acid sequence of the wild-type MUC1 protein having SEQ ID NO:14, by at least one amino acid substitution at a sequence position, with respect to the wild-type MUC1 amino acid sequence, selected from the group consisting of: T93L, A141Y, P142L, G149V, S150Y, and T151L.

6. The Yeast-MUC1 immunotherapeutic composition of claim 1, wherein the immunotherapeutic composition has been produced by culturing a whole yeast expressing the MUC1 antigen in a medium that was maintained at a pH level of between 5.5 and 8.

* * * * *